United States Patent
Kossiakoff et al.

(10) Patent No.: US 10,759,834 B2
(45) Date of Patent: Sep. 1, 2020

(54) METHODS AND COMPOSITIONS INVOLVING PROTEIN G VARIANTS

(71) Applicant: The University of Chicago, Chicago, IL (US)

(72) Inventors: Anthony A. Kossiakoff, Chicago, IL (US); Lucas J. Bailey, Chicago, IL (US)

(73) Assignee: The University of Chicago, Chicago, IL (US)

( * ) Notice: Subject to any disclaimer, the term of this patent is extended or adjusted under 35 U.S.C. 154(b) by 304 days.

(21) Appl. No.: 15/519,576

(22) PCT Filed: Oct. 16, 2015

(86) PCT No.: PCT/US2015/055870
§ 371 (c)(1),
(2) Date: Apr. 17, 2017

(87) PCT Pub. No.: WO2016/061427
PCT Pub. Date: Apr. 21, 2016

(65) Prior Publication Data
US 2018/0044385 A1 Feb. 15, 2018

Related U.S. Application Data

(60) Provisional application No. 62/065,156, filed on Oct. 17, 2014, provisional application No. 62/065,516, filed on Oct. 17, 2014.

(51) Int. Cl.
| | | |
|---|---|---|
| C07K 17/00 | (2006.01) |
| C07K 14/315 | (2006.01) |
| C07K 1/22 | (2006.01) |
| C07K 16/00 | (2006.01) |
| G01N 33/543 | (2006.01) |

(52) U.S. Cl.
CPC .............. *C07K 14/315* (2013.01); *C07K 1/22* (2013.01); *C07K 16/00* (2013.01); *C07K 17/00* (2013.01); *G01N 33/54353* (2013.01); *C07K 2317/55* (2013.01); *C07K 2319/00* (2013.01); *C07K 2319/01* (2013.01); *C07K 2319/70* (2013.01); *G01N 2333/315* (2013.01)

(58) Field of Classification Search
None
See application file for complete search history.

(56) References Cited

U.S. PATENT DOCUMENTS

| 2010/0047237 A1 | 2/2010 | DeWildt et al. ............ 424/133.1 |
| 2010/0173430 A1 | 7/2010 | Chung et al. .................. 436/518 |
| 2013/0121915 A1* | 5/2013 | Paas .......................... B82Y 5/00 |
| | | 424/9.1 |

FOREIGN PATENT DOCUMENTS

| WO | WO 1995/006125 | 3/1995 |
| WO | WO 1998/001560 | 1/1998 |

OTHER PUBLICATIONS

Bailey et al., "Applications for an engineering Protein-G variant with a pH controllable affinity to antibody fragments," *J Immunol. Methods*, 2014; 415: 24-30.
Fellouse et al., "High-throughput generation of synthetic antibodies from highly functional minimalist phage-displayed libraries," *J. Mol. Biol.* 2007; 373(4): 924-40.
International Preliminary Report on Patentability issued in Application No. PCT/US2015/055870, dated Apr. 27, 2017.
International Search Report and Written Opinion issued in Application No. PCT/US2015/055870, dated Mar. 11, 2016.
Paduch et al., "Generating conformation-specific synthetic antibodies to trap proteins in selected functional states," *Methods*, 2013; 60(1): 3-14.
Rizk et al., "Allosteric control of ligand-binding affinity using engineered conformation-specific effector proteins," *Nat. Struct. Mol. Biol.*, 2011; 18(4): 437-42.
Spiess et al., "Alternative molecular formats and therapeutic applications for bispecific antibodies," *Molecular Immunology*, 2015; 95-106.
Unverdorben et al., "A Fab-Selective Immunoglobulin-Binding Domain from Streptococcal Protein G with Improved Half-Life Extension Properties," *PLoS One*, 2015; 10(10): 1-13.

\* cited by examiner

*Primary Examiner* — Olga N Chernyshev
(74) *Attorney, Agent, or Firm* — Norton Rose Fulbright US LLP

(57) ABSTRACT

Methods and compositions are provided concerning polypeptides with modifications that increase its binding affinity for the Fab region of an antibody. Methods include using the polypeptides for isolating, detecting, purifying, measuring and quantifying Fab polypeptides. Other embodiments concern kits, compositions, and solid supports containing the polypeptides and for using the polypeptides for isolating, detecting, purifying, measuring and quantifying Fab polypeptide.

12 Claims, 17 Drawing Sheets
Specification includes a Sequence Listing.

METHODS AND COMPOSITIONS INVOLVING PROTEIN G VARIANTS

CROSS-REFERENCE TO RELATED APPLICATIONS

This application is a national phase application under 35 U.S.C. § 371 of International Application No. PCT/US2015/055870 filed Oct. 16, 2015, which claims the benefit of priority of U.S. Provisional Patent Application No. 62/065,156, filed Oct. 17, 2014, and U.S. Provisional Patent Application No. 62/065,516, filed Oct. 17, 2014. The entire contents of each of the above-referenced disclosures are specifically incorporated herein by reference without disclaimer.

The invention was made with government support under Grant No. GM087519 and Grant No. GM094588 awarded by the National Institutes of Health. The government has certain rights in the invention.

BACKGROUND OF THE DISCLOSURE

1. Field of the Disclosure

This disclosure relates to modified Fab-binding regions from protein G that are useful as therapeutics, in protein purification, in diagnostic assays, and in biochemical and immunological assays.

2. Description of Related Art

Immunoglobulin binding proteins (IBPs) are broadly used as reagents for the purification and detection of antibodies. Among the IBPs, the most widely used are Protein-A and Protein-G. The C2 domain of Protein-G from *Streptococcus* is a multi-specific protein domain (Bjorck and Kronvall, 1984); it possesses a high affinity (KD~10 nM) for the Fc region of the IgG, but a much lower affinity (KD~low µM) for the constant domain of the antibody fragment (Fab), which limits some of its applications. Therefore, there is a need in the art for IBPs that have a higher affinity for the Fab domain.

SUMMARY OF THE DISCLOSURE

Described herein are polypeptides comprising modified protein G Fab-binding regions which are engineered to have improved affinity over the wild-type for the Fab region. In some aspects, the disclosure relates to a polypeptide comprising at least one modified protein G Fab-binding domain, wherein the at least one Fab-binding domain of protein G comprises the amino acid sequence with at least 90% homology or identity to $X_{15}TX_{17}X_{18}X_{19}X_{20}X_{21}X_{22}TX_{24}X_A X_{37}X_{38}AX_{40}X_{41}X_{42}X_{43}$ (SEQ ID NO:2); wherein $X_{15}$ is K, R, E, or I; $X_{17}$ is L, F, or A; $X_{18}$ is K, S, W, R, or T; $X_{19}$ is G or Y; $X_{20}$ is E, Y, A, or H; $X_{21}$ is T or R; $X_{22}$ is T, S, A, or G; $X_{24}$ is E, K, T, or Q; $X_{37}$ is Q or R; $X_{38}$ is Y, I, or F; $X_{40}$ is N, Y, F, H, K, or W; $X_{41}$ is D, V, or E; $X_{42}$ is N, H, Q, or Y; $X_{43}$ is G, E, D, or P; and $X_A$ is an amino acid sequence that is 5 to 20 amino acids in length and wherein the modified protein G Fab-binding domain is not KTLKGETTTKAVDAATAEKVFKQYANDNG (SEQ ID NO:19).

In some embodiments, SEQ ID NO:2 is not SEQ ID NO:19, 92, or 93. In some embodiments, SEQ ID NO:2 does not correspond to an unmodified protein G polypeptide known in the art or described herein.

The protein G Fab-binding domain (C-domain) may be any C domain from a protein G. Protein G is an immunoglobulin-binding protein expressed in Streptococcal bacteria. An example of a protein G is shown in SEQ ID NO:1 below:

```
                                          (SEQ ID NO: 1)
EFNKYGVSDYYKNLINNAKTVEGVKDLQAQVVESAKKARISEATDGLSDF

LKSQTPAEDTVKSIELAEAKVLANRELDKYGVSDYHKNLINNAKTVEGVK

DLQAQVVESAKKARISEATDGLSDFLKSQTPAEDTVKSIELAEAKVLANR

ELDKYGVSDYYKNLINNAKTVEGVKALIDEILAALPKTDTYKLILNGKTL

KGETTTEAVDAATAEKVFKQYANDNGVDGEWTYDDATKTFTVTEKPEVID

ASELTPAVTTYKLVINGKTLKGETTTEAVDAATAEKVFKQYANDNGVDGE

WTYDDATKTFTVTEKPEVIDASELTPAVTTYKLVINGKTLKGETTTKAVD

AETAEKAFKQYANDNGVDGVWTYDDATKTFTVTEMVTEVPGDAPTEPEKP

EASIPLVPLTPATPIAKDDAKKDDTKKEDAKKPEAKKEDAKKAETLPTTG

EGSNPFFTAAALAVMAGAGALAVASKRKED.
```

The underlined portions correspond to examples of Fab-binding regions/C regions. In some embodiments, the protein G is from *Streptococcus*. Any of the three C regions shown above may be varied. In some embodiments, only the first, second, or third region is modified. In further embodiments, two of the three C regions are modified. In yet further embodiments, all three C regions are modified.

In some embodiments, the protein G variant or polypeptide comprising the modified protein G Fab-binding region comprises at least 1, 2, 3, 4, 5, 6, 7, 8, 9, or 10 variants as described herein.

In some embodiments, the Fab-binding region is in the context of all or a portion of a protein G polypeptide. In some embodiments, the polypeptide is all or a portion of a protein G described herein (i.e. SEQ ID NO:1, SEQ ID NO:14, SEQ ID NO:15, or SEQ ID NO:16).

In some aspects, the unmodified protein G is SEQ ID NO:14:

```
                                          (SEQ ID NO: 14)
MEKEKKVKYFLRKSAFGLASVSAAFLVGSTVFAVDSPIEDTPIIRNGGEL

TNLLGNSETTLALRNEESATADLTAAAVADTVAAAAAENAGAAAWEAAAA

ADALAKAKADALKEFNKYGVSDYYKNLINNAKTVEGVKDLQAQVVESAKK

ARISEATDGLSDFLKSQTPAEDTVKSIELAEAKVLANRELDKYGVSDYHK

NLINNAKTVEGVKDLQAQVVESAKKARISEATDGLSDFLKSQTPAEDTVK

SIELAEAKVLANRELDKYGVSDYYKNLINNAKTVEGVKALIDEILAALPK

TDTYKLILNGKTLKGETTTEAVDAATAEKVFKQYANDNGVDGEWTYDDAT

KTFTVTEKPEVIDASELTPAVTTYKLVINGKTLKGETTTEAVDAATAEKV

FKQYANDNGVDGEWTYDDATKTFTVTEKPEVIDASELTPAVTTYKLVING

KTLKGETTTKAVDAETAEKAFKQYANDNGVDGVWTYDDATKTFTVTEMVT

EVPGDAPTEPEKPEASIPLVPLTPATPIAKDDAKKDDTKKEDAKKPEAKK

EDAKKAETLPTTGEGSNPFFTAAALAVMAGAGALAVASKRKED.
```

In further embodiments, the unmodified protein G is represented by SEQ ID NO:15:

(SEQ ID NO: 15)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTYKLVINGRTLSGETTTKAV

DAETAEKAFKQYANDNGVDGVWTYDDATKTFTVTE.

The unmodified Fab-binding regions/C regions are underlined in the sequences above. In some embodiments, the unmodified Fab-binding region comprises the sequence: KTLKGETTTKAVDAATAEKVFKQYANDNG (SEQ ID NO:19), KTLKGETTTEAVDAATAEKVFKQYANDNG (SEQ ID NO:92), or KTLKGETTTKAVDAETAEKAF-KQYANDNG (SEQ ID NO:93).

In some embodiments, the polypeptide comprises a modified Fab-binding domain comprising an amino acid sequence with at least 90% homology or identity to one of SEQ ID NOS:3-10. In some embodiments, the polypeptide comprises a modified Fab-binding domain with a sequence corresponding to SEQ ID NO:3. In some embodiments, $X_{43}$ is Glu. In some embodiments, $X_{19}$ is Tyr. In some embodiments, $X_{42}$ is Gln, His, or Tyr. In some embodiments, $X_{40}$ is Tyr or Phe.

In some embodiments, the modified Fab-binding region comprises SEQ ID NO:3 or a sequence having at least 80, 81, 82, 83, 84, 85, 86, 87, 88, 89, 90, 91, 92, 93, 94, 95, 96, 97, 99, or 100%, or any derivable range therein identity or homology with SEQ ID NO:3. In some embodiments, the modified Fab-binding region comprises SEQ ID NO:4 or a sequence having at least 80, 81, 82, 83, 84, 85, 86, 87, 88, 89, 90, 91, 92, 93, 94, 95, 96, 97, 99, or 100%, or any derivable range therein identity or homology with SEQ ID NO:4. In some embodiments, the modified Fab-binding region comprises SEQ ID NO:5 or a sequence having at least 80, 81, 82, 83, 84, 85, 86, 87, 88, 89, 90, 91, 92, 93, 94, 95, 96, 97, 99, or 100%, or any derivable range therein identity or homology with SEQ ID NO:5. In some embodiments, the modified Fab-binding region comprises SEQ ID NO:6 or a sequence having at least 80, 81, 82, 83, 84, 85, 86, 87, 88, 89, 90, 91, 92, 93, 94, 95, 96, 97, 99, or 100%, or any derivable range therein identity or homology with SEQ ID NO:6. In some embodiments, the modified Fab-binding region comprises SEQ ID NO:7 or a sequence having at least 80, 81, 82, 83, 84, 85, 86, 87, 88, 89, 90, 91, 92, 93, 94, 95, 96, 97, 99, or 100%, or any derivable range therein identity or homology with SEQ ID NO:7. In some embodiments, the modified Fab-binding region comprises SEQ ID NO:8 or a sequence having at least 80, 81, 82, 83, 84, 85, 86, 87, 88, 89, 90, 91, 92, 93, 94, 95, 96, 97, 99, or 100%, or any derivable range therein identity or homology with SEQ ID NO:8. In some embodiments, the modified Fab-binding region comprises SEQ ID NO:9 or a sequence having at least 80, 81, 82, 83, 84, 85, 86, 87, 88, 89, 90, 91, 92, 93, 94, 95, 96, 97, 99, or 100%, or any derivable range therein identity or homology with SEQ ID NO:9. In some embodiments, the modified Fab-binding region comprises SEQ ID NO:10 or a sequence having at least 80, 81, 82, 83, 84, 85, 86, 87, 88, 89, 90, 91, 92, 93, 94, 95, 96, 97, 99, or 100%, or any derivable range therein identity or homology with SEQ ID NO:10.

"Identity" refers to sequence similarity between two peptides or between two nucleic acid molecules. Identity can be determined by comparing a position in each sequence which may be aligned for purposes of comparison. When a position in the compared sequence is occupied by the same amino acid, then the molecules are identical at that position. A degree of identity between sequences is a function of the number of matching positions shared by the sequences. An "unrelated" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the sequence identity can be determined using software programs known in the art, for example those described in Ausubel et al. eds. (2007) Current Protocols in Molecular Biology.

Biologically equivalent polynucleotides are those encoding a polypeptide having the same or similar biological activity.

Homology refers to a protein with homologous amino acid substitutions. A protein with 100% homology to a reference sequence which has either the same amino acid sequence or a substituted homologous amino acid. As for example, the following amino acids are would be considered chemically homologous: Leu/Ile/Val; Glu/Asp; Gln/Asn; Ser/Thr; Arg/Lys; Phe/Tyr; In certain embodiments the polypeptides described herein may have 75, 76, 77, 78, 79, 80, 81, 82, 83, 84, 85, 86, 87, 88, 89, 90, 91, 92, 93, 94, 95, 96, 97, 98, 99, or 100% homology (or any derivable range therein).

In some embodiments, the protein G Fab-binding region comprises Glu at position 43 of the modified C domain. For example, the C region may be modified to: LTPAVT-TYKLVINGKTLKGETTTKAVDAETAEKAFKQY-ANDNE (SEQ ID NO:13). This modification allows for the introduction of a pH switch that provides an advantageous molecular property that can be exploited for antibody fragment purification. In some embodiments, the protein G variant or polypeptide comprising the modified protein G Fab-binding region has at least a 300-fold loss or change of affinity between pH 5.5 and pH 4.0. In some embodiments, the polypeptide has a modulation in affinity of 1000-10,000 fold from pH 7 to 4. In some embodiments, the polypeptide has at least a 100, 200, 300, 400, 500, 600, 700, 800, 900, 1000, 5000, or 10000 (or any range derivable therein) fold modulation in affinity from pH 7, 6.5, 5.5, 5, or 4.5 to pH 4 (or any range derivable therein).

In some embodiments, the polypeptide comprises a modification to a non-polar amino acid at position 13 of SEQ ID NO:16 or the corresponding position in a Fab-binding region described herein. In some embodiments, the non-polar amino acid is selected from alanine, cysteine, glycine, isoleucine, leucine, methionine, phenylalanine, proline, tryptophan, tyrosine, and valine. In some embodiments, the non-polar amino acid is selected from alanine, isoleucine, leucine, phenylalanine, valine, proline, and glycine. In some embodiments, the modification at position 13 of the Fab-binding region is from an asparagine to an alanine. In related embodiments, the polypeptide with the above-described modifications at amino acid position 13 provides for a base (OH⁻)-stable polypeptide. In some embodiments, the polypeptides is stable to high concentrations of base such as at least 0.05, 0.1, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 4.5, or 5 (or any derivable range therein) M or N NaOH. These polypeptides have advantages in protein purification, since the a column or solid support comprising these base-stable polypeptides can be efficiently stripped or cleansed without significant loss of bound polypeptide. Efficient stripping will allow for more effective subsequent purifications with the same column, since there will be little to no residual contaminating proteins.

In some embodiments, the protein G Fab-binding region is modified to have Tyr at position 19. In some embodiments, the C domain comprises Gln, His, or Tyr at position 42 of the modified C domain. In some embodiments, the C domain comprises Tyr or Phe at position 40 of the modified C domain.

In some embodiments, $X_A$ comprises a helix or alpha-helical structure. The prediction of secondary structures is well within the skill of one in the art, and many tools and software programs are publically available to predict secondary structures of proteins. For example, an on-line tool for predicting secondary structures of proteins can be found on the world wide web at predictprotein.org.

In some embodiments, $X_A$ comprises a sequence with at least 80% homology or identity to AVDAATAEKVFK (SEQ ID NO:51). In some embodiments, the polypeptide further comprises $X_B$, which is a N-terminal region immediately before $X_{15}$, and wherein $X_B$ has at least 80% homology or identity to LTPAVTTYKLVING (SEQ ID NO:52). In some embodiments, the polypeptide further comprises $X_C$, which is a C-terminal region immediately after $X_{43}$, and wherein $X_C$ has at least 80% homology or identity to VDGEWTYDDATKTFTVTEKPEVI (SEQ ID NO:53).

In some embodiments, the polypeptide further comprises a variant isotype recognition region. The isotype recognition region corresponds to amino acids YANDNG (SEQ ID NO:18) of a protein G polypeptide. This region is repeated in the protein G polypeptides described throughout the disclosure. Any one of the isotype recognition regions may be varied in the protein G polypeptides described herein. In one embodiment, the varied isotype recognition region corresponds to amino acids 162-167 of SEQ ID NO:15. In some embodiments, the variant isotype recognition region is modified to one of SEQ ID NO:20-26 or a homolog thereof. In some embodiments, the polypeptide further comprises at least one variant isotype recognition region comprising the sequence YSRPHV (SEQ ID NO:21) or YAYGAV (SEQ ID NO:22).

In some embodiments, the polypeptide comprises a variant immunogenicity region having a sequence with at least 90% homology or identity to $X_2'VIX_5'GX_7'X_8'X_{10}'X_{11}'$ (SEQ ID NO:101), wherein $X_2'$ is L or F; $X_5'$ is N, R, G, M, I, S, or L; $X_7'$ is R, L, V, I, or S; $X_8'$ is T or R; X10' is S, W, L, G, or R; X11' is L, F, or V; and wherein the variant immunogenicity region is not LVINGRTLSG (SEQ ID NO:50). In some embodiments, the variant immunogenicity region is selected from SEQ ID NOS:27-49.

In some embodiments of the current disclosure, the polypeptide, as described herein, refers to a protein G polypeptide or portion thereof.

In some embodiments, the polypeptide further comprises one or more Fc regions or portions thereof. The term Fc region (fragment crystallizable region) is the stalk region of an antibody that interacts with cell surface receptors called Fc receptors and some proteins of the complement system. This property allows antibodies to activate the immune system.

In some embodiments, the polypeptide further comprises a targeting moiety. The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments (e.g. Fabs), transferrin, HS-glycoprotein, coagulation factors, serum proteins, .beta.-glycoprotein, G-CSF, GM-CSF, M-CSF, EPO and the like.

In some embodiments, the polypeptides and/or fusion proteins descried herein are conjugated to a therapeutic moiety. The term "therapeutic moiety" means any agent useful for therapy including, but not limited to, antibiotics, and -inflammatory agents, anti-tumor drugs, cytotoxins, and radioactive agents. "Therapeutic moiety" includes prodrugs of bioactive agents, constructs in which more than one therapeutic moiety is bound to a carrier, e.g, multivalent agents. Therapeutic moiety also includes proteins and constructs that include proteins. Exemplary proteins include, but are not limited to, Granulocyte Colony Stimulating Factor (GCSF), Granulocyte Macrophage Colony Stimulating Factor (GMCSF), Interferon (e.g., Interferon-.alpha., -.beta., -.gamma.), Interleukin (e.g., Interleukin II), serum proteins (e.g., Factors VII, VIIa, VIII, IX, and X), Human Chorionic Gonadotropin (HCG), Follicle Stimulating Hormone (FSM) and Lutenizing Hormone (LH) and antibody fusion proteins (e.g. Tumor Necrosis Factor Receptor ((TNFR)/Fc domain fusion protein)).

Further embodiments relate to a fusion protein comprising two or more polypeptides described herein.

Further aspects of the disclosure relate to a fusion protein comprising a fusion between two or more polypeptides or protein G variants described herein. Fusion of the polypeptides or protein G variants allows for binding of multiple Fab polypeptides to the fusion protein. This has the potential to make a polypeptide that has multivalency with respect to the Fab regions, and such complexes can recognize more than one epitope if different Fabs are bound to the same fusion protein. The protein G variants may be fused directly to each other or through a linker. In some embodiments, the linker comprises glycine and serine residues. In some embodiments, the linker comprises GGGS (SEQ ID NO:11). In some embodiments, the linker comprises GGGSGGGSGGGS (SEQ ID NO:12). In some embodiments, the linker comprises at lease 3, 4, 5, 6, 7, 8, 9, 10, 11, 12, 13, 14, 15, 20, 30, 40, 50, 60, or 100 amino acids, or any derivable range therein. The linker may also be one known in the art such as a short linker (SL) (e.g. LAAA (SEQ ID NO:94)); flexible linkers comprised mostly of glycine and serine such as SEQ ID NO:11, 12, or LGGGGSGGGGSGGGGSAAA (SEQ ID NO:95) or LSGGGGSGGGGSGGGGSGGGGSAAA (SEQ ID NO:96); a helical linker such as LAEAAAKEAAAKAAA SEQ ID NO:97), LAEAAAKEAAAKEAAAKAAA (SEQ ID NO:98), LAEAAAKEAAAKEAAAKEAAAKAAA (SEQ ID NO:99), or LAEAAAKEAAAKEAAAKEAAAKEAAAKAAA (SEQ ID NO:100).

In some embodiments, the fusion protein or polypeptides described herein produce a multi-valent complex. In some embodiments, the fusion protein specifically binds to at least one light chain constant region of a Fab or antibody. In some embodiment, the fusion protein comprises at least two protein G polypeptides, wherein each polypeptide specifically binds to one light chain constant region of a Fab or antibody, and wherein the fusion protein is multi-specific for different constant regions. For example, polypeptides of the disclosure may comprise one polypeptide with a modified protein G Fab-binding region and an isotype-recognition region that specifically binds to the light chain kappa-isotype constant region of a Fab fused to another polypeptide with a modified protein G Fab-binding region that has an isotype-recognition region that specifically binds to a light chain HS-isotype constant region of a Fab, a human 4D5 scaffold with residues PEELRTNK (SEQ ID NO:102; FIG. 11C) replacing light chain positions 122-129. This is useful for binding different Fabs in a specified order, and can create bi-specific or multi-specific complexes of various configurations.

Further aspects relate to a protein complex comprising the polypeptides or fusion proteins described herein operatively linked to at least one Fab polypeptide. The term "operatively linked" refers to a situation where two components are combined to form the active complex prior to binding the target site. For example, a molecule conjugated to one-half of a biotin-streptavidin complex and another molecule complexed to the other one-half of the biotin-streptavidin complex are operatively linked through complexation of the biotin and streptavidin. In the case of the Fab-binding domain of protein G and the Fab polypeptide, the proteins may be operatively linked through their binding affinity for each other. The term operatively linked is also intended to refer to covalent or chemical linkages that conjugate two molecules together. In some embodiments, the protein G polypeptide or fusion protein is covalently linked to the Fab polypeptide(s). In some embodiments, the fusion protein is antigen multi-specific. Multi-specific refers to a protein that binds to more than one epitope or antigen. Multi-valent refers to a polypeptide that has more than one binding site for an antigen or epitope.

Further aspects of the disclosure relate to polypeptides comprising a variant immunogenicity region and/or a variant isotype recognition region. The polypeptide may have a modified Fab-binding region or a wild-type Fab binding region or be at least 80% identical or homologous to a protein G polypeptide or portion thereof described herein or known in the art. The polypeptides may also include any of the other features described herein and may be used in the compositions and methods described herein. In some embodiments, the disclosure relates to polypeptides with at least 80% sequence identity or homology to SEQ ID NOS: 62-91.

Further aspects relate to a nucleic acid encoding for the protein G variant or polypeptides, or fusion proteins described herein. Also described is a plasmid comprising such nucleic acids and a host cell comprising such nucleic acids or plasmids.

Other aspects of the disclosure relate to a method for purifying Fab polypeptides from a composition comprising Fab proteins and additional components, the method comprising: conjugating the protein G variant or polypeptides described here to a solid support; contacting a composition comprising the Fab polypeptides with the solid support; washing the solid support to remove any unbound components; and eluting the Fab polypeptides from the solid support by dissociating the Fab from the polypeptide comprising the modified protein G binding region. In some embodiments, the Fab and modified Fab-binding region are dissociated by contacting the Fab and protein G complex with an elution composition having a pH lower than 5.0. In some embodiments, the elution composition has a pH of 4.5 or less. The pH-dependent affinity of the protein variants described herein allow for the easy purification of binding molecules without the use of harsh assay conditions that may denature or contaminate the purified polypeptide.

Therefore, embodiments of the purification method are included wherein the purification method does not comprise one or more of detergents, salt concentrations of greater than 1, 1.5, 2, or 3% w/v, or salt concentrations greater than the level of physiological saline (about 0.9% w/v NaCl).

Also described herein is a method for multimerizing Fab polypeptides and/or providing multivalent polypeptide-Fab complexes comprising contacting Fab polypeptides with the fusion protein described herein. The Fab polypeptides may be a Fab region of an antibody, for example. When the term, "Fab polypeptide" is used herein, it is understood that this term refers to a polypeptide comprising a Fab region, which is the antigen-binding region of the antibody. Furthermore, Fab polypeptides may refer to a collection of one type of Fab polypeptide (i.e. Fab polypeptides that bind specifically to one epitope) or to a collection of two or more Fab polypeptides (i.e. polypeptides that bind to more than one epitope). It is contemplated that 2, 3, 4, 5, 6, 7, 8, 9, or 10 or more (or any range derivable therein) of the same or different Fab polypeptides are multimerized with one or more Protein G variants.

Further aspects of the disclosure relate to a multimerized Fab polypeptide comprising a fusion protein with a Fab polypeptide; wherein at least two Fab polypeptides are bound with one protein G variant fusion protein. It is also contemplated that the protein G variant may be conjugated to one or more other protein G variants, which may or may not differ in sequence from one another.

Other aspects relate to a method for determining whether a composition has a target antigen, the method comprising: immobilizing the target antigen to a solid support; contacting the target antigen with i) Fab polypeptides that specifically bind the target antigen and ii) the protein G variant, polypeptide comprising the modified protein G Fab-binding region, or the fusion protein described herein; and detecting antigen binding to the Fab polypeptide. In this assay, the detection step may be done by detecting a label attached to either the polypeptide/fusion protein comprising the modified Fab-binding domain(s), or the Fab polypeptide, which are complexed together. Therefore, in some embodiments, the Fab polypeptide is attached to a detectable label, and in further embodiments, the polypeptide comprising the modified protein G Fab-binding domains is attached to a detectable label. The target antigen may be present in a patient sample such as a blood sample, urine sample, mucus sample, saliva sample, and the like. The antigen may be immobilized to the solid support using techniques known in the art such as absorption to the surface or by way of capture by another antibody specific for the same antigen, for example. As previously discussed, the Fab polypeptides may be to one epitope or a mixture of different Fab polypeptides that target multiple antigenic epitopes.

Other aspects relate to a method for determining whether a composition has a target antigen, the method comprising: immobilizing the target antigen to a solid support; contacting the target antigen with i) Fab polypeptides that specifically bind the target antigen and ii) the protein G variant, polypeptide comprising the modified protein G Fab-binding region or the fusion protein described herein; and detecting antigen binding to the Fab polypeptide. In this assay, the detection step may be done by detecting a label attached to any of the polypeptides of the assay. Therefore, in some embodiments, the Fab polypeptide is attached to a detectable label, and in further embodiments, the protein G, fusion protein, or polypeptide comprising the modified protein G Fab-binding domain is attached to a detectable label. The target antigen may be present in a patient sample such as a blood sample, urine sample, mucus sample, saliva sample, and the like. The antigen may be immobilized to the solid support using techniques known in the art such as absorption to the surface or by way of capture by another antibody specific for the same antigen, for example. As previously discussed, the Fab polypeptides may be to one epitope or a mixture of different Fab polypeptides that target multiple antigenic epitopes.

A further aspect relates to a kit comprising: a solid support capable of immobilizing the target antigen; the protein G variant, polypeptide comprising the modified protein G Fab-binding region, or the fusion protein described herein; and Fab polypeptides that specifically recognize the target antigen.

Further aspects relate to an antigen-binding therapeutic comprising a polypeptide, fusion protein, or protein complex described herein.

Further aspects relate to a method for making the polypeptide, or fusion protein as described herein, the method comprising expressing the polypeptide in a host cell.

It is contemplated that the embodiments disclosed herein may be used interchangeably in any of the polypeptide, fusion protein, protein complex, and method aspects described above. Furthermore, it is also contemplated that any of the above-described embodiments may be specifically excluded from the claimed invention.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DESCRIPTION OF ILLUSTRATIVE EMBODIMENTS

Figures 6A, 6B, 6C, 6D, 6E:
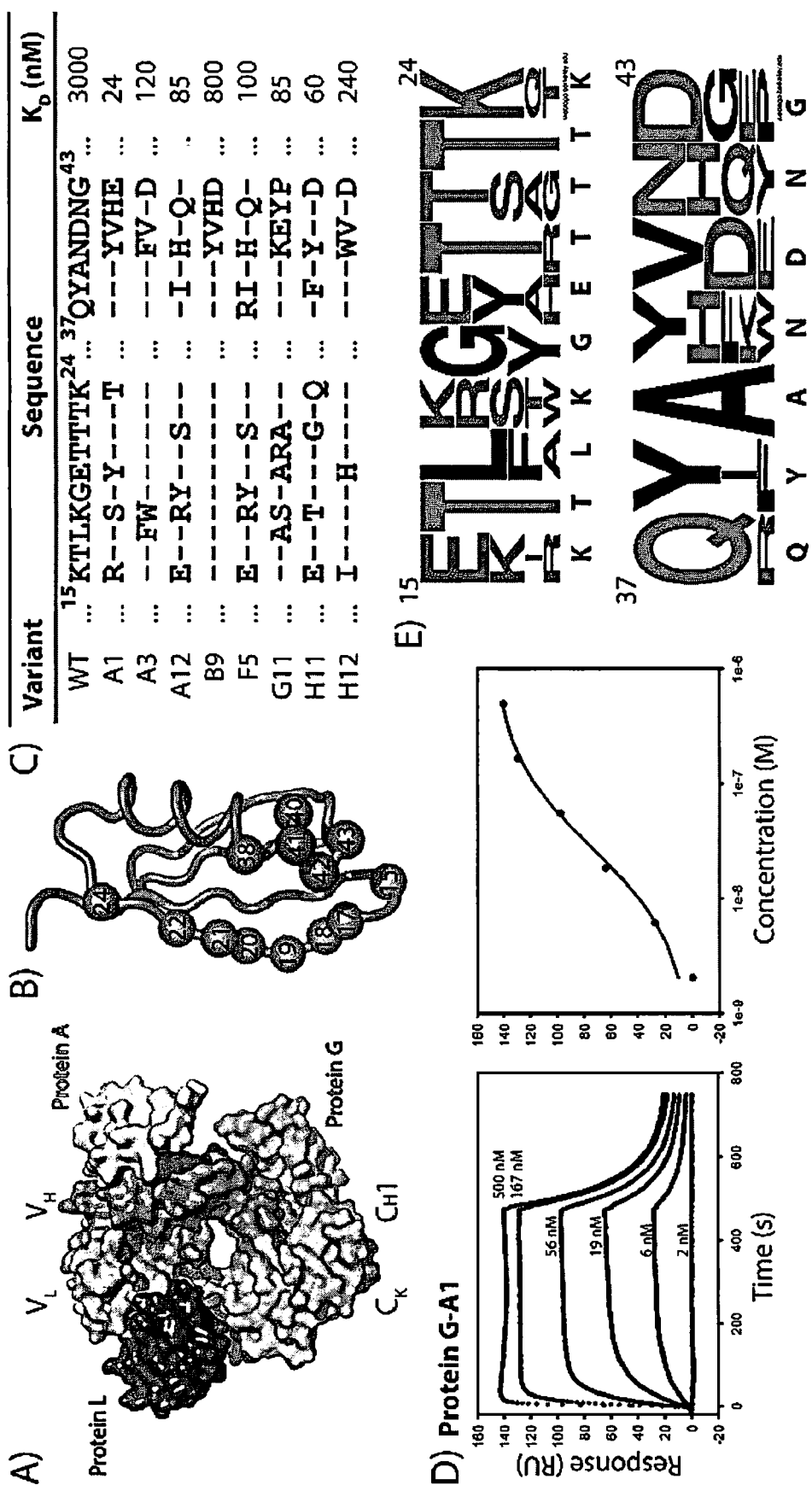
FIGS. 6A-6E—Library Design strategy and engineering of Protein G. A. Immunoglobulin binding protein localization on the antibody fragment. Protein L and protein A bind to the variable region of the Fab while protein G binds to the constant domain. B) Soft randomized residues are depicted as spheres on the protein G scaffold. C. Engineered protein G variants possessed ~3-100-fold higher affinity to the human IgG1 scaffold than the wild type sequence. D. Representative surface plasmon resonance trace for equilibrium binding analysis of protein G-A1. E. Weblogo plot of the engineered sequences of protein G. In a Weblogo plot the preference for an amino acid type is correlated with the size of the letter representing its one letter code.

Although IBPs are convergent evolved bacterial proteins, they have different tertiary structures and different modes of binding to IgG (antibody) scaffolds (FIG. 6A). Prominent among this group of IBPs is Protein-G from Groups C and G *Streptococcus*, which is a multi-domain cell surface protein possessing albumin and immunoglobulin binding domains. Other functionally related IBPs are Protein-A from *Staphylococcus*, Protein-L from *Peptostreptococcus magnus* and Protein-M from *Mycoplasma*. Like Protein-G, these IBPs are multidomain proteins that have their repeated binding domains linked together like "beads on a string". The inherent ability to recognize conserved regions of the IgG scaffold enable Protein-G and other IBP's to bind to antibodies from a wide range of species and to different surface epitopes and thus, can be utilized in different applications. Described herein are polypeptides with protein G Fab binding domains that have been modified to significantly increase the affinity to the Fab. These polypeptides are useful in therapeutic and biochemical applications.

I. Modified Protein G Fab Binding Domain

A. Variations from Wild-Type

In some embodiments, the polypeptides described herein comprise a protein G polypeptide or portion thereof. For example, SEQ ID NO:15 describes a wild-type non-modified protein G polypeptide, and SEQ ID NO:16 describes a wild-type non-modified protein G Fab binding domain. However, there are natural variations to this polypeptide. For example, protein G from *Streptococcus* sp. 'group G' (Accession No: CAA37410) is 98% identical to SEQ ID NO:15, and varies at amino 78, 139, and 142 with respect to SEQ ID NO:15. GenBank Accession No: P19909 has an additional N and C-terminal sequence, has 98% identity to SEQ ID NO:15, and varies at amino acids 78, 139, and 142 with respect to SEQ ID NO:15. The N-terminal portion of P19909 also shares 91% identity to amino acids 57-185 of SEQ ID NO:15 and varies at amino acids 58-60, 65, 66, 78, 139, 142, 148, 153, 158, and 171, with respect to SEQ ID NO:15. Protein G from *Streptococcus dysgalactiae* subsp. *Equisimilis* (Accession No: KKC16415) shares about 94% identity with amino acids 57-185 of SEQ ID NO:15 and varies at amino acids 58-60, 65, 66, 78, 139, and 142, with respect to SEQ ID NO:15. Protein G from *Streptococcus dysgalactiae* (Accession No: WP 042357947) shares about 91% identity with amino acids 57-185 of SEQ ID NO:15 and varies at amino acids 58-60, 65, 66, 74, 78, 123, 126, 139, and 142, with respect to SEQ ID NO:15. In some instances in the variants described above, the substitution is a conservative or non-conservative substitution. Based on the natural variants known in the art, one can easily envision polypeptides of the current disclosure that share a certain percent identity to the wild-type protein G and retain Fab binding activity.

It is contemplated that the polypeptides described herein may have a sequence that has a certain percent identity to a wild-type sequence and varies with conservative substitutions. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue's side chain with one that is chemically dissimilar, such as a polar or charged amino acid for a nonpolar or uncharged amino acid, and vice versa.

B. Correlation of Structure and Functional Fab-Binding Characteristics of Protein G Polypeptides and Polypeptides Comprising Modified Protein G Fab-Binding Domains.

Figures 11A, 11B, 11C:
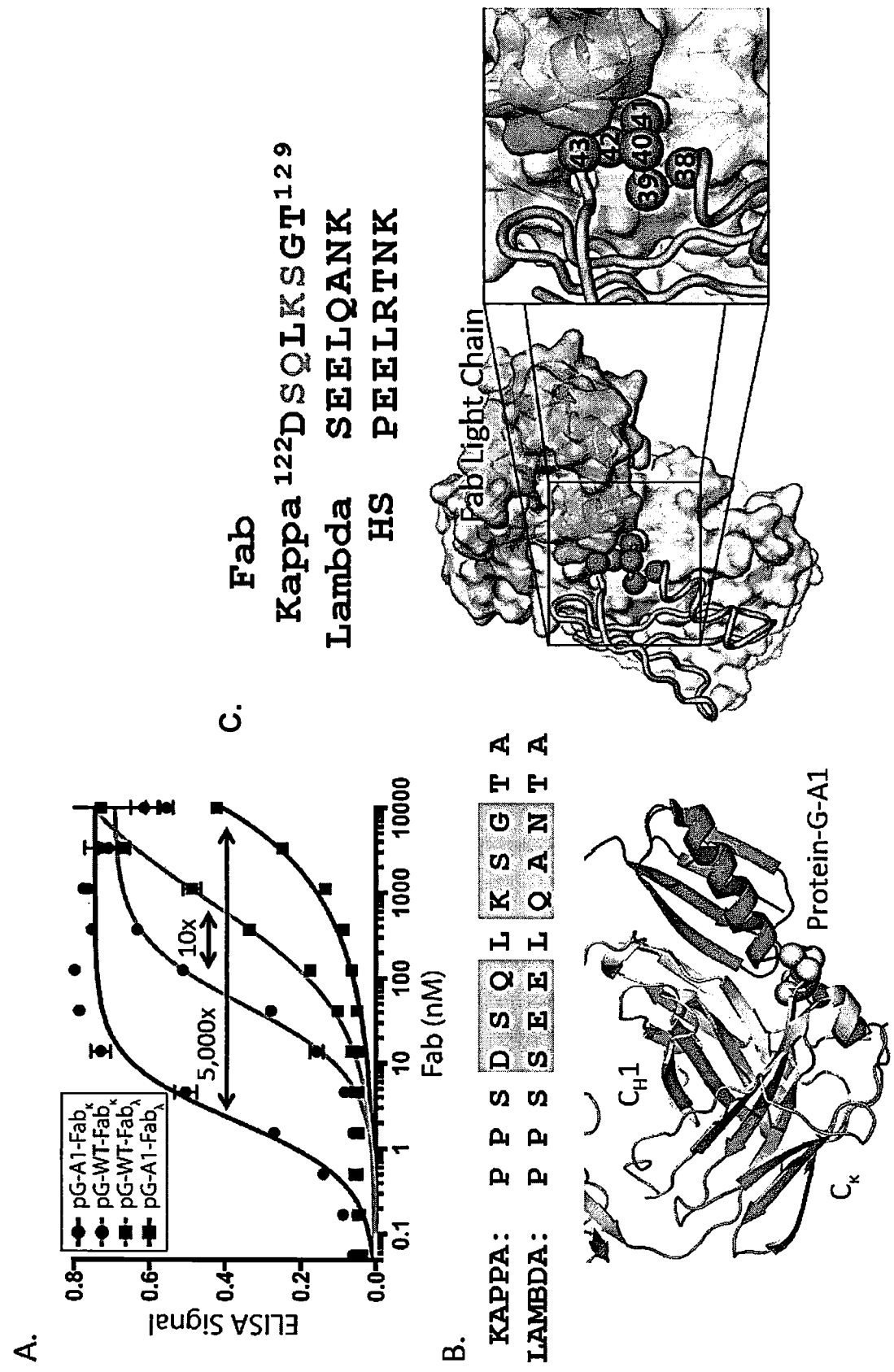
FIG. 11A-11C—Specificity of Protein-G-A1. A. ELISA data demonstrate Protein-G-A1 exhibits 5000-fold difference in affinity for kappa and lambda light chains indicating the structural differences between light chain isotypes control molecular recognition. B. Sequence comparison and structural basis of Protein-G-A1 specificity. Protein-G-A1 buries ~200 Angstroms$^2$ at the light chain interface. Shown are the kappa sequence (SEQ ID NO:103) and the lambda sequence (SEQ ID NO:104). C. Sequences of light chain constant binding region to isotype recognition region. Shown is the kappa sequence (SEQ ID NO:105), lambda sequence, (SEQ ID NO:106), and HS sequence, (SEQ ID NO:102). The positions of the residues mutated in the phage display selection experiments are designated and shown as spheres.
Figure 12:
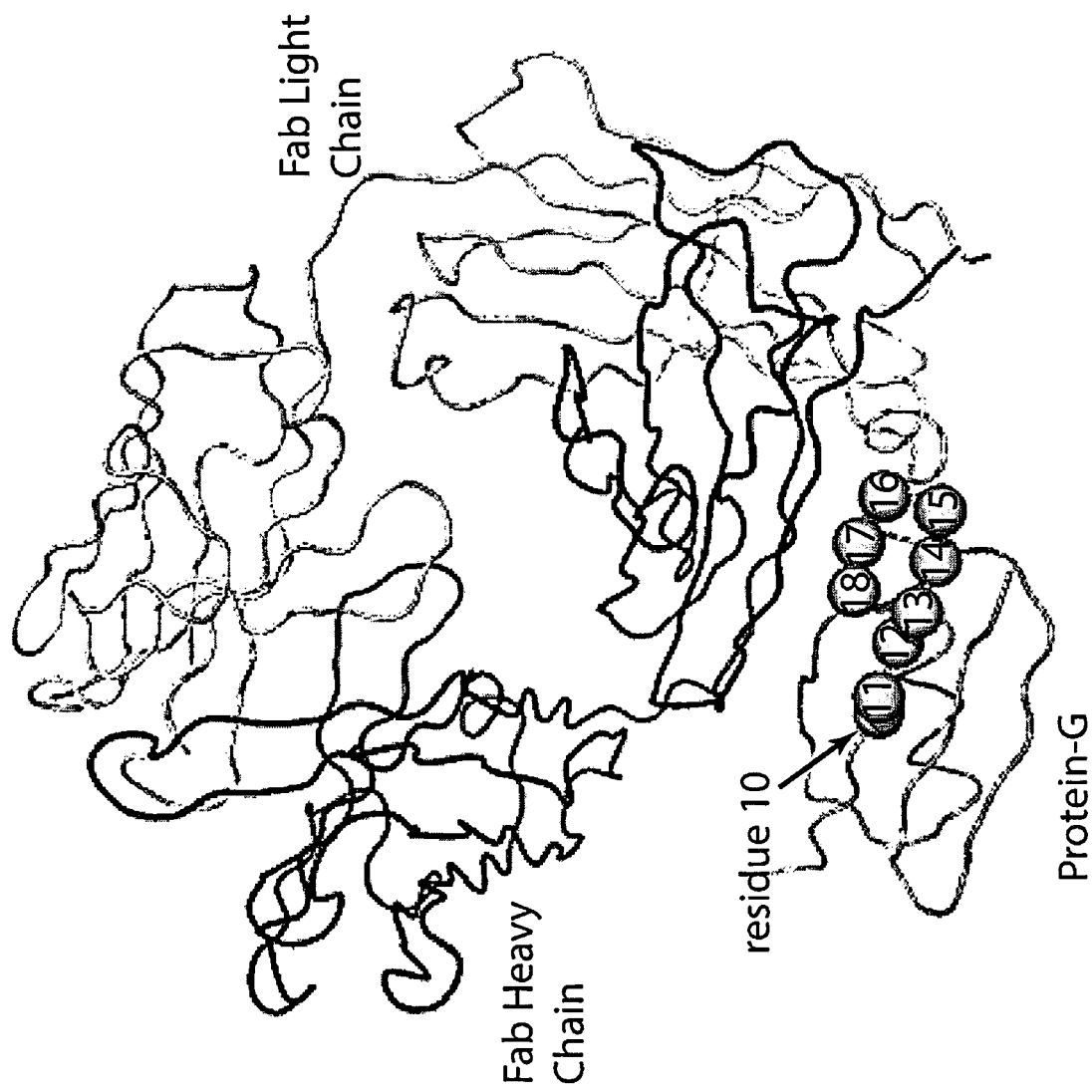
FIG. 12—Structural analysis of Protein-G-Fab complex. The T-cell epitope of Protein-G-A1 (residues 10-18) resides on beta-strands 1 and 2 with several residues participating in the protein-protein interface.

Based on the X-ray crystal structure of the affinity-matured protein G-A1-(SEQ ID NO:54)-Fab-Asf1 ternary complex that was determined, it is clear that the binding footprint is virtually identical to the wild-type Protein-G (Protein Data Bank entry UGC) ( ). Protein-G interacts with the Fab fragment through an interaction dominated by an antiparallel beta-strand configuration providing the origin of the broad isotype and species specificity (FIG. 11B). The engineered interface of Protein G-A1 contains several mutations that bury significant surface area at the protein interface. Serine18 of the modified A1 domain buries ~35 Å$^2$ while also contributing hydrogen bonds through the backbone peptide bond. The position of the modification is relative to the wild-type Fab binding region, which is shown in SEQ ID NO:16. Therefore, Serine 18 refers to a modification to a serine at position 18 of SEQ ID NO:16. This same reference is used in the following paragraphs when discussing the structure/function of the modifications in the protein G-A1 variant (SEQ ID NO:54). The most notable mutation at the beta strand interface is Tyr20 which provides ~70 Å$^2$ of interface for complex formation. This is achieved through substantial van der Waals interactions with the alkyl chain Lys214 from Fab $C_H1$. In total, protein G-A1 buries ~500 Å$^2$ at the Fab $C_H1$ interface, comparable to the original parent domain (550 Å$^2$).

The largest changes within Protein-G-A1 interface occur at the C-terminal cap of the α-helix. Here, residues 40-43 ($^{40}$NDNG$^{43}$) are mutated to $^{40}$YVHE$^{43}$ in the engineered variant. The engineered helical cap provides exquisite shape complementarity to interdigitate within the alpha helix connecting beta strands 1 and 2 of $C_K$ at the heavy and light chain interface (FIG. 11C). Tyr40 interacts with the $C_k$ domain, burying ~45 Å$^2$ primarily through contacts of its aromatic ring with the alkyl side chain of Lys126 of $C_K$. Val41 buries roughly 90 Å$^2$, through interactions with Ser127 of $C_K$. His42 of Protein-G-A1 is buried at the $C_H1$ interface where its Nε2 forms a hydrogen bond to the main chain nitrogen of the $C_H1$ Val129 peptide bond, a hydrogen bonding interaction analogous to the polar interactions formed by Asn42 of the parent domain. The hydrogen bonding potential at this position appears to be conserved as most variants isolated at this position are either His, Asn or Gln. Glu43 projects into a groove formed by Lys126 and Glu123 to bury ~70 Å$^2$. Many of the newly introduced residues make extensive contact with the light chain in a manner distinct from the parent domain. As a result ~100 Å$^2$ of additional surface area is buried in $C_K$, providing a small protein scaffold additional surface area to recognize its molecular partner with high affinity. Notably, the region of $C_K$ (kappa) interacting with the light chain differs significantly from the $C_\lambda$ (lambda) isotype. To probe the contribution of the light chain to the affinity of the wild type and Protein-G-A1 variants, Applicants performed ELISA experiments to determine the relative affinities (FIG. 11A). The wild type domain possessed a ~7-fold lower EC$_{50}$ for $C_K$ than $C_\lambda$ while Protein-G-A1 preferred $C_K$ with an EC$_{50}$ ratio greater than 5000. This can be rationalized structurally as several residues that help form the distinct grooves into which the C-terminal helical cap of Protein-G-A1 interdigitates vary as a function of light chain isotype. Notably, a Lys126→Gln substitution potentially diminishes the shape complementarity of the alkyl chain projecting into the groove formed by Glu43 and Tyr40 of Protein-G-A1 as well as abolishing potential electrostatic contacts between Lys126 and Glu43. Further conformational changes within the architecture of the light chain helix likely provide subtle differences to this epitope when presented to Protein-G. Ultimately, engineering of the Fab-Protein-G interface enabled molecular recognition of a quaternary epitope created through the $C_H/C_L$ interface and provides a route to endow specificity that an interaction dominated by beta-strand interaction is unlikely to achieve.

C. Phage Panning

The Protein-G-A1 helical cap library was subjected to phage panning where Fabs with unique light chain sequences were immobilized through streptavidin-biotin linkage for standard selection methods. Notably, during the phage display selection, an excess of wild type Fab, which has a kappa light chain, was added as a competitor to favor the enrichment of isotype-specific Protein-G reagents. Any binders that bind to the wild type Fab are captured and washed away, leaving only those that bind specifically to the modified light chain.

Subsequent analysis of Protein-G variants yielded clones specific to Fab$_{HS}$ (a human 4D5 scaffold with residues PEELRTNK (SEQ ID NO:102; FIG. 11C) replacing light chain positions 122-129). Here, protein ELISA indicated minimal cross-reactivity of Protein-G$_{HS}$ variants C6 and C7 (YSRPHV (SEQ ID NO:21) and YAYGAV (SEQ ID NO:22), respectively) while there was robust binding to Fab$_{Hs}$ (IC$_{50}$~8 nM and 100 nM for C6 and C7, respectively).

These results validate the Protein-G library design and selection strategy for the generation of orthogonal Protein-G reagents.

D. Multi-Valent Polypeptides Comprising Modified Protein G Fab Binding Domains

Figures 1A, 1B, 1C, 1D:
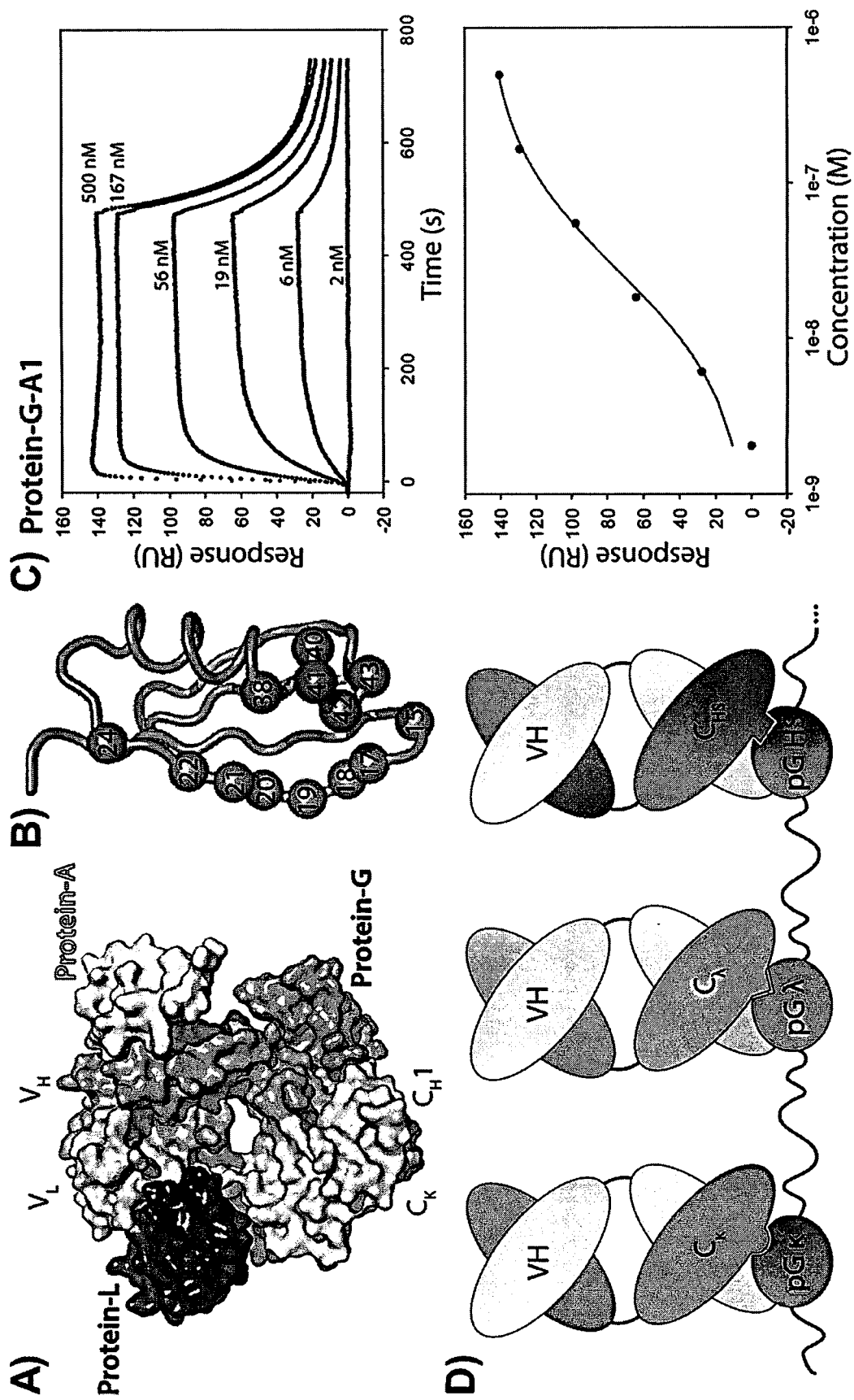
FIGS. 1A-1D—Engineering of Protein-G. A) Cartoon of antibody structure showing the different chains and domains. BBinding epitopes of immunoglobulin proteins on the antibody fragment. C). Residues randomized on Protein-G are represented as spheres. D). Cartoon schematic of Protein-G-strings to orthogonally engage diverse light chain isotypes.

Multi-valency is a common feature of many biological systems that harness the simultaneous engagement of tethered ligands to multiple receptors. Polypeptides and fusion proteins of the current disclosure include multi-valent proteins made by fusing multiple protein G Fab binding domains together. Biological processes use this as a means to increase the effective affinity of weak binding ligands as well as to qualitatively modify the activity of proteins through muliti-valent engagement and molecular crosslinking A notable example of bi-valency is an antibody, which exploits its two identical Fab antigen-binding arms to improve the affinity of antigen recognition and induce receptor crosslinking (FIG. 1A). Traditionally, antibodies have been produced by animal immunization and propagated through hybridoma technology. However, this approach has significant limitations. Since the animal strongly influences the antibody repertoire that results, there is no control over which epitopes on the antigen are targeted and immune-dominant epitopes may not be those of interest. Further, while hybridomas produce antibodies, they do not directly provide the encoding DNA. Antibody sequences drift over time and the cells die so that the antibody source is not renewable. Over the last two decades, phage display derived antibodies have become a more versatile alternative to hybridoma-based technology. The completely in vitro process offers a number of technical advantages over traditional methods including exquisite control of the selection conditions and the ability to raise antibodies against highly conserved epitopes. Applicants have helped develop novel synthetic antibody libraries based on "restricted chemical diversity" where residues within the antibody antigen binding loops of the antibody Fab fragment are enriched in amino acids typically found at the antibody paratope. Such libraries, based on the 4D5 Fab scaffold, have successfully produced affinity reagents to a wide range of targets. Furthermore, Fab fragments derived from synthetic libraries allow for the potential to move beyond the IgG format, enabling facile prokaryotic expression and further functionalization through genetic manipulation. One of the major bottlenecks in the large-scale generation and characterization of affinity reagents is their expression and purification for subsequent biophysical, structural and cell-based studies. Here, researchers select reagents based on their expression levels, stability and their ability to bind the Fab rather than the Fc.

While phage display mutagenesis is probably the most widely used directed evolution approach to generate antibody-based affinity reagents, yeast display and ribosome display methods are also viable approaches. Antibody fragments can take different forms than Fabs, but ultimately to reformat them into IgG molecules if desired, they have to be converted into Fabs as part of the process. Thus, in performing the display selections it can be more efficient to use the Fab scaffold. A further advantage is that Fab domains are generally much more stable than other forms, for instance the single chain version of the variable heavy chains (scFv). Because most of the recombinant methods to generate antibody like molecules will likely involve engineering Fab domains at some level, there is a need to develop better methods to purify Fabs in ways that do not compromise their structural integrity and to eliminate unwanted degradation products that are inherent in their expression.

Figure 2A:
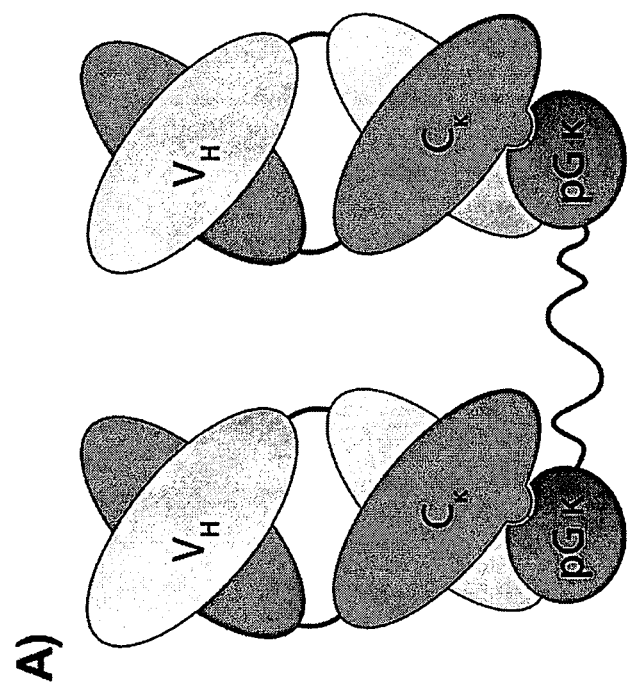
FIGS. 2A-2B—Multivalency of Protein-G-A1. A). Cartoon schematic of a Protein-G-A1 dimer bound to Fab. B). ELISA signal of Fab binding to Protein-G-A1 dimer versus monomer. Utilization of a non-covalent Protein-G-A1 dimer resulted in ~10-fold improvement in the EC50 of a low affinity Fab-antigen interaction.
Figure 2B:
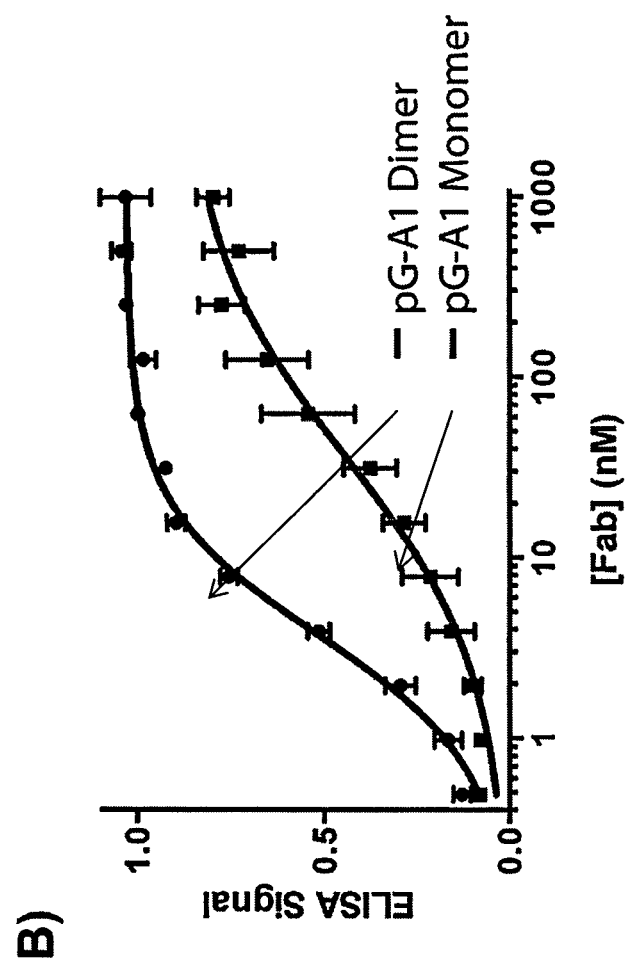
Figures 3A, 3B, 3C:
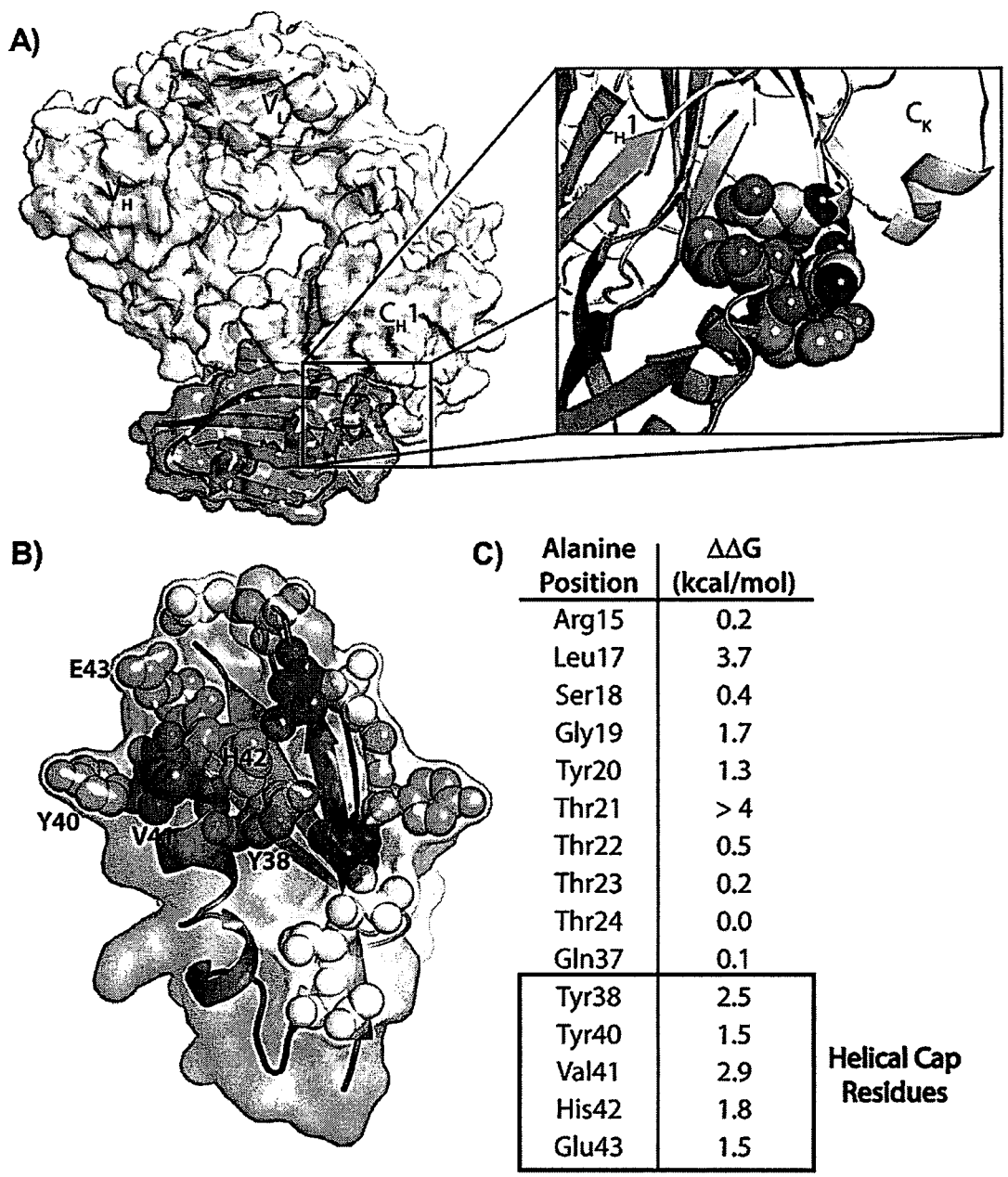
FIG. 3A-3C—Antibody fragment light-chain interactions with Protein-G-A1. A). Structure of Protein-G-A1 bound to Fab with a close-up of the Protein-G-A1-Fab light-chain interaction. B). Protein-G-A1 structure colored by ΔΔG values as determined by Alanine-scanning by equilibrium SPR (white=low, red=high). C). Table of Protein-G-A1 Alanine-scan ΔΔG values. Residues in the box contains the ones contained in the helix-cap motif.

Linking together Protein-G binding domains containing specially engineered properties could produce molecules that bind multiple copies of an antibody Fab (FIG. 2). These constructs could capitalize on the resulting multi-valency to perform myriad new binding functions beyond those available to natural antibodies. This is because the two Fab arms of the Y-shaped antibody scaffold have significant structure limitations in how they are able to jointly present their binding paratopes toward their molecular targets. The multi-valent Protein-G constructs presumably would not have similar constraints since the linker regions between the engineered binding domains can be adjusted for length, flexibility and composition. Thus, this type of construct allows for the facile generation of a range of multivalent scaffolds where oligomeric state, specificity, linker length and geometric arrangement can be predictably controlled. Such scaffolds will serve as powerful reagents for applications where simultaneous engagement of multiple binding sites can provide enhancements in affinity and activity.

Figure 13:
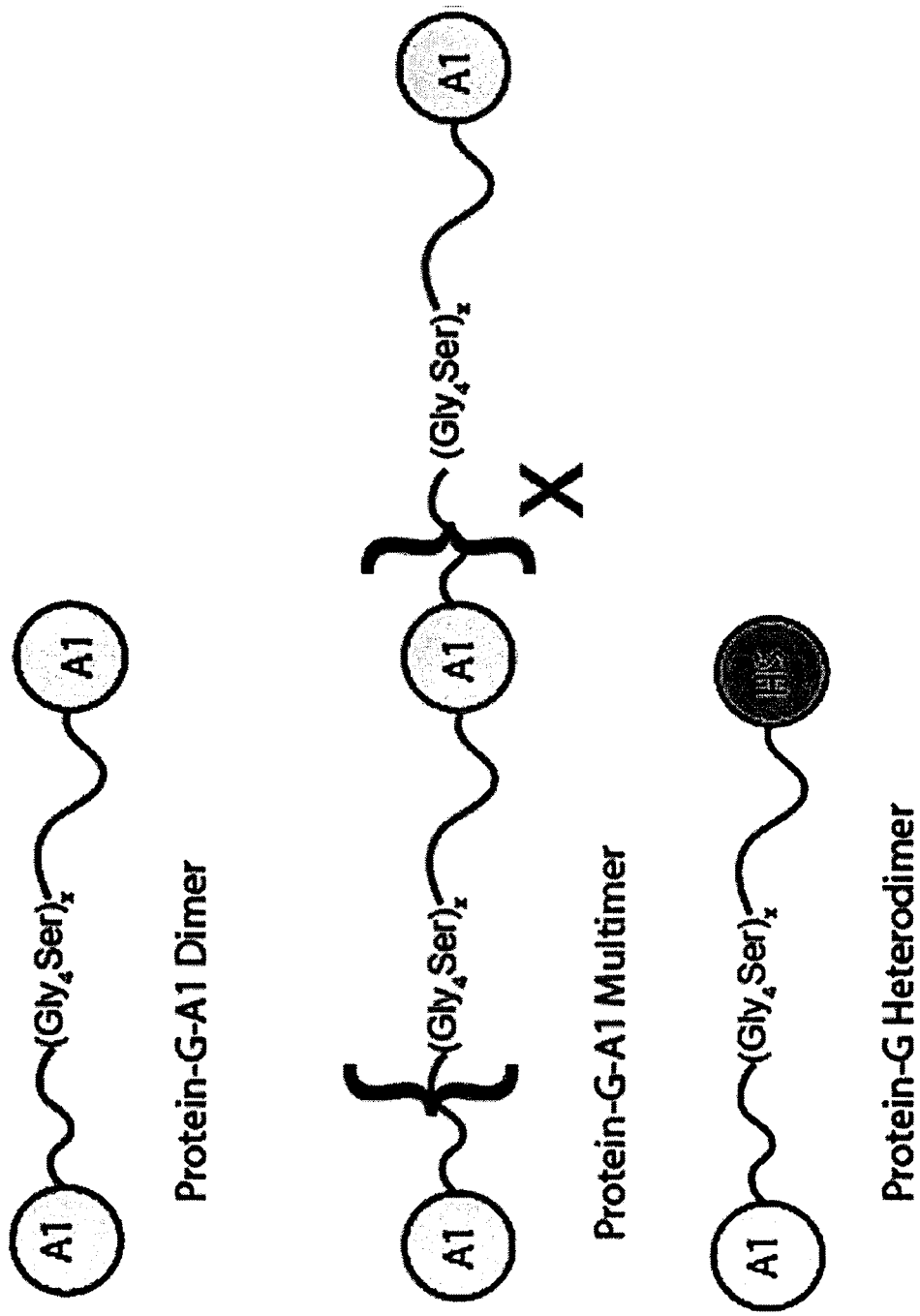
FIG. 13 shows exemplary embodiments of multimeric modules. Linkers can be readily engineered to be longer or shorter depending on application. For instance, the Protein-G heterodimer could be used as a BITE scaffold and the linker optimized to maximize the functionality. Likewise, novel BITEs might be different combinations of bi-specific binders, for instance, A1-A1-HS-HS, A1-HS-A1-HS, A1-HS-HS-A1, etc.
Figure 14:
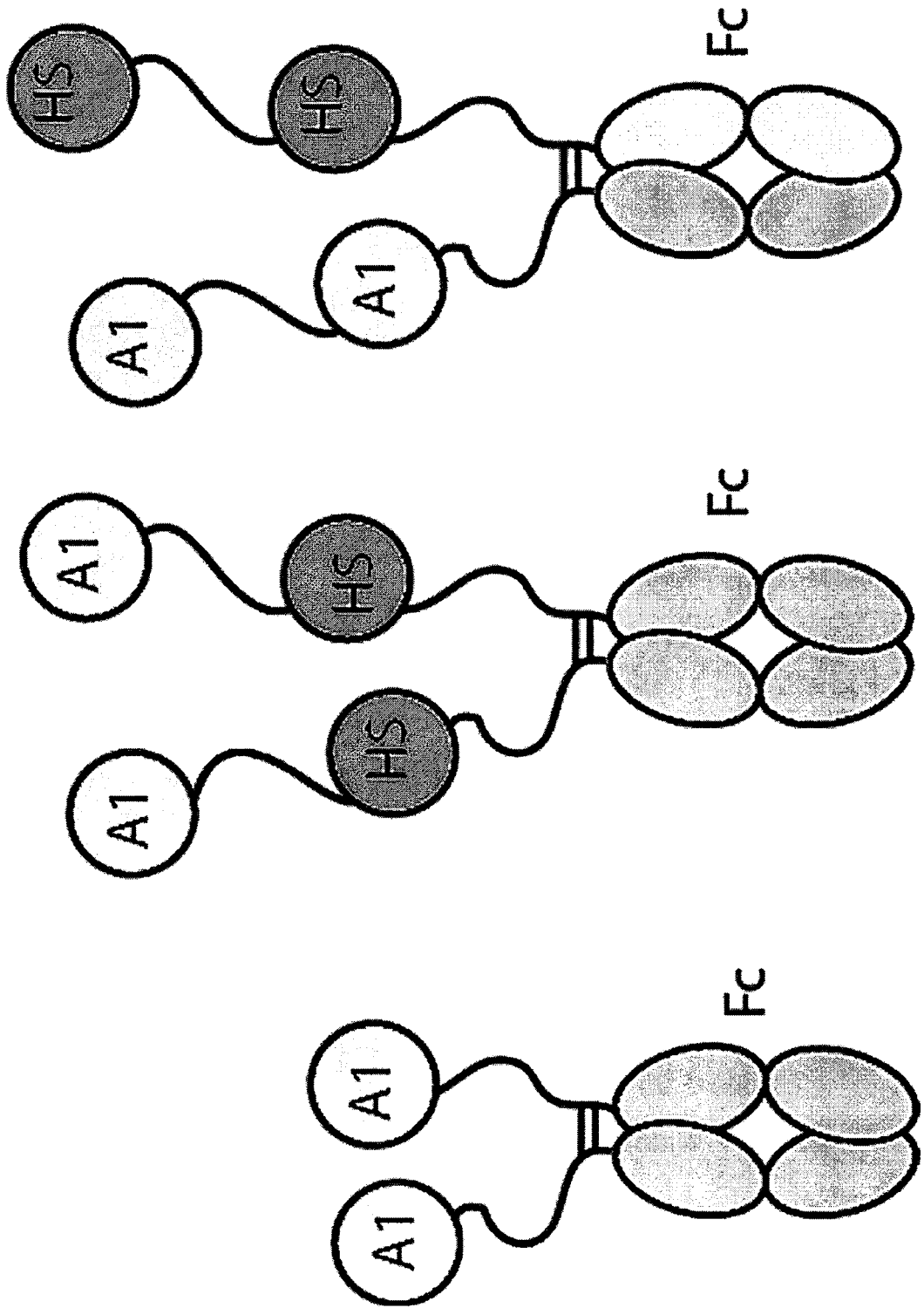
FIG. 14 shows exemplary embodiments of multimeric modules. Constructing Protein-G Fc fusions—This provides for combining the antibody activities associated with Fc binding (which there are many) into a fusion with multiple Protein-G modules. A wide range of different patterns can be constructed. There is currently no technology that has multiple bi-specific modules linked together with the Fc domain.

An area of active research in the biopharmaceutical industry is the engineering of bi-specific antibodies where the two Fab arms recognize different antigens (Speiss et al., 2015). This engineering involves introducing multiple mutations into the antibody scaffold and is costly and not optimally efficient. In this regard, Protein-G can be co-engineered with Fab fragments to produce molecules with multiple specificities with much more versatility than can be achieved using an antibody scaffold since many copies of the Fabs with different specificities can be linked together to combine the attributes of multi-specificity and valency in the same molecule (FIG. 13). A further functional advance could be to introduce these multi-valent/specificity Protein-G chains into Fc frameworks thereby producing an engineered IgG that has the ability to bind multiple copies of a desired Fab to enhance avidity over what is possible with just two Fab arms (FIG. 14). This concept can be extended by matching the Protein-G specificity to Fabs that recognize different binding partners thereby producing an IgG variant with multi-valent and bi-specific characteristics. Previously, no strategy had been proposed to enable facile control over both valency and specificity of multivalent antibody constructs.

Antibodies exploit multi-valency through naturally occurring formats including the IgG (bivalent), IgA (tetravalent) and IgM (decavalent). Here, the ability to simultaneously engage multiple binding sites through a single molecule enables the potential for enhanced affinity and activity. Synthetic antibody constructs are typically in the IgG format and further engineering to alter the Fab valency is generally difficult due to the complicated architecture of the IgG. Engineered Protein-G variants provide an alternative avenue for controlling multi-valency where the IBP can readily be produced in various oligomeric formats in high yield. Here, Protein-G can create large, controlled multi-valent constructs where Fabs are tethered through either non-covalent or covalent crosslinking Importantly, the Protein-G construct can be controlled in a highly facile manner through introduction of defined linker lengths and oligomeric formats (FIG. 13). Such constructs will be useful for the generation of high-capacity purification resin and the exploitation of antibody affinity and activity through multivalent affinity enhancement.

Here Applicants generated multivalent constructs through Golden Gate cloning where fragments are assembled through small, DNA overhangs created by type IIs restriction enzymes (enzymes which cut distal to the sequence they recognize). (Engler and Marillonnet. 2013). Through the generation of specific overhangs, one can rapidly assemble repetitive fragments of DNA, controlling valency, specificity and order of Protein-G molecules. Using this strategy, Applicants were able to generate Protein-G-A1 constructs ranging from a dimer to decamer using repeats of the $Gly_4Ser$ linker. These variants were readily purified to homogeneity using standard IMAC purification procedures. Notably, all variants expressed well (>5 mg/ml) in standard shake-flask expression methods. Importantly, this cloning method enables the linker length to be readily altered though modifying the fragments used for assembly. Given the high solubility of Protein-G there would be extreme flexibility in our choice of both linker length and composition.

E. Development of Bi-Specific Antibody Reagents Comprising Modified Protein G Fab Binding Domains Applicants hypothesized a bi-specific Protein-G construct comprised of modified protein G Fab binding domains with different isotype-specificities will enable the simultaneous engagement of two different protein antigens. To demonstrate the utility of such an approach, Applicants used ELISA where antigen 1 (yeast Anti-silencing factor 1) was immobilized on a Maxisorp plate coated with neutravidin. Subsequently, a mixture of Protein-G-A1-Protein-G-HS, $Fab_{Hs}$ (specific to yAsf1) and $Fab_K$ (specific to RNA-binding protein U1A) were added in stoichiometric amounts. After a period of incubation (~15 min) and washing, U1A was titrated at concentrations of 0-250 nM. Subsequent binding of U1A was detected by anti-FLAG-HRP which detected an epitope tag on U1A. The ELISA data demonstrate titratable, saturable binding of U1A only when all reagents are added to the ELISA well indicating the Protein-G-A1-Protein-G-HS fusion allows for the simultaneous engagement of multiple, specific binding partners. Such a reagent should enable the development of facile production of multivalent constructs for rapid assessment of multispecific affinity and activity enhancement.

Figures 5A, 5B, 5C:
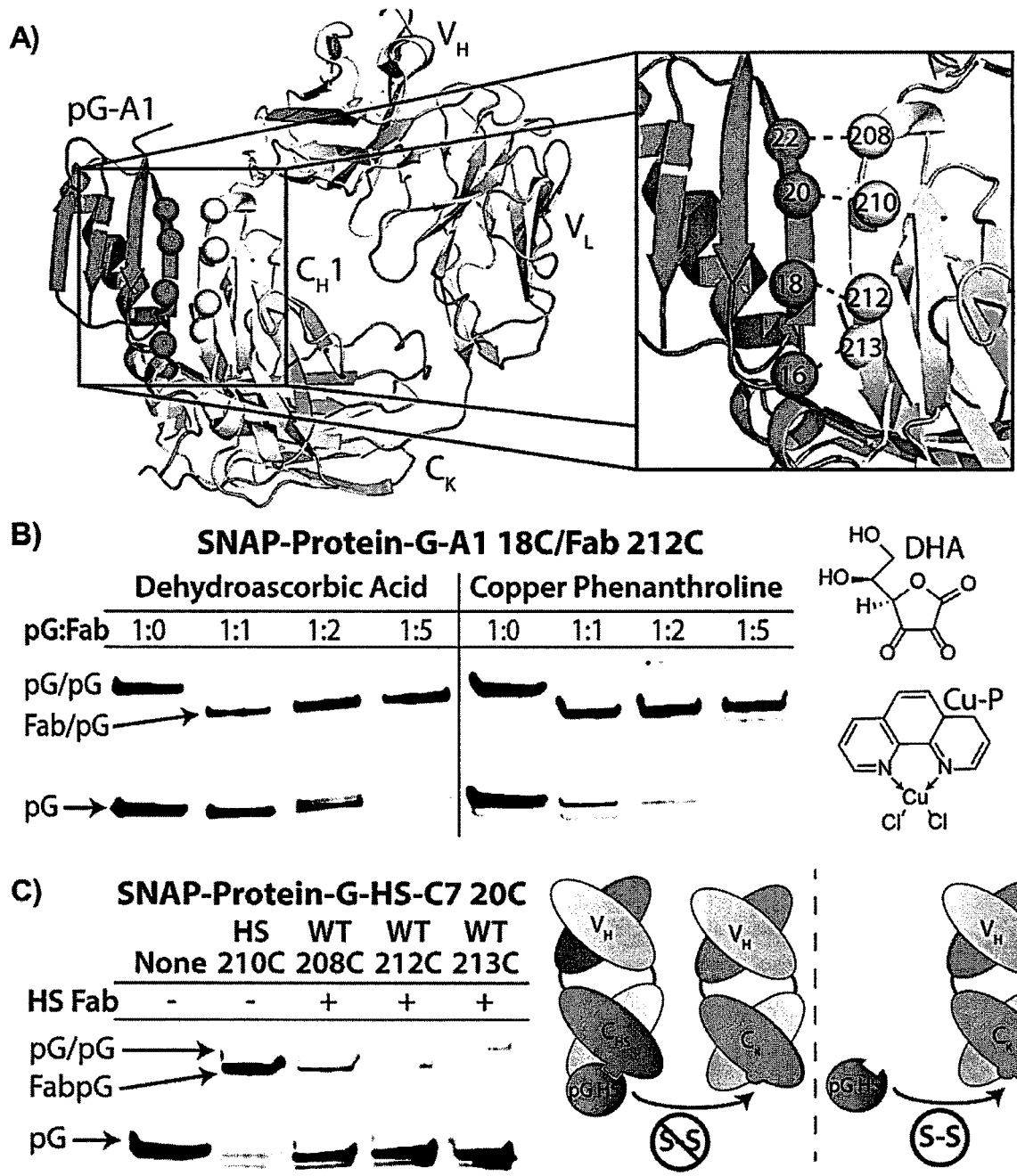
FIGS. 5A-5C—Covalent crosslinking of Fab-Protein-G. A) Schematic of Fab-Protein-G interaction. The antiparallel β-strand interaction reveals four positions within Protein-G and Fab to serve as sites for cysteine crosslinking to form covalent adducts. B) Oxidation strategies for covalent adduct formation. We identify copper phenanthroline as an efficient oxidation catalyst for Fab-Protein-G complex formation. Near quantitative crosslinking occurs in less than one hour. C) Crosslinking specificity. To further understand the requirements of specific, orthogonal crosslinking we tested the cross-reactivity of non-cognate Fab-Protein-G pairs. Here, the placement of the cysteine residues within the non-cognate Fab is critical to preventing off-target crosslinking. The combination of orthogonal light chain pairs coupled with altered cysteine crosslinking positions enable the generation of high-yield multi-specific affinity reagents.

F. Covalent Crosslinking of Polypeptides Comprising Modified Protein G Fab Binding Domains to Fabs:

While multivalent tethers of Protein-G enable the enhancement of affinity and activity, in some instances it may be desirable to create covalent constructs ensuring the stoichiometry of the complex. Inspection of the Protein-G-A1-Fab complex structure indicated several positions in these two molecules where introduction of cysteine residues might enable covalent crosslinking through the generation of disulfide bonds between Protein-G-A1 and the Fab. Here, several positions within the anti-parallel beta-strand interaction of the complex are within a feasible distance ($C\beta$-$C\beta$ distances ~5 Å) to enable covalent crosslinking. These pairs include: $Protein\text{-}G^{16}$ and $Fab_{CK}^{221}$, $Protein\text{-}G\text{-}A1^{18}$ and $Fab_{CK}^{220}$, $Protein\text{-}G^{20}$ and $Fab_{CK}^{218}$ and $Protein\text{-}G^{22}$ and $Fab_{CK}^{216}$. We tested all pairs through a series of oxidation strategies including spontaneous oxidation through air and chemical oxidants dehydroascorbic acid and copper-phenanthroline. All methods tested yielded cross-linked product with the $Protein\text{-}G\text{-}A1^{18}\text{-}Fab_{CL}^{220}$ and $Protein\text{-}G^{20}\text{-}Fab_{CL}^{218}$ pairs resulting in near stoichiometric crosslinking as determined by gel-shift assays (FIG. 5). Notably, minimal side reactions occurred when off-target crosslinking was allowed to occur. Here, mis-matched disulfide bonds failed to appreciably form when excess surface cysteine-free Fab was used as a competitor to block adventitious disulfide bond formation. The generation of covalent Fab-Protein-G constructs will enable the exploitation of Protein-G multivalent scaffolds when Fab and Protein G are at concentrations below that typically required to form appreciable complex (sub-nanomolar).

II. Fab Polypeptides

The Fab polypeptides of the disclosure may be an antibody or a fragment of an antibody comprising the Fab region. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof.

Fab polypeptides can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the animal's serum. Common variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants that promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA, 94:4937-4942; Hanes et al, (1998) Proc. Natl. Acad. Sci. USA 95:14130-14135); single cell antibody producing technologies (e.g., selected lymphocyte antibody method ("SLAM") (U.S. Pat. No. 5,627,052, Wen et al, (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al, (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody of this disclosure to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The Fab polypeptides of the disclosure also include derivatives that are modified by the covalent attachment of any type of molecule to the antibody such that covalent attachment does not prevent the antibody from generating an anti-idiotypic response. Antibody derivatives include, but are not limited to, Fab polypeptides that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide of this disclosure to provide transgenic plants and cultured plant cells (e.g., but not limited to tobacco, maize, and duckweed) that produce such Fab polypeptides, specified portions or variants in the plant parts or in cells cultured therefrom. For example, Cramer et al. (1999) Curr. Top. Microbiol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762 and 6,180, 370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse that has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al, (1995) Genomics 26:294-307; Jakobovits (1994) Current Biology 4(8):761-763; Arbones et al. (1994):Immunity 1(4): 247-260; Jakobovits (1993) Nature 362(6417):255-258; Jakobovits et al. (1993) Proc. Natl. Acad. Sci. USA 90(6): 2551-2555; and U.S. Pat. No. 6,075,181).

The antibodies of this disclosure also can be modified to create chimeric antibodies. Chimeric antibodies are those in which the various domains of the antibodies' heavy and light chains are coded for by DNA from more than one species. See, e.g., U.S. Pat. No. 4,816,567.

The antibodies of this disclosure can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

A. Purification Using Polypeptides with Modified Protein G Fab Binding Domain

Proteins-A and G are multi-specific proteins that are unique among the IBPs in their ability to bind to the Fc domain of the IgG, as well as the fragment antibody-binding (Fab) domain. The Fab domain is a critical portion of the antibody since it confers the antibody's antigen specificity and its binding capacity. Fab fragments are used in myriad applications and have advantages over traditional antibodies derived from animal sources because they can be generated by directed evolution processes providing for the introduction of customized properties.

Protein-G binds to the constant domain of the Fab portion of the IgG through its interaction with the $C_H1$ domain, a highly conserved domain across many isotypes and species. (Derrick and Wigley, 1992). Because Protein-G binds to a section of the Fab that is highly conserved across all antibodies, it has the potential to be a more effective affinity reagent than Protein-A. However, the low affinity of the natural domain ($K_D$~low µM) has thus far limited the usage of Protein-G as an affinity reagent compared to Protein-A (10 nM).

While Protein-A is the industry standard today, it is generally recognized that Fab antibody purification using Protein-A resin suffers from several technical issues. Methods to release efficiently the antibody from the Protein-A resin require wash steps at low pH (~pH 2). These conditions can have deleterious effects on the structural integrity of some antibodies, which can lead to loss of function. Also, at these pHs some a small fraction of the Protein-A can leech off the column and effectively contaminate the antibody sample being purified. Further, during expression in cell culture or bacteria, some antibodies can get proteolytically clipped making them less effective. These clips are mainly in the Fab $C_{H1}$ domain and thus, Protein-A binding cannot discriminate between the desired full-length form of the antibody and the degradation products. Removing these products requires a further ion-exchange purification step. Conversely, since Protein-G binds the Fab $C_{H1}$ domain, it can readily discriminate between the full-length unprocessed molecule from the degradation forms since it will only bind the unprocessed Fab. This results in a clean one-step purification process.

Figure 4A:
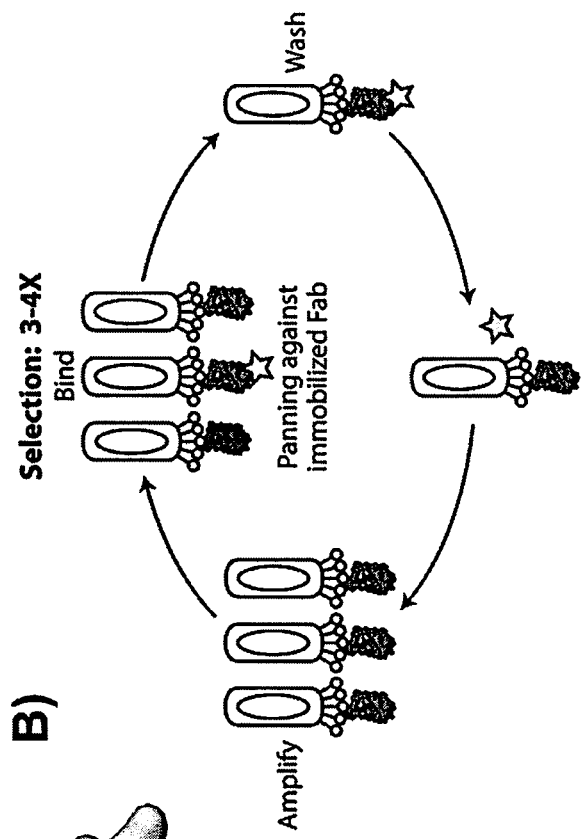
FIGS. 4A-4D—Protein-G-A1 helical-cap selection. A). Protein-G-A1 residues randomized for helical-cap library are represented as spheres. B). Phage display selection schematic. C). Unique Protein-G sequences of mutated residues derived from selection. Shown are SEQ ID NOS:18 and 20-26, respectively. D). ELISA signal of Protein-G-HS variant C7 binding to Fab-HS demonstrate isotype specificity.
Figure 4B:
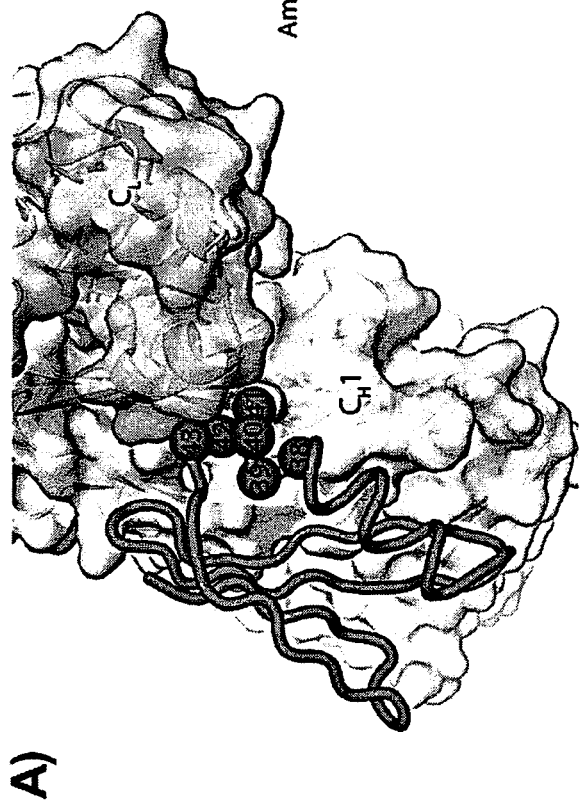

To exploit the potential advantages of Protein-G to make it practical for Fab antibody purification, increasing the affinity between these molecules by at least an order of magnitude is necessary. This is a challenge because the Fab-Protein-G interaction interface is quite small and is achieved through an anti-parallel beta strand association between Protein-G and $C_H1$ dominated by main chain interactions. To overcome such challenges, it is possible to increase binding affinities using phage display mutagenesis. This process is called affinity maturation. Phage display selections involve an iterative process whereby desired characteristics of the variant molecules are progressively enriched for. Phage display libraries containing $10^{10}$ different variants can be designed and produced that systematically introduce combinations of amino acids at selected positions in the molecule that are being affinity matured. The selection of the appropriate sites in Protein-G to affinity mature requires knowledge of contact interface with the Fab framework, which can be ascertained by X-ray crystal structure information (FIG. 4A). Importantly, since the conditions of the phage display selection process can be highly controlled, properties of the phage display binders can be manipulated by changing conditions like the concentration of the immobilized target to increase affinity or changes in buffer to select variants with binding properties that are affected by pH or different solvents, for instance (FIG. 4B).

III. Polypeptides of the Disclosure

Certain embodiments concern polypeptides, peptides, and proteins for use in various embodiments. In specific embodiments, all or part of the proteins of the disclosure can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference.

As used herein, a "protein" or "polypeptide" refers to a molecule comprising at least ten amino acid residues. In some embodiments, a wild-type version of a protein or polypeptide are employed, however, in many embodiments, a modified protein or polypeptide is employed. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

Alternatively, recombinant DNA technology may be employed wherein a nucleotide sequence which encodes a peptide of the disclosure is inserted into an expression vector, transformed or transfected into an appropriate host cell and cultivated under conditions suitable for expression.

One embodiment includes the use of gene transfer to cells, including microorganisms, for the production and/or presentation of polypeptides or peptides. The gene for the polypeptide or peptide of interest may be transferred into appropriate host cells followed by culture of cells under the appropriate conditions. The generation of recombinant expression vectors, and the elements included therein, are well known in the art and briefly discussed herein. Alternatively, the protein to be produced may be an endogenous protein normally synthesized by the cell that is isolated and purified. It is specifically contemplated that a polypeptide or antigenic fragment may be chemically synthesized or it may be recombinantly produced in a cell that is not the same type of cell in which the protein is produced naturally. It will be understood that the post-translational modifications may differ if a peptide or polypeptide is obtained from a cell different that a natural host cell that expresses the polypeptide.

Another embodiment uses autologous B lymphocyte cell lines, which are transfected with a viral vector that expresses an immunogen product, and more specifically, a protein having immunogenic activity. Other examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk−, hgprt− or aprt− cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Where a protein is specifically mentioned herein, it is preferably a reference to a recombinant protein or synthetic protein or optionally a protein in which any signal sequence has been removed. The protein may be produced by recombinant DNA techniques.

Also included in compositions and methods are fusion proteins composed of two or more protein G variants. Such fusion proteins may be recombinantly produced. The protein G variants described herein may also be fused to additional proteins such as purification tags, including, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, or CRM197.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino acid molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino acid molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be known to those of ordinary skill in the art.

Amino acid sequence variants of protein G Fab binding domains and other polypeptides of the invention can be substitutional, insertional, or deletion variants. A variation in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to wild-type. A variant can comprise an amino acid sequence that is at least 50%, 60%, 70%, 80%, or 90%, including all values and ranges there between, identical to any sequence provided or referenced herein, e.g., SEQ ID NO:1-10, 14-16, 20-49, 51-91. A variant can include 2, 3, 4, 5, 6, 7, 8, 9, 10, 11, 12, 13, 14, 15, 16, 17, 18, 19, 20, or more substitute amino acids.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptide or polypeptide described or referenced herein.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

IV. Detectable Labels

In some aspects of this disclosure, it will be useful to detectably or therapeutically label the Fab polypeptide or protein G variant. Methods for conjugating polypeptides to these agents are known in the art. For the purpose of illustration only, polypeptides can be labeled with a detectable moiety such as a radioactive atom, a chromophore, a fluorophore, or the like. Such labeled polypeptides can be used for diagnostic techniques, either in vivo, or in an isolated test sample or in methods described herein.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition that is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6.sup.th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6.sup.th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/polypeptides, e.g., rhodamine/anti-rhodamine, biotin/avidin and biotin/strepavidin.

The coupling of polypeptides to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten polypeptides. See, Harlow and Lane (1988) supra.

V. Nucleic Acids

In certain embodiments, the present disclosure concerns recombinant polynucleotides encoding the proteins, polypeptides, and peptides described herein.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of or of at least or at most: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges there between, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar.

The nucleic acid segments can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

Also contemplated is the use of polynucleotides which are complementary to all the above described polynucleotides.

A. Vectors

Polypeptides described herein may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a variant SpA polypeptide the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

B. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present disclosure to regulate the expression of a gene. Examples of such inducible elements, which are regions of a nucleic acid sequence that can be activated in response to a specific stimulus, include but are not limited to Immunoglobulin Heavy Chain, Immunoglobulin Light Chain, T Cell Receptor, HLA DQ and/or DQ, Interferon, Interleukin-2, Interleukin-2, MHC Class II, MHC Class II HLA-DR, Actin, Muscle Creatine Kinase (MCK), Prealbumin (Transthyretin), Elastase I, Metallothionein (MTII), Collagenase, Albumin, Fetoprotein, γ-Globin, Globin, c-fos, c-Ha-Ras, Insulin, Neural Cell Adhesion Molecule (NCAM), 1-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Retroviruses, Papilloma Virus, Hepatitis B Virus, Human Immunodeficiency Virus, Cytomegalovirus (CMV) IE, Gibbon Ape Leukemia Virus.

Inducible elements include, but are not limited to MT II—Phorbol Ester (TFA)/Heavy metals; MMTV (mouse mammary tumor virus)—Glucocorticoids; Interferon-poly (rI)x/poly(rc); Adenovirus 5 E2—EIA; Collagenase—Phorbol Ester (TPA); Stromelysin-Phorbol Ester (TPA); SV40—Phorbol Ester (TPA); Murine MX Gene—Interferon, Newcastle Disease Virus; GRP78 Gene—A23187; 2-Macroglobulin—IL-6; Vimentin—Serum; MHC Class I Gene H-2b—Interferon; HSP70—EIA/SV40 Large T Antigen; Proliferin—Phorbol Ester/TPA; Tumor Necrosis Factor—PMA.

The particular promoter that is employed to control the expression of peptide or protein encoding polynucleotide of the disclosure is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In embodiments in which a vector is administered to a subject for expression of the protein, it is contemplated that a desirable promoter for use with the vector is one that is not down-regulated by cytokines or one that is strong enough that even if down-regulated, it produces an effective amount of a saeRS-regulated protein for eliciting an immune response. Non-limiting examples of these are CMV IE and RSV LTR. Tissue specific promoters can be used, particularly if expression is in cells in which expression of an antigen is desirable, such as dendritic cells or macrophages. The mammalian MHC I and MHC II promoters are examples of such tissue-specific promoters.

C. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments, the use of internal ribosome entry sites (IRES) elements are used to create multigene, or polycistronic, messages. IRES elements are able to bypass the ribosome scanning model of 5'methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

D. Selectable and Screenable Markers

In certain embodiments, cells containing a nucleic acid construct of the disclosure may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

E. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

F. Expression Systems

Numerous expression systems exist that comprise at least a part or all of the compositions discussed above. Prokaryote- and/or eukaryote-based systems can be employed for use to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

VI. Sequences

SEQ ID NO:1 corresponds to the wild-type protein G from *Streptococcus* or a portion of the wild-type protein G from *Streptococcus*. The C domains/Fab-binding regions of protein G are exemplified in the underlined portions shown below.

```
                                                 (SEQ ID NO: 1)
EFNKYGVSDYYKNLINNAKTVEGVKDLQAQVVESAKKARISEATDGLSDF

LKSQTPAEDTVKSIELAEAKVLANRELDKYGVSDYHKNLINNAKTVEGVK

DLQAQVVESAKKARISEATDGLSDFLKSQTPAEDTVKSIELAEAKVLANR

ELDKYGVSDYYKNLINNAKTVEGVKALIDEILAALPKTDTYKLILNGKTL

KGETTTEAVDAATAEKVFKQYANDNGVDGEWTYDDATKTFTVTEKPEVID

ASELTPAVTTYKLVINGKTLKGETTTEAVDAATAEKVFKQYANDNGVDGE

WTYDDATKTFTVTEKPEVIDASELTPAVTTYKLVINGKTLKGETTTKAVD

AETAEKAFKQYANDNGVDGVWTYDDATKTFTVTEMVTEVPGDAPTEPEKP

EASIPLVPLTPATPIAKDDAKKDDTKKEDAKKPEAKKEDAKKAETLPTTG

EGSNPFFTAAALAVMAGAGALAVASKRKED
```

SEQ ID NO:2 refers to a modified protein G Fab-binding region:
$X_{15}TX_{17}X_{18}X_{19}X_{20}X_{21}X_{22}TX_{24}X_4X_{37}X_{38}AX_{40}X_{41}X_{42}X_{43}$ (SEQ ID NO:2); wherein $X_{15}$ is K, R, E, or I; $X_{17}$ is L, F, or A; $X_{18}$ is K, S, W, R, or T; $X_{19}$ is G or Y; $X_{20}$ is E, Y, A, or H; $X_{21}$ is T or R; $X_{22}$ is T, S, A, or G; $X_{24}$ is E, K, T, or Q; $X_{37}$ is Q or R; $X_{38}$ is Y, I, or F; $X_{40}$ is N, Y, F, H, K, or W; $X_{41}$ is D, V, or E; $X_{42}$ is N, H, Q, or Y; $X_{43}$ is G, E, D, or P; and $X_4$ is an amino acid sequence that is 5 to 20 amino acids in length In some embodiments, the modified protein G Fab-binding region comprises one of SEQ ID NO:3-10:

```
KTLKGETTTKAVDAATAEKVFKQYANDNG   (WT  - SEQ ID NO: 19)

RTLSGYTTTTAVDAATAEKVFKQYAYVHE   (A1  - SEQ ID NO: 3);

KTFWGETTTKAVDAATAEKVFKQYAFDND   (A3  - SEQ ID NO: 4);

ETLRYETSTKAVDAATAEKVFKQIAHDQG   (A12 - SEQ ID NO: 5);

KTLKGETTTKAVDAATAEKVFKQYAYVHD   (B9  - SEQ ID NO: 6);

ETLRYETSTKAVDAATAEKVFKRIAHDQG   (F5  - SEQ ID NO: 7);

KTASGARATKAVDAATAEKVFKQYAKEYP   (G11 - SEQ ID NO: 8);

ETLTGETGTQAVDAATAEKVFKQYAWVND   (H11 - SEQ ID NO: 9);

ITLKGHTTTKAVDAATAEKVFKQYAWVND
(H12 - SEQ ID NO: 10).
```

Exemplary linkers disclosed herein include: GGGS (SEQ ID NO:11); GGGSGGGSGGGS (SEQ ID NO:12); LAAA (SEQ ID NO:94); LGGGGSGGGGSGGGGSAAA (SEQ ID NO:95) or LSGGGGSGGGGSGGGGSGGGGSAAA (SEQ ID NO:96); a helical linker such as LAEAAAKEAAA-KAAA SEQ ID NO:97), LAEAAAKEAAAKEAAAKAAA (SEQ ID NO:98), LAEAAAKEAAAKEAAAKEAAA-KAAA (SEQ ID NO:99), or LAE-AAAKEAAAKEAAAKEAAAKEAAAKAAA (SEQ ID NO:100).

A further embodiment of a modified protein G Fab binding region is: LTPAVTTYKLVINGKTLKGETTTKAV-DAETAEKAFKQYANDNE (SEQ ID NO:13).

In some aspects, the unmodified protein G is SEQ ID NO:14:

```
                                         (SEQ ID NO: 14)
MEKEKKVKYFLRKSAFGLASVSAAFLVGSTVFAVDSPIEDTPIIRNGGEL

TNLLGNSETTLALRNEESATADLTAAAVADTVAAAAAENAGAAAWEAAAA

ADALAKAKADALKEFNKYGVSDYYKNLINNAKTVEGVKDLQAQVVESAKK

ARISEATDGLSDFLKSQTPAEDTVKSIELAEAKVLANRELDKYGVSDYHK

NLINNAKTVEGVKDLQAQVVESAKKARISEATDGLSDFLKSQTPAEDTVK

SIELAEAKVLANRELDKYGVSDYYKNLINNAKTVEGVKALIDEILAALPK

TDTYKLILNGKTLKGETTTEAVDAATAEKVFKQYANDNGVDGEWTYDDAT

KTFTVTEKPEVIDASELTPAVTTYKLVINGKTLKGETTTEAVDAATAEKV

FKQYANDNGVDGEWTYDDATKTFTVTEKPEVIDASELTPAVTTYKLVING

KTLKGETTTKAVDAETAEKAFKQYANDNGVDGVWTYDDATKTFTVTEMVT

EVPGDAPTEPEKPEASIPLVPLTPATPIAKDDAKKDDTKKEDAKKPEAKK

EDAKKAETLPTTGEGSNPFFTAAALAVMAGAGALAVASKRKED.
```

In further embodiments, the unmodified protein G is represented by SEQ ID NO:15:

```
                                         (SEQ ID NO: 15)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTYKLVINGRTLSGETTTKAV

DAETAEKAFKQYANDNGVDGVWTYDDATKTFTVTE.
```

The unmodified Fab-binding regions/C regions are underlined in the sequences above. In some embodiments, the unmodified Fab-binding region comprises the sequence: KTLKGETTTKAVDAATAEKVFKQYANDNG (SEQ ID NO:19), KTLKGETTTEAVDAATAEKVFKQYANDNG (SEQ ID NO:92), or KTLKGETTTKAVDAETAEKAF-KQYANDNG (SEQ ID NO:93).

In some embodiments, the Fab binding region (C domain segment) comprises a.a. 56-120 of SEQ ID NO:15:

```
                                         (SEQ ID NO: 16)
LTPAVTTYKLVINGKTLKGETTTKAVDAATAEKVFKQYANDNGVDGEWTY

DDATKTFTVTEKPEVI
```

In some embodiments, the immunogenicity region comprises a.a. 133-143 of SEQ ID NO:15: KLVINGRTLSG (SEQ ID NO:17)

In some embodiments, the isotype recognition region comprises a.a. 162-167 of SEQ ID NO:15: YANDNG (SEQ ID NO:18)

Variant isotype recognition regions include: YAYVHE (Protein-G-HS A1, SEQ ID NO:20); YSRPHV (Protein-G-HS C6, SEQ ID NO:21); YAVGAV (Protein-G-HS C7, SEQ ID NO:22); YAAPHV (Protein-G-HS D2, SEQ ID NO:23); YSHPHV (Protein-G-HS E3, SEQ ID NO:24); CTVWPV (Protein-G-HS F1, SEQ ID NO:25); YAFAHV (Protein-G-HS H10, SEQ ID NO:26).

WT immunogenicity region includes: LVINGRTLSG (WT, SEQ ID NO:50); variant immunogenicity regions include: LVIRGLTLSL (B11, SEQ ID NO:27); LVIR-GLTLSF (B12, SEQ ID NO:28); LVIGGLRLWF (B5, SEQ ID NO:29); LVIRGVTLLF (B6, SEQ ID NO:30); LVIR-GITLGF (B7, SEQ ID NO:31); LVIMGSTLSL (B8, SEQ ID NO:32); LVIIGRTLSL (B9, SEQ ID NO:33); LVISGITLSF (B10, SEQ ID NO:34); LVIGGRTLSF (A11, SEQ ID NO:35); LVIGGRTLSF (A12, SEQ ID NO:36); LVISGSTLSL (B1, SEQ ID NO:37); LVILGRTLSV (B2, SEQ ID NO:38); FVIRGRTLSF (B3, SEQ ID NO:39); LVISGRTLSL (B4, SEQ ID NO:40); LVIGGRTLRF (A8, SEQ ID NO:41); LVIRGVTLGF (A9, SEQ ID NO:42); LVIRGRTLSL (A10, SEQ ID NO:43); LVIGGRTLRF (A1, SEQ ID NO:44); LVIGGRTLSF (A2, SEQ ID NO:45); LVISGLTLSF (A3, SEQ ID NO:46); LVIGGVTLSF (A4, SEQ ID NO:47); LVIRGVTLSL (A5, SEQ ID NO:48); and LVIGGITLSF (A6, SEQ ID NO:49).

In some embodiments, the variant immunogenicity region is at least 80% homologous or identical to $X_2'VIX_5'GX_7'X_8'LX_{10}'X_{11}'$ (SEQ ID NO:101), wherein $X_2'$ is L or F; $X_5'$ is N, R, G, M, I, S, or L; $X_7'$ is R, L, V, I, or S; X8' is T or R; X10' is S, W, L, G, or R; X11' is L, F, or V; and wherein the variant immunogenicity region is not LVINGRTLSG (SEQ ID NO:50).

$X_A$=AVDAATAEKVFK (SEQ ID NO:51);
$X_B$=LTPAVTTYKLVING (SEQ ID NO:52);
$X_C$=VDGEWTYDDATKTFTVTEKPEVI (SEQ ID NO:53).

Sequences 54-91 are exemplary polypeptide embodiments of the disclosure:

Protein-G-A1:
```
                                         (SEQ ID NO: 54)
MKGETTTEAVDAATAEKVFKQYANDNGVDGEWTYDDATKTFTVTEKPEVI

DASELTPAVTTYKLVINGRTLSGYTTTTAVDAATAEKVFKQYAYVHEVDG

EWTYDDATKTFTVTEKPEVIDASELTPAVTTYKLVINGRTLSGETTTKAV

DAETAEKAFKQYANDNGVDGVWTYDDATKTFTVTE
```

Protein-G-A3:
```
                                         (SEQ ID NO: 55)
MKGETTTEAVDAATAEKVFKQYANDNGVDGEWTYDDATKTFTVTEKPEVI

DASELTPAVTTYKLVINGKTFWGETTTKAVDAATAEKVFKQYAFDNDVDG

EWTYDDATKTFTVTEKPEVIDASELTPAVTTYKLVINGRTLSGETTTKAV

DAETAEKAFKQYANDNGVDGVWTYDDATKTFTVTE
```

Protein-G-A12:
```
                                         (SEQ ID NO: 56)
MKGETTTEAVDAATAEKVFKQYANDNGVDGEWTYDDATKTFTVTEKPEVI

DASELTPAVTTYKLVINGETLRYETSTKAVDAATAEKVFKQIAHDQGVDG

EWTYDDATKTFTVTEKPEVIDASELTPAVTTYKLVINGRTLSGETTTKAV
```

-continued
DAETAEKAFKQYANDNGVDGVWTYDDATKTFTVTE

Protein-G-B9:
(SEQ ID NO: 57)
MKGETTTEAVDAATAEKVFKQYANDNGVDGEWTYDDATKTFTVTEKPEVI DASEL<u>TPAVTTYKLVINGKTLKGETTTKAVDAATAEKVFKQYAYVHDVDG</u>

<u>EWTYDDATKTFTVTEKPEV</u>IDASELTPAVTTYKLVINGRTLSGETTTKAV

DAETAEKAFKQYANDNGVDGVWTYDDATKTFTVTE

Protein-G-F5:
(SEQ ID NO: 58)
MKGETTTEAVDAATAEKVFKQYANDNGVDGEWTYDDATKTFTVTEKPEVI DASEL<u>TPAVTTYKLVINGETLRYETSTKAVDAATAEKVFKRIAHDQGVDG</u>

<u>EWTYDDATKTFTVTEKPEV</u>IDASELTPAVTTYKLVINGRTLSGETTTKAV

DAETAEKAFKQYANDNGVDGVWTYDDATKTFTVTE

Protein-G-G11:
(SEQ ID NO: 59)
MKGETTTEAVDAATAEKVFKQYANDNGVDGEWTYDDATKTFTVTEKPEVI DASEL<u>TPAVTTYKLVINGKTASGARATKAVDAATAEKVFKQYAKEYPVDG</u>

<u>EWTYDDATKTFTVTEKPEV</u>IDASELTPAVTTYKLVINGRTLSGETTTKAV

DAETAEKAFKQYANDNGVDGVWTYDDATKTFTVTE

Protein-G-H11:
(SEQ ID NO: 60)
MKGETTTEAVDAATAEKVFKQYANDNGVDGEWTYDDATKTFTVTEKPEVI DASEL<u>TPAVTTYKLVINGETLTGETGTQAVDAATAEKVFKQYAWVNDVDG</u>

<u>EWTYDDATKTFTVTEKPEV</u>IDASELTPAVTTYKLVINGRTLSGETTTKAV

DAETAEKAFKQYANDNGVDGVWTYDDATKTFTVTE

Protein-G-H12:
(SEQ ID NO: 61)
MKGETTTEAVDAATAEKVFKQYANDNGVDGEWTYDDATKTFTVTEKPEVI DASEL<u>TPAVTTYKLVINGITLKGHTTTKAVDAATAEKVFKQYAWVNDVDG</u>

<u>EWTYDDATKTFTVTEKPEV</u>IDASELTPAVTTYKLVINGRTLSGETTTKAV

DAETAEKAFKQYANDNGVDGVWTYDDATKTFTVTE

Protein G Sequences that demonstrate isotype specificity.

Protein-G-HS A1:
(SEQ ID NO: 62)
MKGETTTEAVDAATAEKVFKQYANDNGVDGEWTYDDATKTFTVTEKPEVI

DASELTPAVTTYKLVINGKTLKGETTTEAVDAATAEKVFKQYANDNGVDG

EWTYDDATKTFTVTEKPEVIDASELTPAVTTYKLVINGRTLSGETTTKAV

DAETAEKAFKQ<u>YAYVHE</u>VDGVWTYDDATKTFTVTE

Protein-G-HS C6:
(SEQ ID NO: 63)
MKGETTTEAVDAATAEKVFKQYANDNGVDGEWTYDDATKTFTVTEKPEVI

DASELTPAVTTYKLVINGKTLKGETTTEAVDAATAEKVFKQYANDNGVDG

EWTYDDATKTFTVTEKPEVIDASELTPAVTTYKLVINGRTLSGETTTKAV

DAETAEKAFKQ<u>YSRPHV</u>VDGVWTYDDATKTFTVTE

Protein-G-HS C7:
(SEQ ID NO: 64)
MKGETTTEAVDAATAEKVFKQYANDNGVDGEWTYDDATKTFTVTEKPEVI

DASELTPAVTTYKLVINGKTLKGETTTEAVDAATAEKVFKQYANDNGVDG

EWTYDDATKTFTVTEKPEVIDASELTPAVTTYKLVINGRTLSGETTTKAV

DAETAEKAFKQ<u>YAYGAV</u>VDGVWTYDDATKTFTVTE

Protein-G-HS D2:
(SEQ ID NO: 65)
MKGETTTEAVDAATAEKVFKQYANDNGVDGEWTYDDATKTFTVTEKPEVI

DASELTPAVTTYKLVINGKTLKGETTTEAVDAATAEKVFKQYANDNGVDG

EWTYDDATKTFTVTEKPEVIDASELTPAVTTYKLVINGRTLSGETTTKAV

DAETAEKAFKQ<u>YAAPHV</u>VDGVWTYDDATKTFTVTE

Protein-G-HS E3:
(SEQ ID NO: 66)
MKGETTTEAVDAATAEKVFKQYANDNGVDGEWTYDDATKTFTVTEKPEVI

DASELTPAVTTYKLVINGKTLKGETTTEAVDAATAEKVFKQYANDNGVDG

EWTYDDATKTFTVTEKPEVIDASELTPAVTTYKLVINGRTLSGETTTKAV

DAETAEKAFKQ<u>YSHPHV</u>VDGVWTYDDATKTFTVTE

Protein-G-HS F1:
(SEQ ID NO: 67)
MKGETTTEAVDAATAEKVFKQYANDNGVDGEWTYDDATKTFTVTEKPEVI

DASELTPAVTTYKLVINGKTLKGETTTEAVDAATAEKVFKQYANDNGVDG

EWTYDDATKTFTVTEKPEVIDASELTPAVTTYKLVINGRTLSGETTTKAV

DAETAEKAFKQ<u>CTVWPV</u>VDGVWTYDDATKTFTVTE

Protein-G-HS H10:
(SEQ ID NO: 68)
MKGETTTEAVDAATAEKVFKQYANDNGVDGEWTYDDATKTFTVTEKPEVI

DASELTPAVTTYKLVINGKTLKGETTTEAVDAATAEKVFKQYANDNGVDG

EWTYDDATKTFTVTEKPEVIDASELTPAVTTYKLVINGRTLSGETTTKAV

DAETAEKAFKQ<u>YAFAHV</u>VDGVWTYDDATKTFTVTE

Immunogenicity

B11:
(SEQ ID NO: 69)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTY<u>KLVIRGLTLSL</u>ETTTKAV

DAETAEKAFKQYANDNGVDGVWTYDDATKTFTVTE

B12:
(SEQ ID NO: 70)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTY<u>KLVIRGLTLSF</u>ETTTKAV

DAETAEKAFKQYANDNGVDGVWTYDDATKTFTVTE

B5:
(SEQ ID NO: 71)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTY<u>KLVIGGLRLWF</u>ETTTKAV

DAETAEKAFKQYANDNGVDGVWTYDDATKTFTVTE

B6:
(SEQ ID NO: 72)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIRGVTLLFETTTKAV
DAETAEKAFKQYANDNGVDGVWTYDDATKTFTVTE

B7:
(SEQ ID NO: 73)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIRGITLGFETTTKAV
DAETAEKAFKQYANDNGVDGVWTYDDATKTFTVTE

B8:
(SEQ ID NO: 74)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIMGSTLSLETTTKAV
DAETAEKAFKQYANDNGVDGVWTYDDATKTFTVTE

B9:
(SEQ ID NO: 75)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIIGRTLSLETTTKAV
DAETAEKAFKQYANDNGVDGVWTYDDATKTFTVTE

B10:
(SEQ ID NO: 76)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVISGITLSFETTTKAV
DAETAEKAFKQYANDNGVDGVWTYDDATKTFTVTE

A11:
(SEQ ID NO: 77)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIGGRTLSFETTTKAV
DAETAEKAFKQYANDNGVDGVWTYDDATKTFTVTE

A12:
(SEQ ID NO: 78)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIGGRTLSFETTTKAV
DAETAEKAFKQYANDNGVDGVWTYDDATKTFTVTE

B1:
(SEQ ID NO: 79)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVISGSTLSLETTTKAV
DAETAEKAFKQYANDNGVDGVWTYDDATKTFTVTE

B2:
(SEQ ID NO: 80)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVILGRTLSVETTTKAV
DAETAEKAFKQYANDNGVDGVWTYDDATKTFTVTE

B3:
(SEQ ID NO: 81)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKFVIRGRTLSFETTTKAV
DAETAEKAFKQYANDNGVDGVWTYDDATKTFTVTE

B4:
(SEQ ID NO: 82)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVISGRTLSLETTTKAV
DAETAEKAFKQYANDNGVDGVWTYDDATKTFTVTE

A8:
(SEQ ID NO: 83)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIGGRTLRFETTTKAV
DAETAEKAFKQYANDNGVDGVWTYDDATKTFTVTE

A9:
(SEQ ID NO: 84)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIRGVTLGFETTTKAV
DAETAEKAFKQYANDNGVDGVWTYDDATKTFTVTE

A10:
(SEQ ID NO: 85)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIRGRTLSLETTTKAV
DAETAEKAFKQYANDNGVDGVWTYDDATKTFTVTE

A1:
(SEQ ID NO: 86)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIGGRTLRFETTTKAV
DAETAEKAFKQYANDNGVDGVWTYDDATKTFTVTE

A2:
(SEQ ID NO: 87)
MKGETTTEAVDAATAEKVFKQYANDNGVDGEWTYDDATKTFTVTEKPEVI
DASELTPAVTTYKLVINGKTLKGETTTKAVDAATAEKVFKQYANDNGVDG
EWTYDDATKTFTVTEKPEVIDASELTPAVTTYKLVIGGRTLSFETTTKAV
DAETAEKAFKQYANDNGVDGVWTYDDATKTFTVTE

-continued

A3:
(SEQ ID NO: 88)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTY<u>KLVISGLTLSF</u>ETTTKAV

DAETAEKAFKQYANDNGVDGVWTYDDATKTFTVTE

A4:
(SEQ ID NO: 89)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTY<u>KLVIGGVTLSF</u>ETTTKAV

DAETAEKAFKQYANDNGVDGVWTYDDATKTFTVTE

A5:
(SEQ ID NO: 90)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTY<u>KLVIRGVTLSL</u>ETTTKAV

DAETAEKAFKQYANDNGVDGVWTYDDATKTFTVTE

A6:
(SEQ ID NO: 91)
MKGETTTEAVDAATAEKVFKQYANDNGVDGEWTYDDATKTFTVTEKPEVI

DASELTPAVTTYKLVINGKTLKGETTTKAVDAATAEKVFKQYANDNGVDG

EWTYDDATKTFTVTEKPEVIDASELTPAVTTY<u>KLVIGGITLSF</u>ETTTKAV

DAETAEKAFKQYANDNGVDGVWTYDDATKTFTVTE.

Modified light chain constant region HS—a light chain HS constant region, which is a human 4D5 scaffold with residues PEELRTNK (SEQ ID NO:102; FIG. 11C) replacing light chain positions 122-129.

VII. Examples

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. In the examples and throughout the disclosure, Protein-G variants are polypeptides comprising a Fab-binding region.

Example 1—Construction of Polypeptides Comprising Modified Protein G FAB Binding Domains Immunoglobulin binding proteins (IBP) are broadly used as reagents for the purification and detection of antibodies. The C2 domain (i.e. Fab binding domain/region) of protein-G from *Streptococcus* is a multi-specific protein domain; it possesses a high affinity (KD~10 nM) for the Fc region of the IgG, but a much lower affinity (KD~low μM) for the CH1 of the antibody fragment (Fab). Here we describe the engineering of the protein-G interface using phage display to create an affinity matured reagent capable of robust binding to Fab fragments for numerous applications. Furthermore, we isolated a variant with pH-dependent affinity, enabling facile control of the protein-G-Fab interaction. Additional rational mutagenesis endowed protein-G with significantly enhanced base stability relative to the parent domain while maintaining high affinity to the Fab. The affinity-matured Protein-G variants were tethered together to produce multidimers capable of providing multivalent affinity enhancement to a low affinity antibody fragment-antigen interaction. Additionally, protein-G and the Fab framework were engineered to produce multispecific constructs that both exploit the avidity effects produced by tethering, as well as binding to multiple antigen types. Engineered protein-G variants would find widespread application in the use of Fab-based affinity reagents.

Immunoglobulin binding proteins (IBP's) have become indispensible reagents in the purification and detection of antibodies. Protein-G from Groups C and G *streptococcus* is a multi-domain cell surface protein possessing albumin and immunoglobulin binding domains and its ability to bind the predominant serum proteins is thought to enable the organism to evade detection by the host immune system. Protein G is one of a number of convergently evolved bacterial proteins capable of binding immunoglobulins including protein A from *Stahpylococcus*, Protein L from *Peptostreptococcus magnus* (Nilson et al., 1992) and protein M from *Mycoplasma* (Grover et al., 2014). Since their discovery, IBP's have been critical to the advancement of antibodies in research, diagnostics and therapeutics.

While IBP's have become the industry standard for immunoglobulin purification, numerous antibody formats create a demand for more customized purification reagents. Over the last two decades, phage display derived antibodies have become a more versatile alternative to hybridoma-based technology (Michnick and Sidhu, 2008). The completely in vitro process offers a number of technical advantages over traditional methods including exquisite control of bio-panning conditions and the ability to raise antibodies against highly conserved epitopes (Bradbury et al., 2011). Indeed, the promise of such technology is the basis for a number of large-scale efforts to obtain affinity reagents on the proteome scale (Colwill et al., 2011; Taussig et al., 2007). Our laboratory and others have helped develop synthetic antibody libraries based on "restricted chemical diversity" where residues within the CDRs of the antibody fragment are enriched in amino acids typically found at the antibody paratope, including tyrosine, serine and glycine (Fellouse et al., 2007; Miller et al., 2012). Such libraries, based on the 4D5 scaffold, have successfully produced affinity reagents to a wide range of targets (Fellouse et al., 2007; Rizk et al., 2011; Uysal et al., 2009; Ye et al., 2008). Furthermore, antibody fragments derived from synthetic libraries allow for the potential to move beyond the IgG format, enabling facile prokaryotic expression and further functionalization through genetic manipulation. One of the major bottlenecks in the large-scale generation and characterization of affinity reagents is their expression and purification for subsequent biophysical, structural and cell-based studies. Here, researchers select reagents based on their ability to bind the antigen binding fragment rather than the Fc.

Immunoglobulin binding proteins interact with a number of distinct epitopes on the full-length antibody. The ability to recognize conserved regions of the IgG scaffold enable IBP's to bind to antibodies from a wide range of species. Protein L binds to $V_L$ of kappa light chains ($K_D$~100 nM) (Graille et al., 2001)(FIG. 6A). The recently discovered protein M interacts through conserved framework regions on $V_L$ and $V_K$ and binds both isotypes with high affinity (low nM). Proteins A and G are multi-specific proteins possessing binding affinity to the IgG as well as the Fab portion of the antibody. Each binds to the hinge region connecting $C_H2$ and $C_H3$ on the Fc portion of the IgG with high affinity (~10 nM). Additionally, Protein A binds to the $V_H3$ subset of $V_H$ domains which comprises ~30-50% of the circulating IgG's ($K_D$~20 nM)(Graille et al., 2000). Protein G binds to the constant domain of the Fab portion of the IgG through its interaction with the $C_H1$ domain, a highly conserved domain across many isotypes and species (Derrick and Wigley, 1992). The inherent cross-reactivity of the Fab-protein G interaction is achieved through an anti-parallel beta strand association between protein G and $C_H1$ dominated by main chain interactions (Derrick and Wigley, 1992). However, the low affinity of the natural domain ($K_D$~low µM) limits the usage of protein G as an affinity reagent compared to protein A, for instance. Indeed, the low affinity of the protein G-Fab interaction has been exploited to separate antibody fragments based on valency (Proudfoot et al., 1992). As a result, typical purification strategies in our laboratory include initial purification with protein A, followed by cation-exchange to remove antibody variable domain degradation products that are retained in the initial purification step. In an effort to enable single step purification of Fabs, we have engineered the immunoglobulin domain from *Streptococcus* protein-G for improved binding to the 4D5 scaffold possessing a human IgG1 $C_H1$ and a Kappa light chain. Through a combined combinatorial and rational approach, we have endowed this domain with ~100-fold improved affinity, pH dependence and improved biophysical properties for use as an affinity reagent.

A. Experimental Procedures

1. Molecular Biology

The gene encoding the modified C2 domain of Protein-G was synthesized by GenScript. Subsequently, the gene was amplified and ligated into a phagemid pC3DsbA (Bailey and Kossiakoff, manuscript in preparation), between a DsbA signal sequence and the C-terminal domain of phage protein pIII under the control of the phoA promoter. Control phage ELISA experiments revealed robust display of Protein-G through its interaction with the 4D5 Fab scaffold.

2. Library Creation

To generate the phage library, the library construction strategy described in Sidhu et. al (Sidhu et al., 2000) was used. Briefly, through inspection of the crystal structure of the Protein-G-Fab complex (Protein Data bank entry1IGC) 15 residues in Protein-G were identified that were within 5 Å of the complex interface (FIG. 6B). These residues were randomized using the soft randomization strategy where at each position within the randomized codon, the wild type nucleotide was present at 70% and the remaining three nucleotides were present at 10%. Randomized primers were phosphorylated and used to anneal to prepared ssDNA of pC3DsbA to replace stop codons within each of the randomized regions of the single-stranded template. Double-stranded DNA was synthesized using the Kunkel protocol (Kunkel, 1985). A small number of library variants were sequenced to confirm >80% of the library had the desired diversity incorporated. The phage library was generated through electroporation of SS3320 cells (Sidhu et al., 2000). Recovered cells were infected with M13K07 helper phage and allowed to amplify overnight at 37° C. Phage particles were isolated through PEG precipitation for subsequent selection.

3. Selection Strategy

The first round of selection was performed with 1 mL of phage library re-suspended in TBST-0.5% BSA (~1×10$^{12}$ cfu). This was incubated with streptavidin coated magnetic beads (Promega, Madison, Wis.) with immobilized Fab biotinylated with a cleavable disulfide linker (Thermo Fisher, Waltham, Mass.) at a final concentration of 100 nM. Phage particles were allowed to incubate with target for ~1 hour with gentle shaking before several washing steps were performed to remove unbound virions. Phage particles were eluted from the beads with 100 mM DTT to release the Fab from the resin and the resulting supernatant was used to infect log phase XL1 for ~20 minutes. M13K07 helper phage was added to final concentration of 10$^{10}$ pfu/ml for overnight growth (Paduch et al., 2013). Rounds two and three were performed with phage particles isolated from the overnight amplification of the previous round. Here, ~10$^{10}$ cfu of rounds 1 and 2 amplification were used for the next round of selection in a KingFisher magnetic bead sorter (Thermo Fisher, Waltham, Mass.). Selection and amplification for subsequent rounds were similar to round 1 except 50 nM and 10 nM Fab were immobilized for rounds 2 and 3, respectively. Enrichment of phage particle output relative to a negative control reached 1000. Round 3 output was subsequently PCR amplified and ligated into pHFT2 (Huang et al., 2008) for analysis by protein ELISA. The resulting ligation mixture was transformed into BL21(DE3) Gold and colonies were screened by ELISA.

4. Immunoassays

Overnight cultures induced with 1 mM IPTG were centrifuged and lysed with BugBuster (Novagen, Madison, Wis.) following the manufacturer's protocol. Cleared lysates were incubated at 70° C. for 30 minutes before incubation with Nunc Maxisorp plates immobilized with 20 nM Fab. Protein-G binding was detected via Flag-HRP. Isolated clones were sequenced to identify variants for large-scale expression.

5. Protein Expression and Purification

Protein-G variants isolated from ELISA were expressed in 1 L cultures in the expression strain BL21(DE3). Protein expression was induced at mid-log phase through the addition of 1 mM IPTG. Expression proceeded for 5 hours at 37° C. Protein was extracted by sonication and purified by Ni-NTA affinity chromatography using standard procedures. Yields for the Protein-G fusions were typically ~200 mg/L. Antibody fragments were expressed and purified using protocols previously described (Paduch et al., 2013) or those described in Results. Yeast Anti-silencing-1 was expressed from the pHFT2 vector in BL21(DE3) and purified via Ni-NTA as described for the Protein-G variants. Sequences of Protein-G-A1, SUMO-Protein-G-A1 and Protein-G-A1 dimer are listed in the Supplementary Information.

6. Circular Dichroism

Protein-G samples (0.1 mg/mL, ~13 µM) were prepared in 1.5 M guanidinium hydrochloride (Gdn-HCl), 0.1M cacodylate buffer, pH 7.0 and added to a 1 mm quartz cuvette. The sample was heated from 25-85° C. in 1° C. increments every 5 seconds while the absorbance at 207 nm was monitored. Far-UV wavelength scans where data was collected every 1 nm/5 s from 200-250 nm were performed before and after each temperature melt experiment to determine the extent of reversibility.

7. Base Stability Measurements

Figure 10:
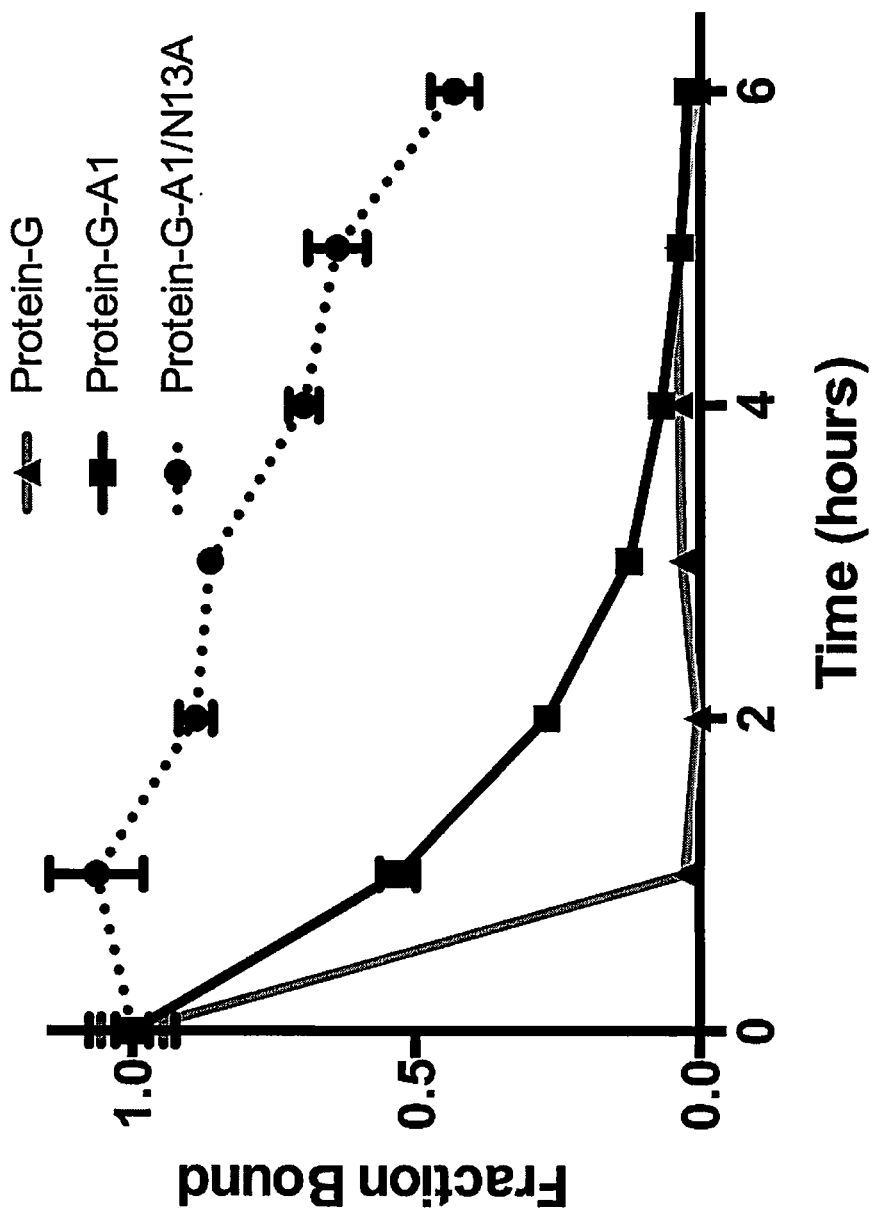
FIG. 10—Base stability of the protein G variants showing fraction bound over time intervals of 0-6 hours.

Protein-G variants were incubated in 0.1 M NaOH and quenched at various time points through a 100-fold dilution into PBS. Samples (5 µM-1 nM) were subjected to protein ELISA with immobilized Fab (20 nM). The fraction of sample retaining binding was calculated based on comparison to the control sample at a Protein-G concentration that produced an ELISA signal that was at the top of the linear, dynamic range (FIG. 10).

8. Sulfo-Link Resin Preparation

ProteinG-A1 resin was created using SulfoLink Coupling Resin (Thermo Scientific) following the manufacturer's protocol. To couple the protein to the resin, a free cysteine was introduced at the Q6 position of SUMO on the SUMO-Protein-G-A1 variant. Briefly, to make 1 mL of Protein-G-A1 resin, the column was first equilibrated with coupling buffer (50 mM Tris, 5 mM EDTA, pH 8.5). Prior to immobilization, SUMO-Protein-G-A1 was treated with a 10-fold molar excess of TCEP and diluted to 6 mg/mL in coupling buffer. A volume of 2 mL SUMO-Protein-G-A1 (12 mg ProteinG-A1/mL resin) was added to the column and allowed to incubate for 45 minutes with intermittent mixing. The flow-through was collected to analyze coupling efficiency. After washing with coupling buffer, excess binding sites on the resin were blocked with a solution of 50 mM L-Cysteine in coupling buffer and the column was washed with 1 M NaCl. Typically, 10 mg of SUMO-Protein-G-A1 was captured on 1 mL of resin.

9. Test of Multivalency:

A Protein-G-A1 dimer was created through the introduction of a $(G_4S)_3$-Protein-G-A1 fragment into the pHFT2-Protein-G-A1 vector. The resulting dimer was expressed in BL21(DE3) in a similar manner to the monomeric Protein-G variants. Generation of the non-covalent Protein-G-A1 dimer was achieved through incubation of 10 µM Fab specific for Anti-silencing factor 1 with 0.5 equivalents of Protein-G-A1 dimer. Asf1 was immobilized on a Maxisorp plate and titrations of Fab, F(ab')$_2$ or Protein-G-A1-Fab were tested for their ability to bind immobilized target. Bound Fab was detected by Protein-A-HRP. Control experiments using anti-FLAG-HRP as a secondary antibody indicated dimeric Protein-G-A1 had negligible binding to the target or blocked plate at a concentration of 500 nM.

B. Results and Discussion

1. Phage Library Generation and Selection

A modified variant of the Protein-G C2 domain from *Streptococcus* was displayed on filamentous phage as a fusion to the C-terminal domain of minor coat protein III. Guided by inspection of the structure of the *Streptococcus* Protein-G-Fab complex (pdb 1IGC), diversity was introduced in the 15 residues of Protein-G within 5 Å of the interface (FIG. 6B) employing a soft randomization library design strategy. This strategy biases the library to the wild type sequence, focusing introduction of diversity at positions where the substitution is favored over the wild-type residue.

Using Kunkel mutagenesis, a library of ~3×10$^9$ variants was created and subjected to three rounds of bio-panning using decreasing amounts of the immobilized Fab antigen each round of the selection (100 nM, 50 nM and 10 nM, respectively). Stable variants were identified with high affinity to the Fab with a heat denaturation step followed by protein ELISA. The ELISA evaluation identified a number of variants that were further characterized by Surface Plasmon Resonance (SPR) (FIGS. 6C and 6D). All Protein-G variants tested had affinities 3-100-fold higher than the starting variant, confirming the potential for engineering this interface.

FIG. 6C shows the mutated residues of the engineered variants in the context of the wild type sequence. The selection resulted in variants with mutations at the majority of positions randomized within the library. This is not surprising because the major interaction of Protein-G with the Fab is through a β-strand where backbone H-bonds generally contribute more to binding than side chains (Derrick and Wigley, 1992). Position 18 is a notable example of this as the parent lysine residue was replaced by arginine, serine and tryptophan in the higher affinity variants.

Despite the diversity of sequences retrieved from the bio-panning, there were several positions where the parent residue was conserved or retained in chemical character. For instance, Leu17 projects its side chain into the core of the domain and remained the preferred residue with mutations to phenylalanine and alanine observed. Glycine remains the dominant residue at position 19; however, tyrosine appears in two variants, perhaps reflecting the potential for additional energetically favorable contacts since the Cα of glycine projects toward the Fab heavy chain. Thr21 and Thr22 were retained at the C-terminal portion of the β-strand consistent with the preferred status of β-branched residues in exposed β-strands. Additionally, two parent residues within the α-helical region of Protein-G were favored. Tyr38 projects into the immunoglobulin domain strands β1 and β7 where the aromatic side chain interacts with a number of conserved hydrophobic residues. Here, it remained the dominant amino acid at this position in addition to two variants containing isoleucine to retain the aliphatic character of the complex interface. Asn42 forms a hydrogen bond with Val128 in the buried complex and the hydrogen bonding potential at this position is preserved with engineered Protein-G variants containing either Asn, Gln, His or Tyr.

A notable divergence from the parent sequence occurred at position Asn40, which in a number of resulting sequences showed a preference for aromatic residues such as tyrosine and phenylalanine. Asn40 buries roughly 40 Å$^2$ at the complex interface with the light chain. Presumably, the bulkier aromatic side chains contribute energetically favorable interaction as aromatic residues are known to be contributors to "hot spots" in many protein-protein interactions (Bogan and Thorn, 1998).

The tightest binding variant, Protein-G-A1 had an ~100-fold higher affinity for the Fab compared to the wild-type Protein-G. With a K$_D$ of ~25 nM determined by equilibrium SPR (FIG. 6D), this variant has suitable properties that can be exploited for use in a number of applications including purification, immunoprecipitation and as a crystallization chaperone (Dyson et al., 2011). Protein-G-A1 demonstrates a preference for the human IgG1 isotype as its affinity was decreased by a factor of ~20-50-fold for IgG2, IgG3 and IgG4, suggesting subtle differences in domain orientation impact binding (Not shown). Furthermore, targeted mutagenesis of Protein-G-A1 identified mutations that abolish IgG Fc binding while maintaining the paratope-responsible high affinity Fab interaction for applications requiring the separation of Fab and Fc fragments. The protein exhibited favorable biophysical characteristics including high solubility (>10 mM) and thermal stability (T$_M$~58° C. in 1.5 M GdmHCl). Thus, the Protein-G-A1 variant was used to perform functional analysis to evaluate its potential in the applications described below.

2. pH Dependence of the Engineered Protein-G Variant

Figure 7:
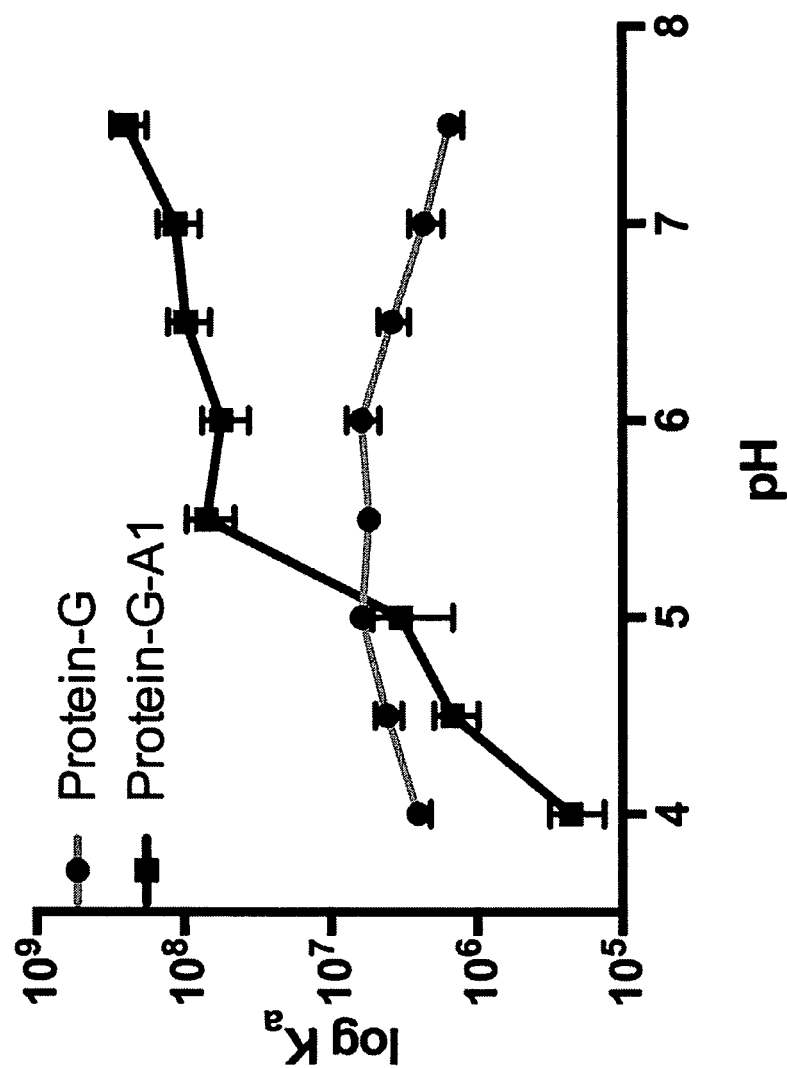
FIG. 7—pH-dependence of protein G variants. Wild type protein G (open circles) and protein G-A1 (closed circles).

Examination of the Protein-G-Fab structure indicated that there were two ionizable residues (His42 and Glu43) introduced into Protein-G-A1 that were located directly in the interface with the Fab. To explore their potential to affect the pH-dependent affinity of this variant, pH-varied fluorescence polarization studies were performed with Alexa-Fluor labeled Protein-G and the Protein-G-A1 variant. The wild type variant exhibited a broad pH optimum between 5 and 6.5, with a $K_D$ at pH 4 almost indistinguishable from that at physiological levels. In contrast, Protein-G-A1 exhibited 1000-fold decrease in affinity from pH 7.5 to pH 4 (FIG. 7). The change in affinity was particularly pronounced at pH 5.5 where a ~300-fold loss of affinity was observed between pH 5.5 and pH 4.0. Simple inspection of d log $K_A$/d log $H^+$ indicated that the slope at low pH is ~1.5, compared with 0.4 for the wild-type interaction. Two residues within the protein complex interface plausibly provide the origin of the pH dependence. The G43E mutation occurs between the loop connecting the a helix with β-strand 3. Here the mutation at this position from glycine to glutamate may provide favorable electrostatic interactions with residues in the light chain including Lys126 of $C_H1$. Asn42 forms a hydrogen bonding interaction with the main chain N of Val128. If this hydrogen bonding interaction is conserved in Protein-G-A1, a protonation event at His42 would break this interaction, perhaps accounting for the loss of affinity beginning at pH 5.5. Comparison of the simulated pKa at the binding interface with other histidine residues found buried at protein surfaces indicates this protonation event falls within those observed for other histidine residues (Edgcomb and Murphy, 2002)

3. Exploiting the pH Switch as a Tunable Binding Switch

Figures 8A, 8B:
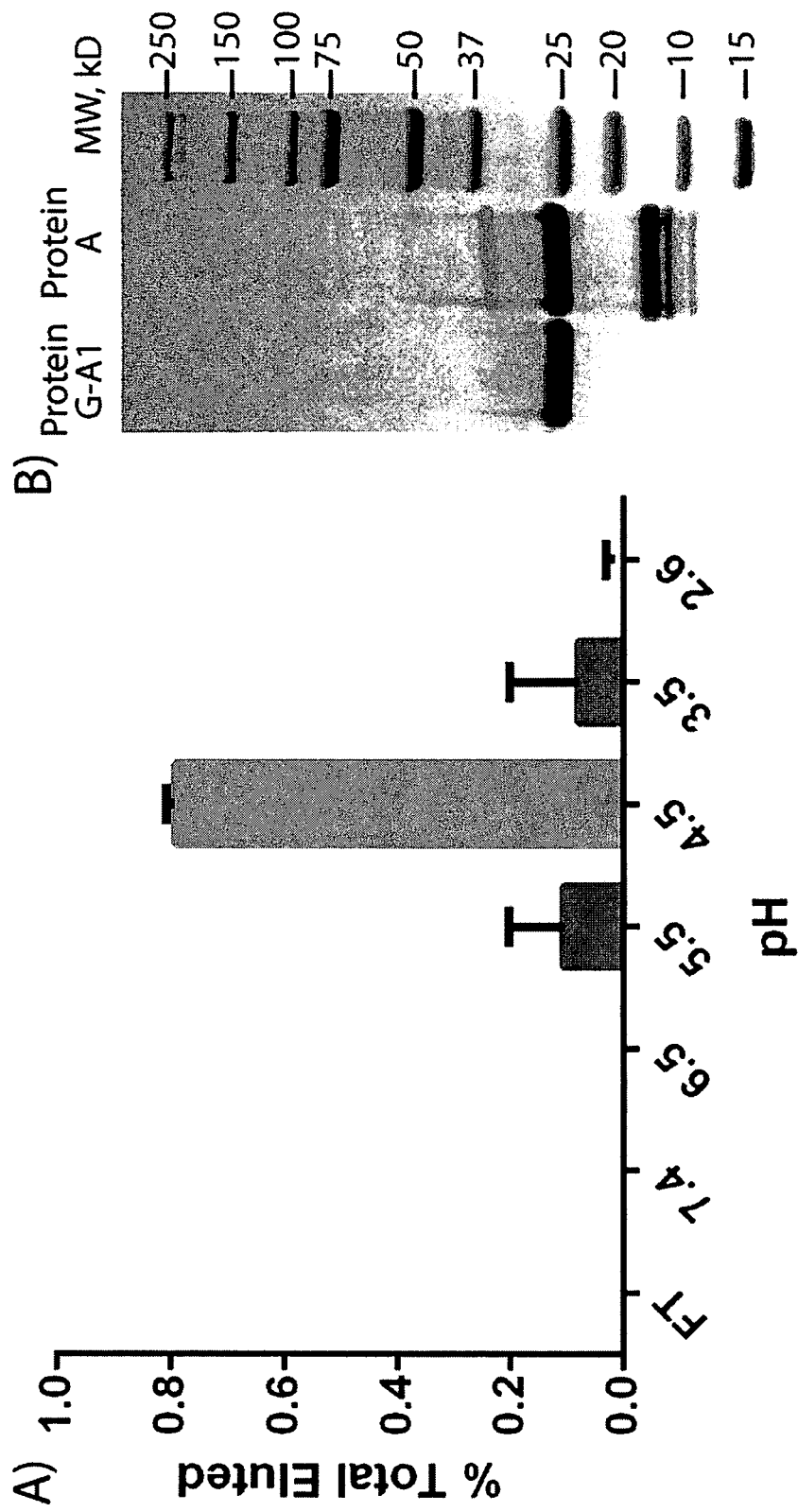
FIGS. 8A-8B—Purification of Fabs from protein G-A1 resin. A. pH-dependence of elution. Protein G-A1 retained the Fab on the column until washed with buffer at pH 5.5 to 3.5 where it was eluted. B. Gel electrophoresis of purified Fab. Lane 1 depicts the purification of Fab from lysate using the protein G-A1 resin while lane 2 shows the results of purification from commercial protein A resin.

The introduction of a pH switch provides an advantageous molecular property that can be exploited for antibody fragment purification. Significant efforts have been expended to design protein affinity ligands with the controllable protein binding to enable elution in less harsh conditions (Murtaugh et al., 2011; Strauch et al., 2014). To evaluate the ability of Protein-G-A1 as a purification resin, a SUMO-Protein-G-A1 fusion was conjugated via an introduced N-terminal cysteine to Sulfo-Link Resin. Notably, the high resin capacity of >10 mg/mL and was amenable to extensive washing with a range of ionic strength buffers at neutral pH. Furthermore, it was possible to readily elute the majority of the Fab protein at pH 4.5 after washing with 10 column volumes (FIG. 8A). This compared favorably to the parent domain as minimal Fab fragment remained bound to the column after extensive washing in PBS. Protein-G-A1 was also capable of single-step purification of antibody fragments from cell lysate. FIG. 8B. shows the elution of Fab from cell lysate using Protein-G-A1 and Protein-A columns. The resulting Fab from the Protein-G-A1 column eluted as a single, full-length protein whereas the Protein-A column retained degradation products presumably resulting from soluble fragments of $V_H$ and $V_K$.

4. Protein-G-A1 Alkaline Stability

A key determinant to the successful regeneration of a protein affinity reagent is the stability of the scaffold throughout the purification and cleaning process. Sensitivity to alkaline conditions commonly found in cleaning in place (CIP) methods, has proven problematic for protein affinity reagents since such conditions facilitate base-catalyzed deamidation of aspargine and glutamine residues. Previous studies of Protein-G indicated it is highly sensitive to base-catalyzed degradation with a half-life of ~15 minutes in 0.5 M NaOH. Notably, Protein-G has been previously engineered to improve the alkaline stability, where Asn40 and Asn42 have been found to be particularly prone to deamidation (Gülich et al., 2002). However, an N7A/N36A double mutant led to a loss of Fab binding affinity, presumably because of the critical contacts Asn36 provides in the Protein-G-Fab complex. To establish the whether there were residue types that could substitute for the asparagine residues without diminishing binding, these residues were included in the region of Protein-G randomized during affinity maturation. The subsequent bio-panning was able to identify a number of variants where the base-labile Asn residues were replaced, including Protein-G-A1.

Figure 9:
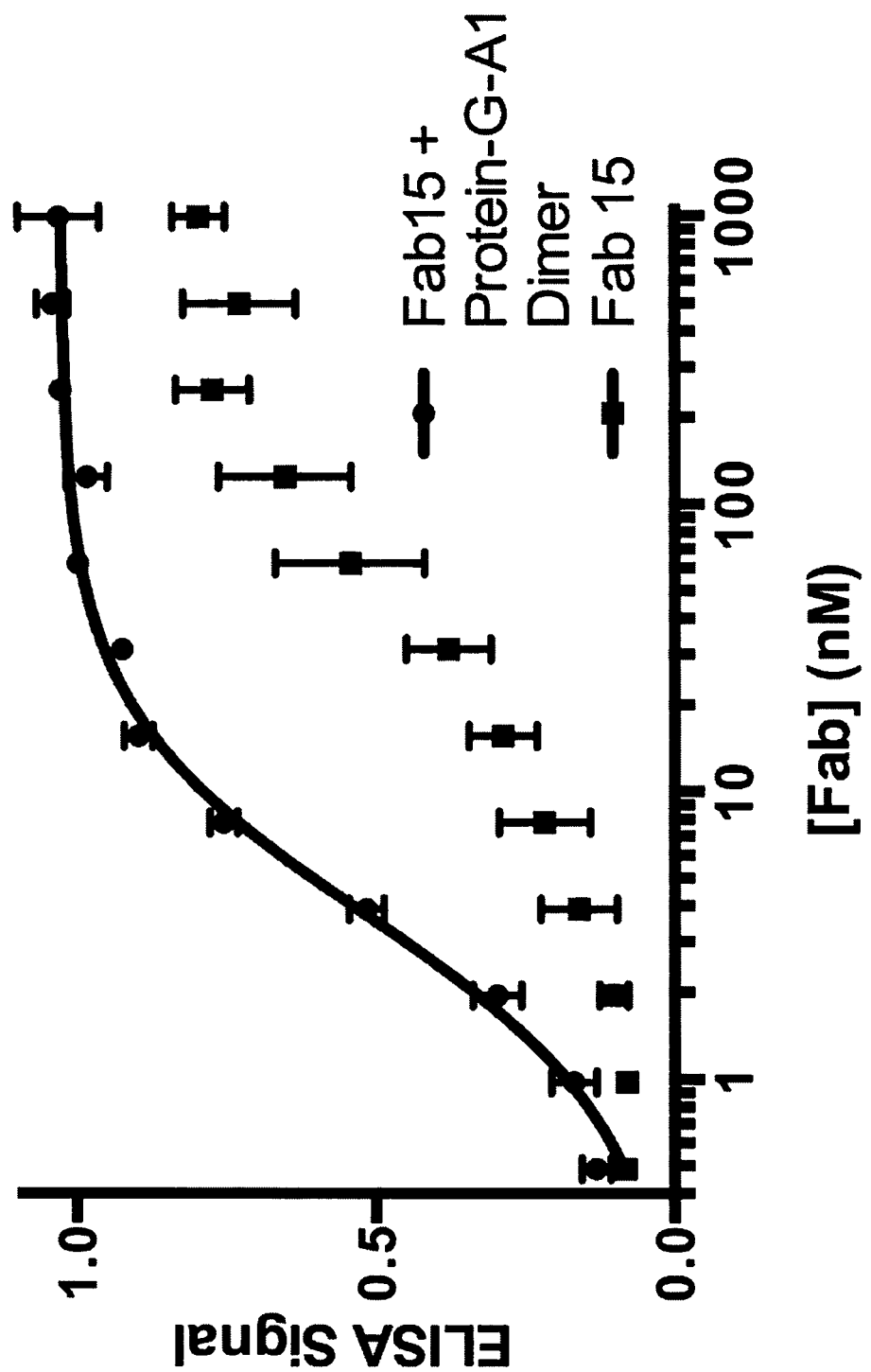
FIG. 9—Protein G-A1-induced multivalency of a Fab-antigen interaction. An antibody fragment specific to anti-silencing factor 1 (asf1) tested for its ability to bind antigen with (top line) or without (bottom) 0.5 equivalents for protein G-A1 dimer.

To assess the base stability, Protein-G variants were incubated in 0.1 M NaOH, a commonly used CIP reagent, and residual binding was measured through ELISA. The wild-type domain rapidly loses the capacity to bind Fab after base incubation for one hour (FIG. 9). In contrast, Protein-G-A1 retained ~50% of its binding capacity in the same time interval, significantly stabilizing it to base hydrolysis. Further engineering of Protein-G-A1 to include the N13A mutation, a residue distal from the binding interface, further improved the stability with complete binding retained after one hour and ~50% binding after 6 hours. It is anticipated that rational identification of base-labile residues coupled with functional selection to identify residues with more ideal properties may be a route to generate more robust protein affinity reagents.

5. Non-Covalent Avidity Enhancement

Multivalency is a hallmark of natural immunoglobulins and is a critical feature to the efficacy of antibodies in vivo and in research, diagnostic, and therapeutic applications. Multimerization of affinity reagents can yield significant improvements in apparent affinity with reported values ranging from $10$-$10^5$-fold (Krishnamurthy et al.). Unlike antibodies derived from an immune response, most synthetically-derived antibody fragments are monovalent unless otherwise functionalized. Notably, a number of antibodies are limited by their fast dissociation constants in assays requiring extensive washing, including IP and immunefluorescence (IF), thus requiring further functionalization to achieve multivalency (Dyson et al., 2011). This has been achieved through a number of strategies including in vitro production of the F(ab')$_2$ fusion to coiled-coil domains (Pack and Plückthun, 1992) and Avi-tag peptide for multimerization through avidin (Kay et al., 2009).

An alternative more facile strategy presented here exploits the affinity-matured Protein-G-A1 dimer linked through a (Gly$_4$Ser)$_3$ tether. To test the ability of the Protein-G-A1 dimer to enhance the apparent affinity of an antibody-antigen interaction, ELISA was performed with an antibody fragment specific to the histone chaperone anti-silencing factor 1 (Asf1) (FIG. 10). Asf1 was immobilized through a biotin-NAV interaction to test the role of Protein-G-induced avidity. The EC$_{50}$ of the monovalent Fab fragment was 35 nM. However, through the addition of 0.5 equivalents of the Protein-G-A1 dimer, an apparent EC$_{50}$ of ~4 nM was observed, roughly a 9-fold enhancement of the apparent affinity of the Fab-antigen interaction, comparable to previously reported values of multivalency ((Krishnamurthy et al., 2006).). Notably, this was achieved through non-covalent multimerization of the antibody fragment. Further functionalization of the Fab fragment-Protein-G interaction by cysteine crosslinking may provide the necessary covalent attachment in instances where sub-nanomolar concentrations do not favor Fab-Protein-G complex formation.

6. Conclusions

A variant of Protein-G was engineered with significantly improved affinity for the Fab portion of an IgG. Furthermore, this interaction can be effectively modulated through pH changes as there is an 1000-fold change in $K_D$ when going from pH 7.5 to 4 (FIG. 7). This engineered variant possesses biophysical characteristics favorable for a number of applications. Ultimately, these results enable more facile performance of this protein affinity ligand for a number of applications.

Example 2: Creation of Protein-G Multi-Valent and Multi-Specific Molecules

1. Multi-Valent and Multi-Specific Constructs

Figure 15:
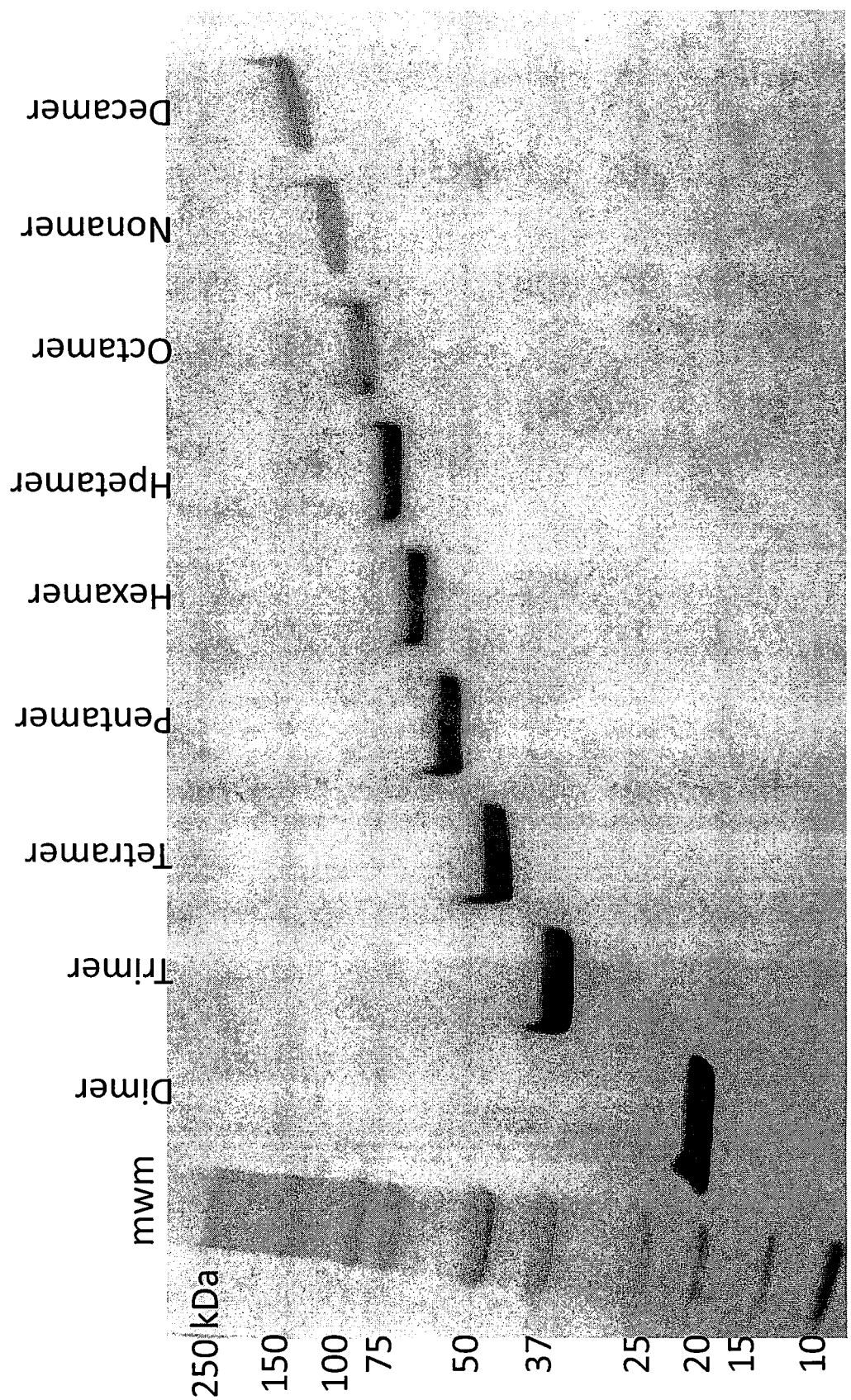
FIG. 15—Protein-G-A1 multimers expressed and purified with a Gly-Ser rich linker. Shows that Protein-G domains can be efficiently linked together up to at least 10 copies.

The generation of Fab isotype-specific Protein-G variants enables the creation of multi-valent and multi-specific Fab constructs through several routes. These include non-covalent tethering of Fab to Protein-G variant multimers. The multimers are Protein-G variants linked together through a polypeptide linker described above (FIG. 13). The linker length can be readily adjusted to suit the application. While most linkers consist of combinations of Gly and Ser, other amino acid types can be introduced; for instance Pro to add "stiffness". Importantly, each Protein-G variant can be present in the construct multiple times. We have demonstrated that up to ten copies of Protein-G variants can be linked together and loaded with Fab moieties (FIG. 15). To create the multi-valent construct in a non-covalent fashion, components (Fab and Protein-G variant binding moiety) are simply added together in stoichiometric amounts to enable complex formation. Incubation of the reagents for 15 minutes or less should enable complex formation. In instances where a Protein-G variant is to be covalently fused to the Fab, cysteine mutant constructs of Protein-G variants and Fabs must be added together. This can include stoichiometric addition of Fab and Protein-G binding variants or can include adding excess of either reagent to enable faster disulfide bond formation. Here, a series of matching Fab-Protein-G variants (Protein-$G^{16}$ and $Fab_{CL}^{221}$, Protein-G-$A1^{18}$ and $Fab_{CL}^{220}$, Protein-$G^{20}$ and $Fab_{CL}^{218}$ and Protein-$G^{22}$ and $Fab^{216}$) can be added in the presence or absence of oxidizing reagents to enable disulfide bond formation. These include copper phenanthroline and dehydroascorbic acid in amounts from 0 to 5 mM. Oxidation generally occurs within an hour and oftentimes within 15 minutes at physiological pH (PBS). If stoichiometric addition of Fab and Protein-G occurred, simple dialysis or desalting should be sufficient to obtain a variant for use. Alternatively, further purification of the multi-specific variant can be performed to obtain a homogenous protein sample.

2. Multi-Specific Protein-G Molecules

Figure 4C:
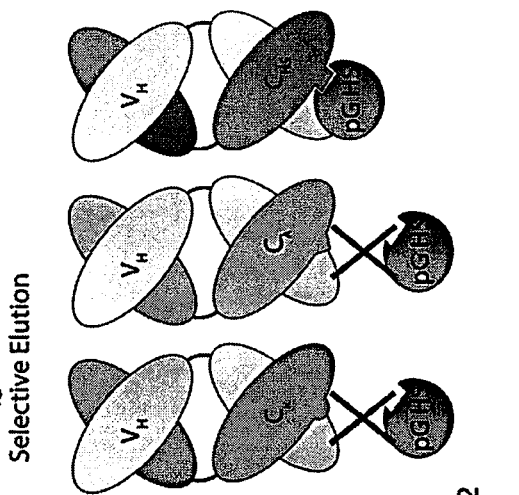
Figure 4D:
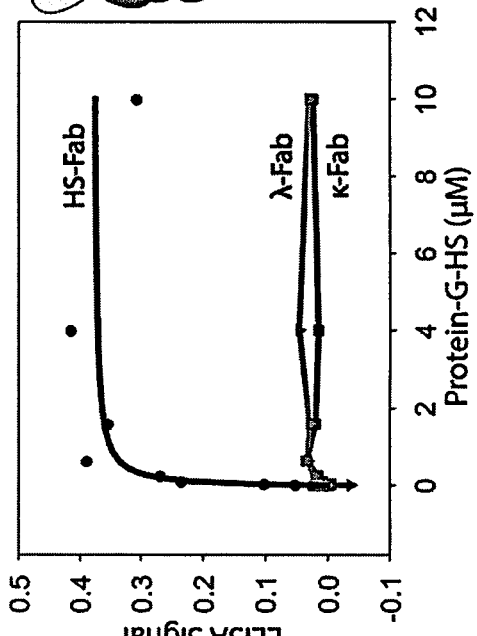
Figure 16A:
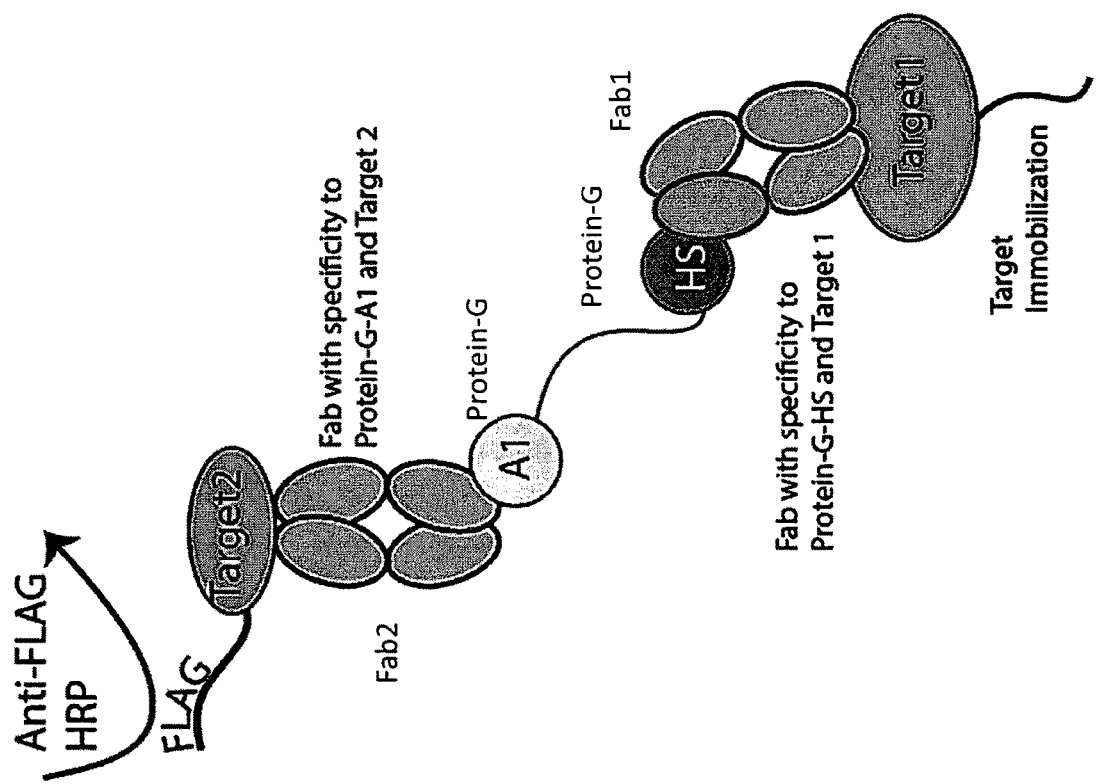
FIG. 16A-16C—A. Bi-specific constructions-Fab1 binds to target 1. The light chain of Fab1 has the HS sequence mutated in. Protein-G HS is a mutant that recognizes the HS sequence, but not the wild-type sequence. Fab2 is the wild-type construct with the affinity matured protein-G variant A1. A1 does not recognize the HS sequence. Therefore, by linking the two orthogonal Protein-G variants A1 and HS, you can bind two different Fabs with different specificities. Detection of multiple targets in a sample. B. Elisa of Target 2 with various constructs. C. Sequence of wild-type isotype (Kappa) recognition region (SEQ ID NO:18) and HS-specific variants, A1, C6 and C7 (SEQ ID NOS:20-22, respectively) as well as HS light chain variant (SEQ ID NO:102) and kappa light chain (SEQ ID NO:105).
Figures 16B, 16C:
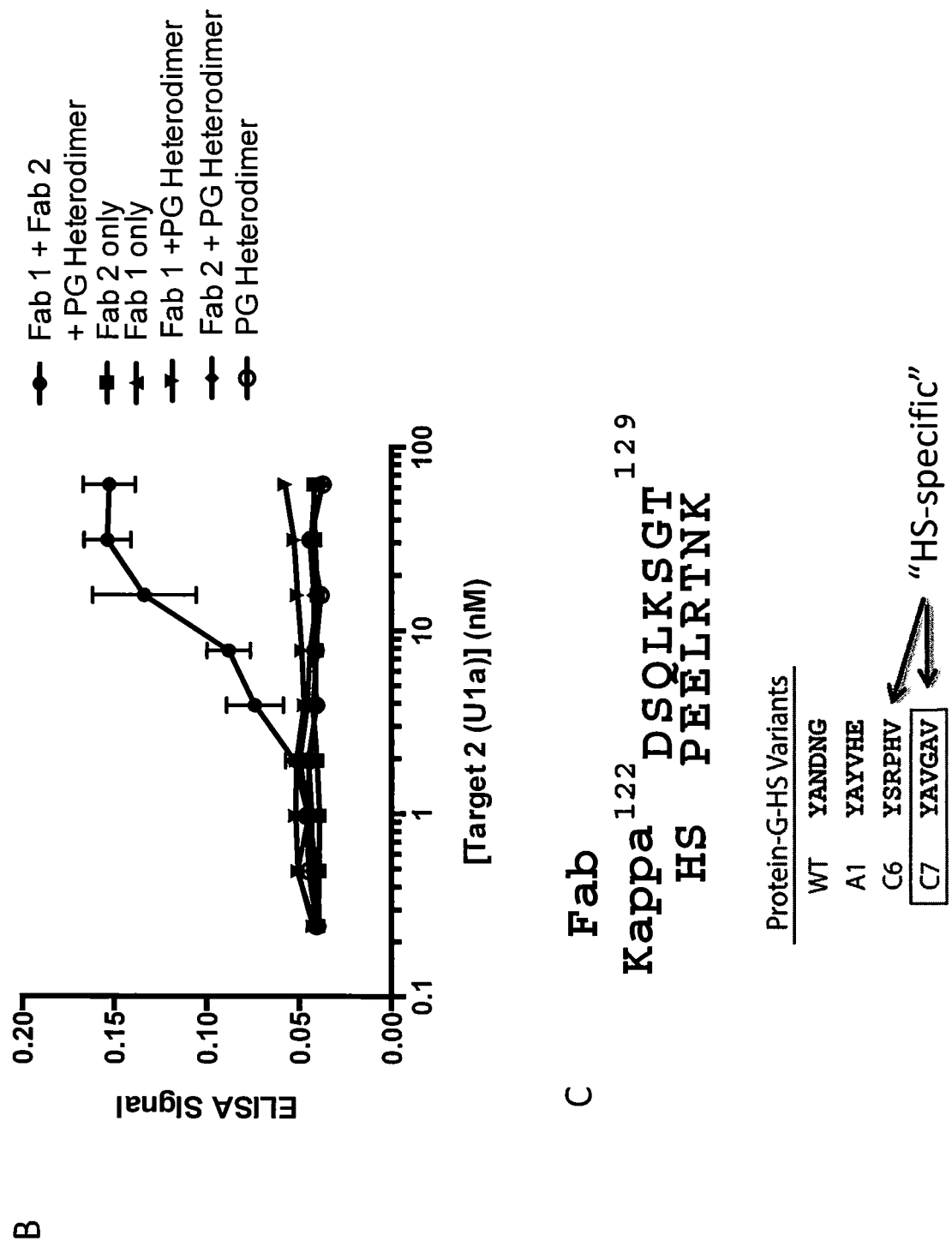

Fabs with different constant domain isotypes will have unique specificity such that a single covalent or non-covalent entity will allow for simultaneous engagement of two or more antigens. For instance, a Protein-G construct would contain the Protein-G variant specific for the wild-type Kappa-specific Fab isotype (Protein-G-A1) fused through a linker to the engineered Protein-G Lambda isotype denoted as "HS" (FIG. 13). To generate Protein-G variants that distinguish the different Fab-isotype variants, the distal region of Protein-G corresponding to amino acids YANDNG (SEQ ID NO:18) is varied. Protein G comprising SEQ ID NO: 62-68 would recognize the specific Fab-HS mutations. This Protein-G HS isotype binds to an engineered form of Fab with mutations (sequences 6 and 7) shown in FIG. 4c. These variants do not bind to any form of Protein-G except HS, providing exquisite specificity that can be exploited to readily make bi-specific constructions. As an example of the process to optimize these bi-specific constructions, we used the protein Asf1 as antigen 1 and the RNA binding protein U1A as antigen 2. ELISAs were run where antigen 1 was immobilized on a Maxisorp plate coated with neutravidin. Subsequently, a mixture of Protein-G-A1-Protein-G-HS, $Fab_{Hs}$ (specific to antigen 1) and $Fab_K$ (specific to antigen 2) were added in stoichiometric amounts. After a period of incubation (~15 min) and washing, antigen 2 was titrated at concentrations of 0-250 nM. Subsequent binding of antigen 2 was detected by anti-FLAG-HRP, which detected an epitope tag on antigen 2 (FIG. 16A). The ELISA data demonstrate titratable, saturable binding of U1A (antigen 2) only when all reagents are added to the ELISA well indicating the Protein-G-A1-Protein-G-HS fusion allows for the simultaneous engagement of multiple, specific binding partners (FIG. 16B, C)). The stability of the bi-specific constructs can be improved by covalent attachment of different Fab scaffold types to their cognate Protein-G isotype using the disulfide linking strategy described above. There is no impediment to generating tri-specific or higher order of specificity by similar engineering strategies. Such reagents should enable the development of facile production of multivalent constructs for rapid assessment of multi-specific affinity and activity enhancement.

3. Protein-G Fusions with Fc Domains

The Protein-G variants can be linked as fusions to other proteins (including the Fc region of the human IgG) to add additional function (FIG. 14). Generation of Fc fusions is an established technology for expressing protein antigens on the surface of mammalian cells (Lo et al. 1998). In such cases, the Fc-Protein-G construct would contain the Protein-G variant specific for the wild-type Kappa-specific Fab isotype (Protein-G-A1) fused by a linker to the Fc region of an IgG molecule of choice. It is known that when expressed, such constructs will dimerized through contacts found in the Fc domain. These fusion proteins will mimic the dimeric antibody structure of the native molecule because there is a flexible linker between the heavy chain Fab region, which ends at about residue 223 and the Fc region, which is also part of the heavy chain and starts at about residue 230 (Kabat numbering). However, unlike natural antibodies, the composition and length of the linker between the Protein-G variant binding domain and the Fc domain is adjustable. The utility of these constructs can be further expanded by introducing fusions that contain Protein-G isotypes that can generate multi-specific binding moieties (FIG. 14). In another type of construction, multi-valency and multi-specificity can be introduced by separating these functions on different Fc domains. It is known that co-expressing, for instance the A1-A1-Fc and the HS-HS-Fc fusions, will lead to a mix of products including homodimers of the A1-A1-Fc, HS-HS-Fc constructs and the desired A1-A1-Fc, HS-HS-Fc heterodimers. To optimize the desired bi-specific heterodimers, a "knobs and holes" strategy will be used as described by Ridgeway et al (Ridgeway et al. 1996). This strategy identifies 2-4 specific residues in the CH3 Fc dimerization region where mutations that introduce larger side chain types ("knobs") in one Fc monomer which can be complemented by introducing side chain types that produce "holes" in the other Fc monomer. This prevents homodimerization since "knob-knob" or "hole-hole" contacts are incompatible with dimerization. Thus, for instance, it is straightforward to construct the A1-A1-Fc version with knobs and HS-HS-Fc with holes to generate the heterodimeric multi-specific and multi-valent antibody, a molecule that cannot be made by any other approach.

Example 3 Reduced Immunogenicity

Immunogenicity is a major concern in the development of protein reagents and therapeutics as it can result in neutralization, clearance or severe immune responses upon delivery. Notably, immunoglobulin binding domain protein leaching from antibody affinity columns has been implicated in inflammation responses observed for some therapeutic proteins, indicating a need for control of this feature of affinity reagents. While the complexity of the B-cell immune response prevents accurate prediction of antibody generation, identification of T-cell epitopes is more straightforward. Significant efforts to delineate sequence-specific determinants of immunogenicity have enabled computational approaches to predict T-cell epitopes from primary sequence (Wang et al., 2008). Such approaches have enabled the deletion of T-cell epitopes of therapeutic proteins and enzymes thereby reducing the production of neutralizing antibodies in vivo. T-cell epitope predictions are based upon peptide binding capacity to the MHC class II protein found on the surface of antigen presenting cells, a prerequisite for T-cell epitope generation. Here, the primary determinants of MHC class II binding are amino acid side chains at positions 1, 4, 6 and 9 of the polypeptide chain. Using the Immune Epitope Database (IEDB), we screened the primary sequence of Protein-G-A1 to identify regions predicted to bind to the most common HLA-DR alleles found in the human population. We focused on sequences with a consensus percentile rank (CPR) lower than 2, a value in the lowest 10% of parsed peptide fragments as previously described. Interestingly, the nine-residue peptide with the lowest CPR ($^{10}$LVINGRTLS$^{18}$) (corresponding to amino acids 134-142 of SEQ ID NO:15) included residues from the β-strands 1 and 2, including several residues comprising the protein-protein interaction site with $C_H1$ of the Fab. We reasoned that a phage library incorporating hard randomization (NNK diversity) into residues 10, 13, 15 and 18 (underlined residues in sequence) coupled with phage panning on the Fab would enable us to isolate a variety of sequences at the residues critical for recognition of MHC class II which still retain Fab binding. The resulting variants were subjected to sequence analysis to identify variants with reduced immunogenicity as determined by IEDB. Combining phage panning and analysis via phage ELISA identified a number of sequences with lower predicted immunogenicity (see table below).

| Variant | Immunogenicity Region | lowest hit (%) | # below 2 |
|---|---|---|---|
| B11 | LVIRGLTLSL (SEQ ID NO: 27) | 0.38 | |
| B12 | LVIRGLTLSF (SEQ ID NO: 28) | | |
| B5 | LVIGGLRLWF (SEQ ID NO: 29) | 0.68 | |
| B6 | LVIRGVTLLF (SEQ ID NO: 30) | 0.51 | |
| B7 | LVIRGITLGF (SEQ ID NO: 31) | 0.51 | |
| B8 | LVIMGSTLSL (SEQ ID NO: 32) | 0.23 | |
| B9 | LVIIGRTLSL (SEQ ID NO: 33) | 0.19 | |
| B10 | LVISGITLSF (SEQ ID NO: 34) | 0.6 | 2 |
| A11 | LVIGGRTLSF (SEQ ID NO: 35) | 1.35 | 2 |
| A12 | LVIGGRTLSF (SEQ ID NO: 36) | 1.35 | 2 |
| B1 | LVISGSTLSL (SEQ ID NO: 37) | 1.72 | 2 |
| B2 | LVILGRTLSV (SEQ ID NO: 38) | 0.07 | 7 |
| B3 | FVIRGRTLSF (SEQ ID NO: 39) | 0.06 | 8 |
| B4 | LVISGRTLSL (SEQ ID NO: 40) | 0.38 | 6 |
| A8 | LVIGGRTLRF (SEQ ID NO: 41) | 0.73 | 5 |
| A9 | LVIRGVTLGF (SEQ ID NO: 42) | 0.23 | 4 |
| A10 | LVIRGRTLSL (SEQ ID NO: 43) | 0.1 | 8 |
| A1 | LVIGGRTLRF (SEQ ID NO: 44) | 0.75 | 7 |
| A2 | LVIGGRTLSF (SEQ ID NO: 45) | 1.35 | 2 |
| A3 | LVISGLTLSF (SEQ ID NO: 46) | 1.2 | 2 |
| A4 | LVIGGVTLSF (SEQ ID NO: 47) | 1.06 | 2 |
| A5 | LVIRGVTLSL (SEQ ID NO: 48) | 0.07 | 4 |
| A6 | LVIGGITLSF (SEQ ID NO: 49) | 1.93 | 2 |
| WT | LVINGRTLSG (SEQ ID NO: 50) | 0.11 | 6 |

These included variant A6 with a CPR of 1.93, a value near the threshold set for identification and higher than that of the parent Protein-G-A1 (CPR=0.11 for Protein-G-A1). Also notable is there are a number of variants with fewer predicted T-cell epitopes compared to the wild-type Protein-G-A1 (two compared with six). Additionally, we anticipate combinations of residues from the analyzed sequences may provide even further reduction in predicted immunogenicity, providing a route for combinatorial production of reduced immunogenicity Protein-G variants.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims. All the references, publications, and sequences associated with the recited GenBank Accession numbers are specifically incorporated by reference for all purposes.

REFERENCES

The following references and those cited throughout the disclosure (including patent documents and non-patent literature), to the extent that they provide exemplary procedural or other details supplementary to those set forth herein, are each specifically incorporated herein by reference each in its entirety.

Bogan, A. A., and K. S. Thorn, 1998, Anatomy of hot spots in protein interfaces: J Mol Biol, v. 280, p. 1-9.

Bjorck, L., & Kronvall, G. (1984). Purification and some properties of Streptococcal Protein G, a novel IgG-binding reagent. Journal of Immunology, 133(2), 969-974.

Bradbury, A. R., S. Sidhu, S. Dübel, and J. McCafferty, 2011, Beyond natural antibodies: the power of in vitro display technologies: Nat Biotechnol, v. 29, p. 245-54.

Cantor, J., Yoo, T., Dixit, A., Iverson, B., Forsthuber, T., & Georgiou, G. (2011). Therapeutic enzyme deimmunization by combinatorial T-cell epitope removal using neutral drift. Proceedings of the National Academy of Sciences, 1272-1277.

Colwill, K., S. Gräslund, and R. P. B. W. Group, 2011, A roadmap to generate renewable protein binders to the human proteome: Nat Methods, v. 8, p. 551-8.

Derrick, J. P., and D. B. Wigley, 1992, Crystal structure of a streptococcal protein G domain bound to an Fab fragment: Nature, v. 359, p. 752-4.

Dyson, M. R., Y. Zheng, C. Zhang, K. Colwill, K. Pershad, B. K. Kay, T. Pawson, and J. McCafferty, 2011, Mapping protein interactions by combining antibody affinity maturation and mass spectrometry: Anal Biochem, v. 417, p. 25-35.

Edgcomb, S. P., and K. P. Murphy, 2002, Variability in the pKa of histidine side-chains correlates with burial within proteins: Proteins, v. 49, p. 1-6.

Engler, C., & Marillonnet, S. (2013). Golden Gate Cloning. DNA Cloning and Assembly Methods Methods in Molecular Biology, 119-131.

Fellouse, F. A., K. Esaki, S. Birtalan, D. Raptis, V. J. Cancasci, A. Koide, P. Jhurani, M. Vasser, C. Wiesmann, A. A. Kossiakoff, S. Koide, and S. S. Sidhu, 2007, High-throughput generation of synthetic antibodies from highly functional minimalist phage-displayed libraries: J Mol Biol, v. 373, p. 924-40.

Graille, M., E. A. Stura, A. L. Corper, B. J. Sutton, M. J. Taussig, J. B. Charbonnier, and G. J. Silverman, 2000, Crystal structure of a Staphylococcus aureus protein A domain complexed with the Fab fragment of a human IgM antibody: structural basis for recognition of B-cell receptors and superantigen activity: Proc Natl Acad Sci USA, v. 97, p. 5399-404.

Graille, M., E. A. Stura, N. G. Housden, J. A. Beckingham, S. P. Bottomley, D. Beale, M. J. Taussig, B. J. Sutton, M. G. Gore, and J. B. Charbonnier, 2001, Complex between Peptostreptococcus magnus protein L and a human antibody reveals structural convergence in the interaction modes of Fab binding proteins: Structure, v. 9, p. 679-87.

Grover, R. K., X. Zhu, T. Nieusma, T. Jones, I. Boero, A. S. MacLeod, A. Mark, S. Niessen, H. J. Kim, L. Kong, N. Assad-Garcia, K. Kwon, M. Chesi, V. V. Smider, D. R. Salomon, D. F. Jelinek, R. A. Kyle, R. B. Pyles, J. I. Glass, A. B. Ward, I. A. Wilson, and R. A. Lerner, 2014, A structurally distinct human mycoplasma protein that generically blocks antigen-antibody union: Science, v. 343, p. 656-61.

Gülich, S., M. Linhult, S. Stahl, and S. Hober, 2002, Engineering streptococcal protein G for increased alkaline stability: Protein Eng, v. 15, p. 835-42.

Huang, J., A. Koide, K. Makabe, and S. Koide, 2008, Design of protein function leaps by directed domain interface evolution: Proc Natl Acad Sci USA, v. 105, p. 6578-83.

Kay, B. K., S. Thai, and V. V. Volgina, 2009, High-throughput biotinylation of proteins: Methods Mol Biol, v. 498, p. 185-96.

Krishnamurthy, V. M., L. A. Estroff, and G. M. Whitesides, Multivalency in Ligand Design. (2006). Fragment-based approaches in drug discovery. Weinheim: Wiley-VCH.

Kunkel, T. A., 1985, Rapid and efficient site-specific mutagenesis without phenotypic selection: Proc Natl Acad Sci USA, v. 82, p. 488-92.

Lo K M, Sudo Y, Chen J, Li Y, Lan Y, Kong S M, Chen L, An Q, Gillies S D. 1998 High level expression and secretion of Fc-X fusion proteins in mammalian cells. Protein Eng. June; 11(6):495-500.

Michnick, S. W., and S. S. Sidhu, 2008, Submitting antibodies to binding arbitration: Nat Chem Biol, v. 4, p. 326-9.

Miller, K. R., A. Koide, B. Leung, J. Fitzsimmons, B. Yoder, H. Yuan, M. Jay, S. S. Sidhu, S. Koide, and E. J. Collins, 2012, T cell receptor-like recognition of tumor in vivo by synthetic antibody fragment: PLoS One, v. 7, p. e43746.

Murtaugh, M. L., S. W. Fanning, T. M. Sharma, A. M. Terry, and J. R. Horn, 2011, A combinatorial histidine scanning library approach to engineer highly pH-dependent protein switches: Protein Sci, v. 20, p. 1619-31.

Nilson, B. H., A. Solomon, L. Bjorck, and B. Akerström, 1992, Protein L from Peptostreptococcus magnus binds to the kappa light chain variable domain: J Biol Chem, v. 267, p. 2234-9.

Pack, P., and A. Plückthun, 1992, Miniantibodies: use of amphipathic helices to produce functional, flexibly linked dimeric FV fragments with high avidity in Escherichia coli: Biochemistry, v. 31, p. 1579-84.

Paduch, M., A. Koide, S. Uysal, S. S. Rizk, S. Koide, and A. A. Kossiakoff, 2013, Generating conformation-specific synthetic antibodies to trap proteins in selected functional states: Methods, v. 60, p. 3-14.

Proudfoot, K. A., C. Torrance, A. D. Lawson, and D. J. King, 1992, Purification of recombinant chimeric B72.3 Fab' and F(ab')2 using streptococcal protein G: Protein Expr Purif, v. 3, p. 368-73.

Ridgeway J B, Presta L G, Carter P. 1996 "Knobs into holes" engineering of antibody CH3 domains for heavy chain heterodimerization. Protein Engineering and Design. 9, 617-21.

Rizk, S. S., M. Paduch, J. H. Heithaus, E. M. Duguid, A. Sandstrom, and A. A. Kossiakoff, 2011, Allosteric control of ligand-binding affinity using engineered conformation-specific effector proteins: Nat Struct Mol Biol, v. 18, p. 437-42.

Sidhu, S. S., H. B. Lowman, B. C. Cunningham, and J. A. Wells, 2000, Phage display for selection of novel binding peptides: Methods Enzymol, v. 328, p. 333-63.

Spiess, C., Zhai, Q., & Carter, P. (2015). Alternative molecular formats and therapeutic applications for bispecific antibodies. Molecular Immunology, 95-106.

Strauch, E. M., S. J. Fleishman, and D. Baker, 2014, Computational design of a pH-sensitive IgG binding protein: Proc Natl Acad Sci USA, v. 111, p. 675-80.

Taussig, M. J., O. Stoevesandt, C. A. Borrebaeck, A. R. Bradbury, D. Cahill, C. Cambillau, A. de Daruvar, S. Dübel, J. Eichler, R. Frank, T. J. Gibson, D. Gloriam, L. Gold, F. W. Herberg, H. Hermjakob, J. D. Hoheisel, T. O. Joos, O. Kallioniemi, M. Koegl, M. Koegll, Z. Konthur, B. Korn, E. Kremmer, S. Krobitsch, U. Landegren, S. van der Maarel, J. McCafferty, S. Muyldermans, P. A. Nygren, S. Palcy, A. Plückthun, B. Polic, M. Przybylski, P. Saviranta, A. Sawyer, D. J. Sherman, A. Skerra, M. Templin, M. Ueffing, and M. Uhlén, 2007, ProteomeBinders: planning a European resource of affinity reagents for analysis of the human proteome: Nat Methods, v. 4, p. 13-7.

The invention claimed is:

1. A polypeptide comprising a modified protein G Fab-binding domain wherein the modified protein G fab binding domain comprises an amino acid sequence having at least 80% sequence identity with SEQ ID NO:3.

2. The polypeptide of claim 1, wherein the polypeptide further comprises a variant immunogenicity region, wherein the variant immunogenicity region comprises a an amino acid sequence having at least 80% sequence identity with one of SEQ ID NOS:27-49.

3. The polypeptide of claim 2, wherein the variant immunogenicity region has an amino acid sequence selected from SEQ ID NOS:27-49.

4. The polypeptide of claim 1, wherein the polypeptide further comprises one or more $F_c$ regions and/or a targeting moiety.

5. A fusion protein comprising two or more polypeptides of claim 1.

6. A protein complex comprising the polypeptide of claim 1 operatively linked to at least one Fab polypeptide.

7. The polypeptide of claim 1, wherein the modified protein G fab binding domain comprises an amino acid sequence having at least 83% sequence identity with SEQ ID NO:3.

8. The polypeptide of claim 1, wherein the modified protein G fab binding domain comprises an amino acid sequence having at least 90% sequence identity with SEQ ID NO:3.

9. The polypeptide of claim 1, wherein the protein G Fab-binding domain comprises a variant isotype recognition region at amino positions corresponding to positions 24-29 of SEQ ID NO:3 and wherein the variant isotype recognition region consists of SEQ ID NO:20.

10. The polypeptide of claim 8, wherein the protein G Fab-binding domain comprises a variant isotype recognition region at amino positions corresponding to positions 24-29 of SEQ ID NO:3 and wherein the variant isotype recognition region consists of SEQ ID NO:20.

11. A nucleic acid encoding for a polypeptide comprising a modified protein G Fab-binding domain wherein the modified protein G fab binding domain comprises an amino acid sequence having at least 80% sequence identity with SEQ ID NO:3.

12. A method for making a polypeptide comprising expressing a nucleic acid encoding for a polypeptide comprising a modified protein G Fab-binding domain wherein the modified protein G fab binding domain comprises an amino acid sequence having at least 80% sequence identity with SEQ ID NO:3 in a host cell.

* * * * *

SEQUENCE LISTING

```
<160> NUMBER OF SEQ ID NOS: 125

<210> SEQ ID NO 1
<211> LENGTH: 480
<212> TYPE: PRT
<213> ORGANISM: Artificial Sequence
<220> FEATURE:
<223> OTHER INFORMATION: Synthetic Peptide

<400> SEQUENCE: 1

Glu Phe Asn Lys Tyr Gly Val Ser Asp Tyr Tyr Lys Asn Leu Ile Asn
1               5                   10                  15

Asn Ala Lys Thr Val Glu Gly Val Lys Asp Leu Gln Ala Gln Val Val
            20                  25                  30

Glu Ser Ala Lys Lys Ala Arg Ile Ser Glu Ala Thr Asp Gly Leu Ser
        35                  40                  45

Asp Phe Leu Lys Ser Gln Thr Pro Ala Glu Asp Thr Val Lys Ser Ile
    50                  55                  60

Glu Leu Ala Glu Ala Lys Val Leu Ala Asn Arg Glu Leu Asp Lys Tyr
65                  70                  75                  80

Gly Val Ser Asp Tyr His Lys Asn Leu Ile Asn Asn Ala Lys Thr Val
                85                  90                  95

Glu Gly Val Lys Asp Leu Gln Ala Gln Val Val Glu Ser Ala Lys Lys
            100                 105                 110

Ala Arg Ile Ser Glu Ala Thr Asp Gly Leu Ser Asp Phe Leu Lys Ser
        115                 120                 125

Gln Thr Pro Ala Glu Asp Thr Val Lys Ser Ile Glu Leu Ala Glu Ala
    130                 135                 140

Lys Val Leu Ala Asn Arg Glu Leu Asp Lys Tyr Gly Val Ser Asp Tyr
145                 150                 155                 160

Tyr Lys Asn Leu Ile Asn Asn Ala Lys Thr Val Glu Gly Val Lys Ala
                165                 170                 175

Leu Ile Asp Glu Ile Leu Ala Ala Leu Pro Lys Thr Asp Thr Tyr Lys
            180                 185                 190

Leu Ile Leu Asn Gly Lys Thr Leu Lys Gly Glu Thr Thr Thr Glu Ala
        195                 200                 205

Val Asp Ala Ala Thr Ala Glu Lys Val Phe Lys Gln Tyr Ala Asn Asp
    210                 215                 220

Asn Gly Val Asp Gly Glu Trp Thr Tyr Asp Asp Ala Thr Lys Thr Phe
225                 230                 235                 240

Thr Val Thr Glu Lys Pro Glu Val Ile Asp Ala Ser Glu Leu Thr Pro
                245                 250                 255

Ala Val Thr Thr Tyr Lys Leu Val Ile Asn Gly Lys Thr Leu Lys Gly
            260                 265                 270

Glu Thr Thr Thr Glu Ala Val Asp Ala Ala Thr Ala Glu Lys Val Phe
        275                 280                 285

Lys Gln Tyr Ala Asn Asp Asn Gly Val Asp Gly Glu Trp Thr Tyr Asp
    290                 295                 300

Asp Ala Thr Lys Thr Phe Thr Val Thr Glu Lys Pro Glu Val Ile Asp
305                 310                 315                 320
```

```
Ala Ser Glu Leu Thr Pro Ala Val Thr Thr Tyr Lys Leu Val Ile Asn
            325                 330                 335

Gly Lys Thr Leu Lys Gly Glu Thr Thr Thr Lys Ala Val Asp Ala Glu
            340                 345                 350

Thr Ala Glu Lys Ala Phe Lys Gln Tyr Ala Asn Asp Asn Gly Val Asp
            355                 360                 365

Gly Val Trp Thr Tyr Asp Asp Ala Thr Lys Thr Phe Thr Val Thr Glu
            370                 375                 380

Met Val Thr Glu Val Pro Gly Asp Ala Pro Thr Glu Pro Glu Lys Pro
385                 390                 395                 400

Glu Ala Ser Ile Pro Leu Val Pro Leu Thr Pro Ala Thr Pro Ile Ala
            405                 410                 415

Lys Asp Asp Ala Lys Lys Asp Asp Thr Lys Lys Glu Asp Ala Lys Lys
            420                 425                 430

Pro Glu Ala Lys Lys Glu Asp Ala Lys Lys Ala Glu Thr Leu Pro Thr
            435                 440                 445

Thr Gly Glu Gly Ser Asn Pro Phe Phe Thr Ala Ala Ala Leu Ala Val
            450                 455                 460

Met Ala Gly Ala Gly Ala Leu Ala Val Ala Ser Lys Arg Lys Glu Asp
465                 470                 475                 480
```

<210> SEQ ID NO 2
<211> LENGTH: 37
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is Lys, Arg, Glu or Iso
<220> FEATURE:
<221> NAME/KEY: MISC_FEATURE
<222> LOCATION: (3)..(3)
<223> OTHER INFORMATION: Xaa is Leu, Phe or Ala
<220> FEATURE:
<221> NAME/KEY: MISC_FEATURE
<222> LOCATION: (4)..(4)
<223> OTHER INFORMATION: Xaa is Lys, Ser, Trp, Arg or Thr
<220> FEATURE:
<221> NAME/KEY: MISC_FEATURE
<222> LOCATION: (5)..(5)
<223> OTHER INFORMATION: Xaa is Gly or Tyr
<220> FEATURE:
<221> NAME/KEY: MISC_FEATURE
<222> LOCATION: (6)..(6)
<223> OTHER INFORMATION: Xaa is Glu, Tyr, Ala or His
<220> FEATURE:
<221> NAME/KEY: MISC_FEATURE
<222> LOCATION: (7)..(7)
<223> OTHER INFORMATION: Xaa is Thr or Arg
<220> FEATURE:
<221> NAME/KEY: MISC_FEATURE
<222> LOCATION: (8)..(8)
<223> OTHER INFORMATION: Xaa is Thr, Ser, Ala or Gly
<220> FEATURE:
<221> NAME/KEY: MISC_FEATURE
<222> LOCATION: (10)..(10)
<223> OTHER INFORMATION: Xaa is Glu, Lys, Thr, or Gln
<220> FEATURE:
<221> NAME/KEY: MISC_FEATURE
<222> LOCATION: (11)..(30)
<223> OTHER INFORMATION: Xaa is an amino acid sequence wherein up to 15
      of these positions may be absent and wherein the modified protein
      G Fab-binding domain is not KTLKGETTTKAVDAATAEKVFKQYANDNG
<220> FEATURE:
<221> NAME/KEY: MISC_FEATURE
<222> LOCATION: (31)..(31)

```
<223> OTHER INFORMATION: Xaa is Gln or Arg
<220> FEATURE:
<221> NAME/KEY: MISC_FEATURE
<222> LOCATION: (32)..(32)
<223> OTHER INFORMATION: Xaa is Tyr, Iso or Phe
<220> FEATURE:
<221> NAME/KEY: MISC_FEATURE
<222> LOCATION: (34)..(34)
<223> OTHER INFORMATION: Xaa is Asn, Tyr, Phe, His, Lys or Trp
<220> FEATURE:
<221> NAME/KEY: MISC_FEATURE
<222> LOCATION: (35)..(35)
<223> OTHER INFORMATION: Xaa is Asp, Val or Glu
<220> FEATURE:
<221> NAME/KEY: MISC_FEATURE
<222> LOCATION: (36)..(36)
<223> OTHER INFORMATION: Xaa is Asn, His, Gln, or Tyr
<220> FEATURE:
<221> NAME/KEY: MISC_FEATURE
<222> LOCATION: (37)..(37)
<223> OTHER INFORMATION: Xaa is Gly, Glu, Asp, or Pro

<400> SEQUENCE: 2

Xaa Thr Xaa Xaa Xaa Xaa Xaa Xaa Thr Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Ala Xaa Xaa Xaa Xaa
        35

<210> SEQ ID NO 3
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 3

Arg Thr Leu Ser Gly Tyr Thr Thr Thr Thr Ala Val Asp Ala Ala Thr
1               5                   10                  15

Ala Glu Lys Val Phe Lys Gln Tyr Ala Tyr Val His Glu
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 4

Lys Thr Phe Trp Gly Glu Thr Thr Thr Lys Ala Val Asp Ala Ala Thr
1               5                   10                  15

Ala Glu Lys Val Phe Lys Gln Tyr Ala Phe Asp Asn Asp
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 5

Glu Thr Leu Arg Tyr Glu Thr Ser Thr Lys Ala Val Asp Ala Ala Thr
1               5                   10                  15

Ala Glu Lys Val Phe Lys Gln Ile Ala His Asp Gln Gly
```

-continued

```
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 6

Lys Thr Leu Lys Gly Glu Thr Thr Thr Lys Ala Val Asp Ala Ala Thr
1               5                   10                  15

Ala Glu Lys Val Phe Lys Gln Tyr Ala Tyr Val His Asp
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 7

Glu Thr Leu Arg Tyr Glu Thr Ser Thr Lys Ala Val Asp Ala Ala Thr
1               5                   10                  15

Ala Glu Lys Val Phe Lys Arg Ile Ala His Asp Gln Gly
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 8

Lys Thr Ala Ser Gly Ala Arg Ala Thr Lys Ala Val Asp Ala Ala Thr
1               5                   10                  15

Ala Glu Lys Val Phe Lys Gln Tyr Ala Lys Glu Tyr Pro
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 9

Glu Thr Leu Thr Gly Glu Thr Gly Thr Gln Ala Val Asp Ala Ala Thr
1               5                   10                  15

Ala Glu Lys Val Phe Lys Gln Tyr Ala Trp Val Asn Asp
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 10

Ile Thr Leu Lys Gly His Thr Thr Thr Lys Ala Val Asp Ala Ala Thr
1               5                   10                  15
```

Ala Glu Lys Val Phe Lys Gln Tyr Ala Trp Val Asn Asp
            20                  25

<210> SEQ ID NO 11
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 11

Gly Gly Gly Ser
1

<210> SEQ ID NO 12
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 12

Gly Gly Gly Ser Gly Gly Gly Ser Gly Gly Gly Ser
1               5                   10

<210> SEQ ID NO 13
<211> LENGTH: 43
<212> TYPE: PRT
<213> ORGANISM: Artificial Sequence
<220> FEATURE:
<223> OTHER INFORMATION: Synthetic Peptide

<400> SEQUENCE: 13

Leu Thr Pro Ala Val Thr Thr Tyr Lys Leu Val Ile Asn Gly Lys Thr
1               5                   10                  15

Leu Lys Gly Glu Thr Thr Thr Lys Ala Val Asp Ala Glu Thr Ala Glu
            20                  25                  30

Lys Ala Phe Lys Gln Tyr Ala Asn Asp Asn Glu
            35                  40

<210> SEQ ID NO 14
<211> LENGTH: 593
<212> TYPE: PRT
<213> ORGANISM: Artificial Sequence
<220> FEATURE:
<223> OTHER INFORMATION: Synthetic Peptide

<400> SEQUENCE: 14

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
            35                  40                  45

Glu Leu Thr Asn Leu Leu Gly Asn Ser Glu Thr Thr Leu Ala Leu Arg
    50                  55                  60

Asn Glu Glu Ser Ala Thr Ala Asp Leu Thr Ala Ala Val Ala Asp
65                  70                  75                  80

Thr Val Ala Ala Ala Ala Glu Asn Ala Gly Ala Ala Trp Glu
                85                  90                  95

Ala Ala Ala Ala Asp Ala Leu Ala Lys Ala Lys Ala Asp Ala Leu
                100                 105                 110

```
Lys Glu Phe Asn Lys Tyr Gly Val Ser Asp Tyr Tyr Lys Asn Leu Ile
            115                 120                 125
Asn Asn Ala Lys Thr Val Glu Gly Val Lys Asp Leu Gln Ala Gln Val
130                 135                 140
Val Glu Ser Ala Lys Lys Ala Arg Ile Ser Glu Ala Thr Asp Gly Leu
145                 150                 155                 160
Ser Asp Phe Leu Lys Ser Gln Thr Pro Ala Glu Asp Thr Val Lys Ser
                165                 170                 175
Ile Glu Leu Ala Glu Ala Lys Val Leu Ala Asn Arg Glu Leu Asp Lys
            180                 185                 190
Tyr Gly Val Ser Asp Tyr His Lys Asn Leu Ile Asn Asn Ala Lys Thr
        195                 200                 205
Val Glu Gly Val Lys Asp Leu Gln Ala Gln Val Val Glu Ser Ala Lys
    210                 215                 220
Lys Ala Arg Ile Ser Glu Ala Thr Asp Gly Leu Ser Asp Phe Leu Lys
225                 230                 235                 240
Ser Gln Thr Pro Ala Glu Asp Thr Val Lys Ser Ile Glu Leu Ala Glu
                245                 250                 255
Ala Lys Val Leu Ala Asn Arg Glu Leu Asp Lys Tyr Gly Val Ser Asp
            260                 265                 270
Tyr Tyr Lys Asn Leu Ile Asn Asn Ala Lys Thr Val Glu Gly Val Lys
        275                 280                 285
Ala Leu Ile Asp Glu Ile Leu Ala Ala Leu Pro Lys Thr Asp Thr Tyr
    290                 295                 300
Lys Leu Ile Leu Asn Gly Lys Thr Leu Lys Gly Glu Thr Thr Thr Glu
305                 310                 315                 320
Ala Val Asp Ala Ala Thr Ala Glu Lys Val Phe Lys Gln Tyr Ala Asn
                325                 330                 335
Asp Asn Gly Val Asp Gly Glu Trp Thr Tyr Asp Asp Ala Thr Lys Thr
            340                 345                 350
Phe Thr Val Thr Glu Lys Pro Glu Val Ile Asp Ala Ser Glu Leu Thr
        355                 360                 365
Pro Ala Val Thr Thr Tyr Lys Leu Val Ile Asn Gly Lys Thr Leu Lys
    370                 375                 380
Gly Glu Thr Thr Thr Glu Ala Val Asp Ala Ala Thr Ala Glu Lys Val
385                 390                 395                 400
Phe Lys Gln Tyr Ala Asn Asp Asn Gly Val Asp Gly Glu Trp Thr Tyr
                405                 410                 415
Asp Asp Ala Thr Lys Thr Phe Thr Val Thr Glu Lys Pro Glu Val Ile
            420                 425                 430
Asp Ala Ser Glu Leu Thr Pro Ala Val Thr Thr Tyr Lys Leu Val Ile
        435                 440                 445
Asn Gly Lys Thr Leu Lys Gly Glu Thr Thr Thr Lys Ala Val Asp Ala
    450                 455                 460
Glu Thr Ala Glu Lys Ala Phe Lys Gln Tyr Ala Asn Asp Asn Gly Val
465                 470                 475                 480
Asp Gly Val Trp Thr Tyr Asp Asp Ala Thr Lys Thr Phe Thr Val Thr
                485                 490                 495
Glu Met Val Thr Glu Val Pro Gly Asp Ala Pro Thr Glu Pro Glu Lys
            500                 505                 510
Pro Glu Ala Ser Ile Pro Leu Val Pro Leu Thr Pro Ala Thr Pro Ile
        515                 520                 525
Ala Lys Asp Asp Ala Lys Lys Asp Asp Thr Lys Lys Glu Asp Ala Lys
```

```
                 530                 535                 540
Lys Pro Glu Ala Lys Lys Glu Asp Ala Lys Lys Ala Glu Thr Leu Pro
545                 550                 555                 560

Thr Thr Gly Glu Gly Ser Asn Pro Phe Phe Thr Ala Ala Leu Ala
                565                 570                 575

Val Met Ala Gly Ala Gly Ala Leu Ala Val Ala Ser Lys Arg Lys Glu
                580                 585                 590

Asp

<210> SEQ ID NO 15
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 15

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Asn Gly Arg Thr Leu Ser Gly Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 16
<211> LENGTH: 66
<212> TYPE: PRT
<213> ORGANISM: Artificial Sequence
<220> FEATURE:
<223> OTHER INFORMATION: Synthetic Peptide

<400> SEQUENCE: 16

Leu Thr Pro Ala Val Thr Thr Tyr Lys Leu Val Ile Asn Gly Lys Thr
1               5                   10                  15

Leu Lys Gly Glu Thr Thr Thr Lys Ala Val Asp Ala Ala Thr Ala Glu
                20                  25                  30

Lys Val Phe Lys Gln Tyr Ala Asn Asp Asn Gly Val Asp Gly Glu Trp
            35                  40                  45

Thr Tyr Asp Asp Ala Thr Lys Thr Phe Thr Val Thr Glu Lys Pro Glu
```

Val Ile
65

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 17

Lys Leu Val Ile Asn Gly Arg Thr Leu Ser Gly
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 18

Tyr Ala Asn Asp Asn Gly
1               5

<210> SEQ ID NO 19
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 19

Lys Thr Leu Lys Gly Glu Thr Thr Thr Lys Ala Val Asp Ala Ala Thr
1               5                   10                  15

Ala Glu Lys Val Phe Lys Gln Tyr Ala Asn Asp Asn Gly
            20                  25

<210> SEQ ID NO 20
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 20

Tyr Ala Tyr Val His Glu
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 21

Tyr Ser Arg Pro His Val
1               5

<210> SEQ ID NO 22
<211> LENGTH: 6
<212> TYPE: PRT
<213> ORGANISM: Artificial Sequence
<220> FEATURE:

```
<223> OTHER INFORMATION: Synthetic Peptide

<400> SEQUENCE: 22

Tyr Ala Val Gly Ala Val
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 23

Tyr Ala Ala Pro His Val
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 24

Tyr Ser His Pro His Val
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 25

Cys Thr Val Trp Pro Val
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 26

Tyr Ala Phe Ala His Val
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 27

Leu Val Ile Arg Gly Leu Thr Leu Ser Leu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide
```

<400> SEQUENCE: 28

Leu Val Ile Arg Gly Leu Thr Leu Ser Phe
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 29

Leu Val Ile Gly Gly Leu Arg Leu Trp Phe
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 30

Leu Val Ile Arg Gly Val Thr Leu Leu Phe
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 31

Leu Val Ile Arg Gly Ile Thr Leu Gly Phe
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 32

Leu Val Ile Met Gly Ser Thr Leu Ser Leu
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 33

Leu Val Ile Ile Gly Arg Thr Leu Ser Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 34

Leu Val Ile Ser Gly Ile Thr Leu Ser Phe
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 35

Leu Val Ile Gly Gly Arg Thr Leu Ser Phe
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 36

Leu Val Ile Gly Gly Arg Thr Leu Ser Phe
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 37

Leu Val Ile Ser Gly Ser Thr Leu Ser Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 38

Leu Val Ile Leu Gly Arg Thr Leu Ser Val
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 39

Phe Val Ile Arg Gly Arg Thr Leu Ser Phe
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 40

```
Leu Val Ile Ser Gly Arg Thr Leu Ser Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 41

Leu Val Ile Gly Gly Arg Thr Leu Arg Phe
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 42

Leu Val Ile Arg Gly Val Thr Leu Gly Phe
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 43

Leu Val Ile Arg Gly Arg Thr Leu Ser Leu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 44

Leu Val Ile Gly Gly Arg Thr Leu Arg Phe
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 45

Leu Val Ile Gly Gly Arg Thr Leu Ser Phe
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 46
```

```
Leu Val Ile Ser Gly Leu Thr Leu Ser Phe
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 47

Leu Val Ile Gly Gly Val Thr Leu Ser Phe
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 48

Leu Val Ile Arg Gly Val Thr Leu Ser Leu
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 49

Leu Val Ile Gly Gly Ile Thr Leu Ser Phe
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 50

Leu Val Ile Asn Gly Arg Thr Leu Ser Gly
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 51

Ala Val Asp Ala Ala Thr Ala Glu Lys Val Phe Lys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 52

Leu Thr Pro Ala Val Thr Thr Tyr Lys Leu Val Ile Asn Gly
```

<210> SEQ ID NO 53
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 53

Val Asp Gly Glu Trp Thr Tyr Asp Asp Ala Thr Lys Thr Phe Thr Val
1               5                   10                  15

Thr Glu Lys Pro Glu Val Ile
            20

<210> SEQ ID NO 54
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 54

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Arg Thr Leu Ser Gly Tyr Thr Thr Thr Thr Ala Val
65                  70                  75                  80

Asp Ala Ala Thr Ala Glu Lys Val Phe Lys Gln Tyr Ala Tyr Val His
                85                  90                  95

Glu Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Asn Gly Arg Thr Leu Ser Gly Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 55
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 55

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

```
Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
 50                  55                  60

Val Ile Asn Gly Lys Thr Phe Trp Gly Glu Thr Thr Lys Ala Val
 65                  70                  75                  80

Asp Ala Ala Thr Ala Glu Lys Val Phe Lys Gln Tyr Ala Phe Asp Asn
                 85                  90                  95

Asp Val Asp Gly Glu Trp Thr Tyr Asp Asp Ala Thr Lys Thr Phe Thr
                100                 105                 110

Val Thr Glu Lys Pro Glu Val Ile Asp Ala Ser Glu Leu Thr Pro Ala
                115                 120                 125

Val Thr Thr Tyr Lys Leu Val Ile Asn Gly Arg Thr Leu Ser Gly Glu
                130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
                180                 185

<210> SEQ ID NO 56
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 56

Met Lys Gly Glu Thr Thr Thr Glu Ala Val Asp Ala Ala Thr Ala Glu
 1               5                  10                  15

Lys Val Phe Lys Gln Tyr Ala Asn Asp Asn Gly Val Asp Gly Glu Trp
                 20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
 50                  55                  60

Val Ile Asn Gly Glu Thr Leu Arg Tyr Glu Thr Ser Thr Lys Ala Val
 65                  70                  75                  80

Asp Ala Ala Thr Ala Glu Lys Val Phe Lys Gln Ile Ala His Asp Gln
                 85                  90                  95

Gly Val Asp Gly Glu Trp Thr Tyr Asp Asp Ala Thr Lys Thr Phe Thr
                100                 105                 110

Val Thr Glu Lys Pro Glu Val Ile Asp Ala Ser Glu Leu Thr Pro Ala
                115                 120                 125

Val Thr Thr Tyr Lys Leu Val Ile Asn Gly Arg Thr Leu Ser Gly Glu
                130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
                180                 185

<210> SEQ ID NO 57
```

```
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 57

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Lys Ala Val
65                  70                  75                  80

Asp Ala Ala Thr Ala Glu Lys Val Phe Lys Gln Tyr Ala Tyr Val His
                85                  90                  95

Asp Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Asn Gly Arg Thr Leu Ser Gly Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 58
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 58

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Glu Thr Leu Arg Tyr Glu Thr Ser Thr Lys Ala Val
65                  70                  75                  80

Asp Ala Ala Thr Ala Glu Lys Val Phe Lys Arg Ile Ala His Asp Gln
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Asn Gly Arg Thr Leu Ser Gly Glu
```

```
                130             135             140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 59
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 59

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
50                  55                  60

Val Ile Asn Gly Lys Thr Ala Ser Gly Ala Arg Ala Thr Lys Ala Val
65                  70                  75                  80

Asp Ala Ala Thr Ala Glu Lys Val Phe Lys Gln Tyr Ala Lys Glu Tyr
                85                  90                  95

Pro Val Asp Gly Glu Trp Thr Tyr Asp Asp Ala Thr Lys Thr Phe Thr
                100                 105                 110

Val Thr Glu Lys Pro Glu Val Ile Asp Ala Ser Glu Leu Thr Pro Ala
            115                 120                 125

Val Thr Thr Tyr Lys Leu Val Ile Asn Gly Arg Thr Leu Ser Gly Glu
            130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 60
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 60

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
50                  55                  60
```

```
Val Ile Asn Gly Glu Thr Leu Thr Gly Glu Thr Gly Thr Gln Ala Val
 65                  70                  75                  80

Asp Ala Ala Thr Ala Glu Lys Val Phe Lys Gln Tyr Ala Trp Val Asn
                 85                  90                  95

Asp Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Asn Gly Arg Thr Leu Ser Gly Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 61
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 61

Met Lys Gly Glu Thr Thr Thr Glu Ala Val Asp Ala Ala Thr Ala Glu
  1               5                  10                  15

Lys Val Phe Lys Gln Tyr Ala Asn Asp Asn Gly Val Asp Gly Glu Trp
             20                  25                  30

Thr Tyr Asp Asp Ala Thr Lys Thr Phe Thr Val Thr Glu Lys Pro Glu
         35                  40                  45

Val Ile Asp Ala Ser Glu Leu Thr Pro Ala Val Thr Thr Tyr Lys Leu
     50                  55                  60

Val Ile Asn Gly Ile Thr Leu Lys Gly His Thr Thr Thr Lys Ala Val
 65                  70                  75                  80

Asp Ala Ala Thr Ala Glu Lys Val Phe Lys Gln Tyr Ala Trp Val Asn
                 85                  90                  95

Asp Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Asn Gly Arg Thr Leu Ser Gly Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 62
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 62
```

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
50                      55                  60

Val Ile Asn Gly Lys Thr Leu Lys Gly Glu Thr Thr Thr Glu Ala Val
65              70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
                100                 105                 110

Val Thr Glu Lys Pro Glu Val Ile Asp Ala Ser Glu Leu Thr Pro Ala
            115                 120                 125

Val Thr Thr Tyr Lys Leu Val Ile Asn Gly Arg Thr Leu Ser Gly Glu
            130                 135                 140

Thr Thr Thr Lys Ala Val Asp Ala Glu Thr Ala Glu Lys Ala Phe Lys
145                 150                 155                 160

Gln Tyr Ala Tyr Val His Glu Val Asp Gly Val Trp Thr Tyr Asp Asp
                165                 170                 175

Ala Thr Lys Thr Phe Thr Val Thr Glu
                180                 185

<210> SEQ ID NO 63
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 63

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
50                      55                  60

Val Ile Asn Gly Lys Thr Leu Lys Gly Glu Thr Thr Thr Glu Ala Val
65              70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
                100                 105                 110

Val Thr Glu Lys Pro Glu Val Ile Asp Ala Ser Glu Leu Thr Pro Ala
            115                 120                 125

Val Thr Thr Tyr Lys Leu Val Ile Asn Gly Arg Thr Leu Ser Gly Glu
            130                 135                 140

Thr Thr Thr Lys Ala Val Asp Ala Glu Thr Ala Glu Lys Ala Phe Lys
145                 150                 155                 160

Gln Tyr Ser Arg Pro His Val Val Asp Gly Val Trp Thr Tyr Asp Asp
                165                 170                 175

Ala Thr Lys Thr Phe Thr Val Thr Glu
            180                 185

<210> SEQ ID NO 64
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 64

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Glu Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
            115                 120                 125

Val Thr Thr Tyr Lys Leu Val Ile Asn Gly Arg Thr Leu Ser Gly Glu
        130                 135                 140

Thr Thr Thr Lys Ala Val Asp Ala Glu Thr Ala Glu Lys Ala Phe Lys
145                 150                 155                 160

Gln Tyr Ala Tyr Gly Ala Val Val Asp Gly Val Trp Thr Tyr Asp Asp
                165                 170                 175

Ala Thr Lys Thr Phe Thr Val Thr Glu
            180                 185

<210> SEQ ID NO 65
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 65

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Glu Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr

```
                   100                 105                 110
Val Thr Glu Lys Pro Glu Val Ile Asp Ala Ser Glu Leu Thr Pro Ala
            115                 120                 125

Val Thr Thr Tyr Lys Leu Val Ile Asn Gly Arg Thr Leu Ser Gly Glu
            130                 135                 140

Thr Thr Thr Lys Ala Val Asp Ala Glu Thr Ala Glu Lys Ala Phe Lys
145                 150                 155                 160

Gln Tyr Ala Ala Pro His Val Val Asp Gly Val Trp Thr Tyr Asp Asp
                165                 170                 175

Ala Thr Lys Thr Phe Thr Val Thr Glu
            180                 185

<210> SEQ ID NO 66
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 66

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
50                  55                  60

Val Ile Asn Gly Lys Thr Leu Lys Gly Glu Thr Thr Thr Glu Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
                100                 105                 110

Val Thr Glu Lys Pro Glu Val Ile Asp Ala Ser Glu Leu Thr Pro Ala
            115                 120                 125

Val Thr Thr Tyr Lys Leu Val Ile Asn Gly Arg Thr Leu Ser Gly Glu
            130                 135                 140

Thr Thr Thr Lys Ala Val Asp Ala Glu Thr Ala Glu Lys Ala Phe Lys
145                 150                 155                 160

Gln Tyr Ser His Pro His Val Val Asp Gly Val Trp Thr Tyr Asp Asp
                165                 170                 175

Ala Thr Lys Thr Phe Thr Val Thr Glu
            180                 185

<210> SEQ ID NO 67
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 67

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30
```

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
 50                  55                  60

Val Ile Asn Gly Lys Thr Leu Lys Gly Glu Thr Thr Thr Glu Ala Val
 65                  70                  75                  80

Asp Ala Ala Thr Ala Glu Lys Val Phe Lys Gln Tyr Ala Asn Asp Asn
                 85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
            115                 120                 125

Val Thr Thr Tyr Lys Leu Val Ile Asn Gly Arg Thr Leu Ser Gly Glu
            130                 135                 140

Thr Thr Thr Lys Ala Val Asp Ala Glu Thr Ala Glu Lys Ala Phe Lys
145                 150                 155                 160

Gln Cys Thr Val Trp Pro Val Val Asp Gly Val Trp Thr Tyr Asp Asp
                165                 170                 175

Ala Thr Lys Thr Phe Thr Val Thr Glu
                180                 185

<210> SEQ ID NO 68
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 68

Met Lys Gly Glu Thr Thr Thr Glu Ala Val Asp Ala Ala Thr Ala Glu
 1               5                  10                  15

Lys Val Phe Lys Gln Tyr Ala Asn Asp Asn Gly Val Asp Gly Glu Trp
                 20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
 50                  55                  60

Val Ile Asn Gly Lys Thr Leu Lys Gly Glu Thr Thr Thr Glu Ala Val
 65                  70                  75                  80

Asp Ala Ala Thr Ala Glu Lys Val Phe Lys Gln Tyr Ala Asn Asp Asn
                 85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
            115                 120                 125

Val Thr Thr Tyr Lys Leu Val Ile Asn Gly Arg Thr Leu Ser Gly Glu
            130                 135                 140

Thr Thr Thr Lys Ala Val Asp Ala Glu Thr Ala Glu Lys Ala Phe Lys
145                 150                 155                 160

Gln Tyr Ala Phe Ala His Val Val Asp Gly Val Trp Thr Tyr Asp Asp
                165                 170                 175

Ala Thr Lys Thr Phe Thr Val Thr Glu
                180                 185

<210> SEQ ID NO 69
<211> LENGTH: 185

```
<212> TYPE: PRT
<213> ORGANISM: Artificial Sequence
<220> FEATURE:
<223> OTHER INFORMATION: Synthetic Peptide

<400> SEQUENCE: 69

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Arg Gly Leu Thr Leu Ser Leu Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 70
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 70

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Arg Gly Leu Thr Leu Ser Phe Glu
    130                 135                 140
```

```
Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 71
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 71

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Gly Gly Leu Arg Leu Trp Phe Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 72
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 72

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Lys Ala Val
```

65                  70                  75                  80
Asp Ala Ala Thr Ala Glu Lys Val Phe Lys Gln Tyr Ala Asn Asp Asn
                      85                  90                  95

Gly Val Asp Gly Glu Trp Thr Tyr Asp Asp Ala Thr Lys Thr Phe Thr
                 100                 105                 110

Val Thr Glu Lys Pro Glu Val Ile Asp Ala Ser Glu Leu Thr Pro Ala
             115                 120                 125

Val Thr Thr Tyr Lys Leu Val Ile Arg Gly Val Thr Leu Leu Phe Glu
         130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                 165                 170                 175

Ala Thr Lys Thr Phe Thr Val Thr Glu
             180                 185

<210> SEQ ID NO 73
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 73

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
             20                  25                  30

Thr Tyr Asp Asp Ala Thr Lys Thr Phe Thr Val Thr Glu Lys Pro Glu
         35                  40                  45

Val Ile Asp Ala Ser Glu Leu Thr Pro Ala Val Thr Thr Tyr Lys Leu
     50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                 85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Arg Gly Ile Thr Leu Gly Phe Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 74
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 74

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
            115                 120                 125

Val Thr Thr Tyr Lys Leu Val Ile Met Gly Ser Thr Leu Ser Leu Glu
            130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 75
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 75

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
            115                 120                 125

Val Thr Thr Tyr Lys Leu Val Ile Ile Gly Arg Thr Leu Ser Leu Glu
            130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

```
Ala Thr Lys Thr Phe Thr Val Thr Glu
            180                 185

<210> SEQ ID NO 76
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 76

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Ser Gly Ile Thr Leu Ser Phe Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 77
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 77

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110
```

Val Thr Glu Lys Pro Glu Val Ile Asp Ala Ser Glu Leu Thr Pro Ala
            115                 120                 125

Val Thr Thr Tyr Lys Leu Val Ile Gly Gly Arg Thr Leu Ser Phe Glu
            130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 78
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 78

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
            115                 120                 125

Val Thr Thr Tyr Lys Leu Val Ile Gly Gly Arg Thr Leu Ser Phe Glu
            130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 79
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 79

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu

```
                    35                  40                  45
Val Ile Asp Ala Ser Glu Leu Thr Pro Ala Val Thr Thr Tyr Lys Leu
 50                  55                  60

Val Ile Asn Gly Lys Thr Leu Lys Gly Glu Thr Thr Lys Ala Val
 65                  70                  75                  80

Asp Ala Ala Thr Ala Glu Lys Val Phe Lys Gln Tyr Ala Asn Asp Asn
                 85                  90                  95

Gly Val Asp Gly Glu Trp Thr Tyr Asp Asp Ala Thr Lys Thr Phe Thr
                100                 105                 110

Val Thr Glu Lys Pro Glu Val Ile Asp Ala Ser Glu Leu Thr Pro Ala
                115                 120                 125

Val Thr Thr Tyr Lys Leu Val Ile Ser Gly Ser Thr Leu Ser Leu Glu
                130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
                180                 185

<210> SEQ ID NO 80
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 80

Met Lys Gly Glu Thr Thr Thr Glu Ala Val Asp Ala Ala Thr Ala Glu
 1                   5                  10                  15

Lys Val Phe Lys Gln Tyr Ala Asn Asp Asn Gly Val Asp Gly Glu Trp
                 20                  25                  30

Thr Tyr Asp Asp Ala Thr Lys Thr Phe Thr Val Thr Glu Lys Pro Glu
                 35                  40                  45

Val Ile Asp Ala Ser Glu Leu Thr Pro Ala Val Thr Thr Tyr Lys Leu
 50                  55                  60

Val Ile Asn Gly Lys Thr Leu Lys Gly Glu Thr Thr Lys Ala Val
 65                  70                  75                  80

Asp Ala Ala Thr Ala Glu Lys Val Phe Lys Gln Tyr Ala Asn Asp Asn
                 85                  90                  95

Gly Val Asp Gly Glu Trp Thr Tyr Asp Asp Ala Thr Lys Thr Phe Thr
                100                 105                 110

Val Thr Glu Lys Pro Glu Val Ile Asp Ala Ser Glu Leu Thr Pro Ala
                115                 120                 125

Val Thr Thr Tyr Lys Leu Val Ile Leu Gly Arg Thr Leu Ser Val Glu
                130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
                180                 185

<210> SEQ ID NO 81
<211> LENGTH: 185
<212> TYPE: PRT
```

<213> ORGANISM: Artificial Sequence
<220> FEATURE:
<223> OTHER INFORMATION: Synthetic Peptide

<400> SEQUENCE: 81

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Phe Val Ile Arg Gly Arg Thr Leu Ser Phe Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 82
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 82

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Ser Gly Arg Thr Leu Ser Leu Glu
    130                 135                 140

```
Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185
```

<210> SEQ ID NO 83
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 83

```
Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Gly Gly Arg Thr Leu Arg Phe Glu
        130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185
```

<210> SEQ ID NO 84
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 84

```
Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Lys Ala Val
65                  70                  75                  80
```

```
Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Arg Gly Val Thr Leu Gly Phe Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 85
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 85

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
                20                  25                  30

Thr Tyr Asp Asp Ala Thr Lys Thr Phe Thr Val Thr Glu Lys Pro Glu
            35                  40                  45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Arg Gly Arg Thr Leu Ser Leu Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 86
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 86

Met Lys Gly Glu Thr Thr Thr Glu Ala Val Asp Ala Ala Thr Ala Glu
```

```
              1               5                  10                 15
Lys Val Phe Lys Gln Tyr Ala Asn Asp Asn Gly Val Asp Gly Glu Trp
                 20                  25                 30

Thr Tyr Asp Asp Ala Thr Lys Thr Phe Thr Val Thr Glu Lys Pro Glu
                 35                  40              45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                 85                  90                  95

Gly Val Asp Gly Glu Trp Thr Tyr Asp Asp Ala Thr Lys Thr Phe Thr
                100                 105                110

Val Thr Glu Lys Pro Glu Val Ile Asp Ala Ser Glu Leu Thr Pro Ala
             115                 120                 125

Val Thr Thr Tyr Lys Leu Val Ile Gly Gly Arg Thr Leu Arg Phe Glu
             130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
                180                 185

<210> SEQ ID NO 87
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 87

Met Lys Gly Glu Thr Thr Thr Glu Ala Val Asp Ala Ala Thr Ala Glu
1               5                  10                  15

Lys Val Phe Lys Gln Tyr Ala Asn Asp Asn Gly Val Asp Gly Glu Trp
                 20                  25                 30

Thr Tyr Asp Asp Ala Thr Lys Thr Phe Thr Val Thr Glu Lys Pro Glu
                 35                  40              45

Val Ile Asp Ala Ser Glu Leu Thr Pro Ala Val Thr Thr Tyr Lys Leu
        50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                 85                  90                  95

Gly Val Asp Gly Glu Trp Thr Tyr Asp Asp Ala Thr Lys Thr Phe Thr
                100                 105                110

Val Thr Glu Lys Pro Glu Val Ile Asp Ala Ser Glu Leu Thr Pro Ala
             115                 120                 125

Val Thr Thr Tyr Lys Leu Val Ile Gly Gly Arg Thr Leu Ser Phe Glu
             130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
```

```
                    180                 185

<210> SEQ ID NO 88
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 88

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Ser Gly Leu Thr Leu Ser Phe Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 89
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 89

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110
```

```
Val Thr Glu Lys Pro Glu Val Ile Asp Ala Ser Glu Leu Thr Pro Ala
            115                 120                 125

Val Thr Thr Tyr Lys Leu Val Ile Gly Gly Val Thr Leu Ser Phe Glu
        130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 90
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 90

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45

Val Ile Asp Ala Ser Glu Leu Thr Pro Ala Val Thr Thr Tyr Lys Leu
    50                  55                  60

Val Ile Asn Gly Lys Thr Leu Lys Gly Glu Thr Thr Thr Lys Ala Val
65                  70                  75                  80

Asp Ala Ala Thr Ala Glu Lys Val Phe Lys Gln Tyr Ala Asn Asp Asn
                85                  90                  95

Gly Val Asp Gly Glu Trp Thr Tyr Asp Asp Ala Thr Lys Thr Phe Thr
            100                 105                 110

Val Thr Glu Lys Pro Glu Val Ile Asp Ala Ser Glu Leu Thr Pro Ala
        115                 120                 125

Val Thr Thr Tyr Lys Leu Val Ile Arg Gly Val Thr Leu Ser Leu Glu
    130                 135                 140

Thr Thr Thr Lys Ala Val Asp Ala Glu Thr Ala Glu Lys Ala Phe Lys
145                 150                 155                 160

Gln Tyr Ala Asn Asp Asn Gly Val Asp Gly Val Trp Thr Tyr Asp Asp
                165                 170                 175

Ala Thr Lys Thr Phe Thr Val Thr Glu
            180                 185

<210> SEQ ID NO 91
<211> LENGTH: 185
<212> TYPE: PRT
<213> ORGANISM: Artificial Sequence
<220> FEATURE:
<223> OTHER INFORMATION: Synthetic Peptide

<400> SEQUENCE: 91

Met Lys Gly Glu Thr Thr Thr Glu Ala Val Asp Ala Ala Thr Ala Glu
1               5                   10                  15

Lys Val Phe Lys Gln Tyr Ala Asn Asp Asn Gly Val Asp Gly Glu Trp
            20                  25                  30

Thr Tyr Asp Asp Ala Thr Lys Thr Phe Thr Val Thr Glu Lys Pro Glu
        35                  40                  45
```

```
Val Ile Asp Ala Ser Glu Leu Thr Pro Ala Val Thr Thr Tyr Lys Leu
 50                  55                  60
Val Ile Asn Gly Lys Thr Leu Lys Gly Glu Thr Thr Thr Lys Ala Val
 65                  70                  75                  80
Asp Ala Ala Thr Ala Glu Lys Val Phe Lys Gln Tyr Ala Asn Asp Asn
                 85                  90                  95
Gly Val Asp Gly Glu Trp Thr Tyr Asp Asp Ala Thr Lys Thr Phe Thr
                100                 105                 110
Val Thr Glu Lys Pro Glu Val Ile Asp Ala Ser Glu Leu Thr Pro Ala
            115                 120                 125
Val Thr Thr Tyr Lys Leu Val Ile Gly Gly Ile Thr Leu Ser Phe Glu
            130                 135                 140
Thr Thr Thr Lys Ala Val Asp Ala Glu Thr Ala Glu Lys Ala Phe Lys
145                 150                 155                 160
Gln Tyr Ala Asn Asp Asn Gly Val Asp Gly Val Trp Thr Tyr Asp Asp
                165                 170                 175
Ala Thr Lys Thr Phe Thr Val Thr Glu
            180                 185

<210> SEQ ID NO 92
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 92

Lys Thr Leu Lys Gly Glu Thr Thr Thr Glu Ala Val Asp Ala Ala Thr
1               5                   10                  15
Ala Glu Lys Val Phe Lys Gln Tyr Ala Asn Asp Asn Gly
            20                  25

<210> SEQ ID NO 93
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 93

Lys Thr Leu Lys Gly Glu Thr Thr Thr Lys Ala Val Asp Ala Glu Thr
1               5                   10                  15
Ala Glu Lys Ala Phe Lys Gln Tyr Ala Asn Asp Asn Gly
            20                  25

<210> SEQ ID NO 94
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 94

Leu Ala Ala Ala
1

<210> SEQ ID NO 95
<211> LENGTH: 19
<212> TYPE: PRT
<213> ORGANISM: Artificial Sequence
<220> FEATURE:
```

```
<223> OTHER INFORMATION: Synthetic Peptide

<400> SEQUENCE: 95

Leu Gly Gly Gly Gly Ser Gly Gly Gly Ser Gly Gly Gly Gly Ser
1               5                   10                  15

Ala Ala Ala

<210> SEQ ID NO 96
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 96

Leu Ser Gly Gly Gly Gly Ser Gly Gly Gly Ser Gly Gly Gly Gly
1               5                   10                  15

Ser Gly Gly Gly Gly Ser Ala Ala Ala
            20                  25

<210> SEQ ID NO 97
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 97

Leu Ala Glu Ala Ala Ala Lys Glu Ala Ala Lys Ala Ala Ala
1               5                   10                  15

<210> SEQ ID NO 98
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 98

Leu Ala Glu Ala Ala Ala Lys Glu Ala Ala Lys Glu Ala Ala Ala
1               5                   10                  15

Lys Ala Ala Ala
            20

<210> SEQ ID NO 99
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 99

Leu Ala Glu Ala Ala Ala Lys Glu Ala Ala Lys Glu Ala Ala Ala
1               5                   10                  15

Lys Glu Ala Ala Ala Lys Ala Ala Ala
            20                  25

<210> SEQ ID NO 100
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 100
```

```
Leu Ala Glu Ala Ala Ala Lys Glu Ala Ala Lys Glu Ala Ala Ala
1               5                   10                  15

Lys Glu Ala Ala Ala Lys Glu Ala Ala Lys Ala Ala Ala
            20                  25                  30

<210> SEQ ID NO 101
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Leu or Phe
<220> FEATURE:
<221> NAME/KEY: MISC_FEATURE
<222> LOCATION: (4)..(4)
<223> OTHER INFORMATION: Xaa is Asn, Arg, Gly, Met, Iso, Ser or Leu
<220> FEATURE:
<221> NAME/KEY: MISC_FEATURE
<222> LOCATION: (6)..(6)
<223> OTHER INFORMATION: Xaa is Arg, Leu, Val, Iso or Ser
<220> FEATURE:
<221> NAME/KEY: MISC_FEATURE
<222> LOCATION: (7)..(7)
<223> OTHER INFORMATION: Xaa is Thr or Arg
<220> FEATURE:
<221> NAME/KEY: MISC_FEATURE
<222> LOCATION: (9)..(9)
<223> OTHER INFORMATION: Xaa is Ser, Trp, Leu, Gly or Arg
<220> FEATURE:
<221> NAME/KEY: MISC_FEATURE
<222> LOCATION: (10)..(10)
<223> OTHER INFORMATION: Xaa is Leu, Phe or Val

<400> SEQUENCE: 101

Xaa Val Ile Xaa Gly Xaa Xaa Leu Xaa Xaa
1               5                   10

<210> SEQ ID NO 102
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 102

Pro Glu Glu Leu Arg Thr Asn Lys
1               5

<210> SEQ ID NO 103
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 103

Pro Pro Ser Asp Ser Gln Leu Lys Ser Gly Thr Ala
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 104
```

```
Pro Pro Ser Ser Glu Glu Leu Gln Ala Asn Thr Ala
1               5                   10
```

<210> SEQ ID NO 105
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 105

```
Asp Ser Gln Leu Lys Ser Gly Thr
1               5
```

<210> SEQ ID NO 106
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 106

```
Ser Glu Glu Leu Gln Ala Asn Lys
1               5
```

<210> SEQ ID NO 107
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 107

```
Lys Thr Leu Lys Gly Glu Thr Thr Thr Lys
1               5                   10
```

<210> SEQ ID NO 108
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 108

```
Gln Tyr Ala Asn Asp Asn Gly
1               5
```

<210> SEQ ID NO 109
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 109

```
Arg Thr Leu Ser Gly Tyr Thr Thr Thr Thr
1               5                   10
```

<210> SEQ ID NO 110
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 110

Gln Tyr Ala Tyr Val His Glu
1               5

<210> SEQ ID NO 111
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 111

Lys Thr Phe Trp Gly Glu Thr Thr Thr Lys
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 112

Gln Tyr Ala Phe Val Asn Asp
1               5

<210> SEQ ID NO 113
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 113

Glu Thr Leu Arg Tyr Glu Thr Ser Thr Lys
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 114

Gln Ile Ala His Asp Gln Gly
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 115

Gln Tyr Ala Tyr Val His Asp
1               5

<210> SEQ ID NO 116
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 116

Glu Thr Leu Arg Tyr Glu Thr Ser Thr Lys

```
1               5                   10
```

<210> SEQ ID NO 117
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 117

```
Arg Ile Ala His Asp Gln Gly
1               5
```

<210> SEQ ID NO 118
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 118

```
Lys Thr Ala Ser Gly Ala Arg Ala Thr Lys
1               5                   10
```

<210> SEQ ID NO 119
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 119

```
Gln Tyr Ala Lys Glu Tyr Pro
1               5
```

<210> SEQ ID NO 120
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 120

```
Glu Thr Leu Thr Gly Glu Thr Gly Thr Gln
1               5                   10
```

<210> SEQ ID NO 121
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 121

```
Gln Phe Ala Tyr Asp Asn Asp
1               5
```

<210> SEQ ID NO 122
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 122

```
Ile Thr Leu Lys Glu His Thr Thr Thr Lys
1               5                   10
```

```
<210> SEQ ID NO 123
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 123

Gln Tyr Ala Trp Val Asn Asp
1               5

<210> SEQ ID NO 124
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is Glu, Lys, Iso, or Arg
<220> FEATURE:
<221> NAME/KEY: MISC_FEATURE
<222> LOCATION: (3)..(3)
<223> OTHER INFORMATION: Xaa is Leu, Phe, or Ala
<220> FEATURE:
<221> NAME/KEY: MISC_FEATURE
<222> LOCATION: (4)..(4)
<223> OTHER INFORMATION: Xaa is Lys, Arg, Ser, Thr, or Trp
<220> FEATURE:
<221> NAME/KEY: MISC_FEATURE
<222> LOCATION: (5)..(5)
<223> OTHER INFORMATION: Xaa is Gly or Tyr
<220> FEATURE:
<221> NAME/KEY: MISC_FEATURE
<222> LOCATION: (6)..(6)
<223> OTHER INFORMATION: Xaa Glu, Tyr, Ala or His
<220> FEATURE:
<221> NAME/KEY: MISC_FEATURE
<222> LOCATION: (7)..(7)
<223> OTHER INFORMATION: Xaa is Thr or Arg
<220> FEATURE:
<221> NAME/KEY: MISC_FEATURE
<222> LOCATION: (8)..(8)
<223> OTHER INFORMATION: Xaa is Thr, Ser, Ala or Gly
<220> FEATURE:
<221> NAME/KEY: MISC_FEATURE
<222> LOCATION: (10)..(10)
<223> OTHER INFORMATION: Xaa is Lys, Gln, or Thr

<400> SEQUENCE: 124

Xaa Thr Xaa Xaa Xaa Xaa Xaa Xaa Thr Xaa
1               5                   10

<210> SEQ ID NO 125
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is Gln or Arg
<220> FEATURE:
<221> NAME/KEY: MISC_FEATURE
<222> LOCATION: (2)..(2)
<223> OTHER INFORMATION: Xaa is Tyr, Iso or Phe
<220> FEATURE:
<221> NAME/KEY: MISC_FEATURE
<222> LOCATION: (4)..(4)
<223> OTHER INFORMATION: Xaa is Tyr, His, Phe, Lys or Trp
<220> FEATURE:
```

```
<221> NAME/KEY: MISC_FEATURE
<222> LOCATION: (5)..(5)
<223> OTHER INFORMATION: Xaa is Val, Asp, or Glu
<220> FEATURE:
<221> NAME/KEY: MISC_FEATURE
<222> LOCATION: (6)..(6)
<223> OTHER INFORMATION: Xaa is Asn, His, Gln or Tyr
<220> FEATURE:
<221> NAME/KEY: MISC_FEATURE
<222> LOCATION: (7)..(7)
<223> OTHER INFORMATION: Xaa is Asp, Gly, Glu or Pro

<400> SEQUENCE: 125

Xaa Xaa Ala Xaa Xaa Xaa Xaa
1               5
```